US008738111B2

(12) United States Patent
Sweeney et al.

(10) Patent No.: US 8,738,111 B2
(45) Date of Patent: *May 27, 2014

(54) CARDIAC CONTRACTION DETECTION USING INFORMATION INDICATIVE OF LEAD MOTION

(75) Inventors: Robert J. Sweeney, Woodbury, MN (US); Allan C. Shuros, St. Paul, MN (US); Krzysztof Z. Siejko, Maple Grove, MN (US); David C. Olson, Eden Prairie, MN (US); Frank Ingle, Palo Alto, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 119 days.

This patent is subject to a terminal disclaimer.

(21) Appl. No.: 13/168,507

(22) Filed: Jun. 24, 2011

(65) Prior Publication Data

US 2011/0319776 A1 Dec. 29, 2011

Related U.S. Application Data

(60) Provisional application No. 61/359,430, filed on Jun. 29, 2010.

(51) Int. Cl.
*A61B 5/02* (2006.01)
*A61B 5/04* (2006.01)
*A61B 5/05* (2006.01)
*A61N 1/00* (2006.01)

(52) U.S. Cl.
USPC ........... 600/381; 600/485; 600/486; 600/547; 607/18

(58) Field of Classification Search
USPC ................ 607/4–38, 119–132; 600/373–375, 600/449–450, 481–503, 508–528, 381, 547
See application file for complete search history.

(56) References Cited

U.S. PATENT DOCUMENTS 3,012,192 A 12/1961 Lion
4,011,500 A 3/1977 Pelletier et al.
(Continued)

FOREIGN PATENT DOCUMENTS

EP 0578748 B1 5/1996
EP 0670743 B1 12/2001
(Continued)

OTHER PUBLICATIONS

"U.S. Appl. No. 13/168,481 , Response filed Feb. 19, 2013 to Non Final Office Action mailed Nov. 19, 2012", 11 pgs.

(Continued)

*Primary Examiner* — Niketa Patel
*Assistant Examiner* — Lindsey G Hankins
(74) *Attorney, Agent, or Firm* — Schwegman Lundberg & Woessner, P.A.

(57) ABSTRACT

Systems and methods for cardiac contraction detection using information indicative of lead motion are described. In an example, an implantable medical device can include a receiver circuit configured to be electrically coupled to conductor comprising a portion of an implantable lead and be configured to obtain information indicative of a movement of the implantable lead due at least in part to a motion of a heart. The device can include a processor circuit configured to determine whether a cardiac mechanical contraction occurred during a specified interval included in the obtained information indicative of the movement of the implantable lead. The processor circuit can be configured to determine information about the cardiac mechanical contraction using the obtained information indicative of the movement of the implantable lead.

23 Claims, 21 Drawing Sheets

(56) References Cited

U.S. PATENT DOCUMENTS

| | | | |
|---|---|---|---|
| 5,197,467 A * | 3/1993 | Steinhaus et al. | 607/20 |
| 5,271,392 A | 12/1993 | Ferek-Petric | |
| 5,324,326 A | 6/1994 | Lubin | |
| 5,361,776 A | 11/1994 | Samuelson et al. | |
| 5,417,717 A * | 5/1995 | Salo et al. | 607/18 |
| 5,448,222 A | 9/1995 | Harman | |
| 5,554,177 A | 9/1996 | Kieval et al. | |
| 5,564,434 A | 10/1996 | Halperin et al. | |
| 5,693,074 A | 12/1997 | Ferek-Petric | |
| 5,694,943 A | 12/1997 | Brewer et al. | |
| 5,897,577 A | 4/1999 | Cinbis et al. | |
| 5,899,927 A | 5/1999 | Ecker et al. | |
| 6,094,981 A | 8/2000 | Hochstein | |
| 6,285,898 B1 | 9/2001 | Ben-Haim | |
| 6,317,628 B1 | 11/2001 | Linder et al. | |
| 6,445,951 B1 | 9/2002 | Mouchawar | |
| 6,591,143 B1 | 7/2003 | Ekwall | |
| 6,731,973 B2 | 5/2004 | Voith et al. | |
| 6,869,404 B2 | 3/2005 | Schulhauser et al. | |
| 6,873,870 B2 | 3/2005 | Ferek-Petric | |
| 6,980,866 B2 | 12/2005 | Yu et al. | |
| 7,025,727 B2 | 4/2006 | Brockway et al. | |
| 7,035,684 B2 | 4/2006 | Lee | |
| 7,047,083 B2 | 5/2006 | Gunderson et al. | |
| 7,248,923 B2 | 7/2007 | Maile et al. | |
| 7,689,286 B2 | 3/2010 | Pastore et al. | |
| 7,787,946 B2 | 8/2010 | Stahman et al. | |
| 8,478,392 B2 | 7/2013 | Sweeney et al. | |
| 8,532,770 B2 | 9/2013 | Sweeney et al. | |
| 2005/0137636 A1 | 6/2005 | Gunderson et al. | |
| 2006/0282000 A1 | 12/2006 | Zhang et al. | |
| 2007/0299477 A1 | 12/2007 | Kleckner et al. | |
| 2008/0077333 A1 | 3/2008 | Maxey et al. | |
| 2008/0119750 A1 | 5/2008 | Patangay et al. | |
| 2008/0242976 A1 | 10/2008 | Robertson et al. | |
| 2008/0269820 A1 | 10/2008 | Nilsson | |
| 2008/0294217 A1 | 11/2008 | Lian et al. | |
| 2009/0030334 A1 | 1/2009 | Anderson et al. | |
| 2009/0177110 A1 | 7/2009 | Lyden et al. | |
| 2009/0204163 A1 | 8/2009 | Shuros et al. | |
| 2009/0299432 A1 | 12/2009 | Stadler et al. | |
| 2010/0069768 A1 | 3/2010 | Min et al. | |
| 2010/0076279 A1 | 3/2010 | Shuros et al. | |
| 2010/0179421 A1 | 7/2010 | Tupin | |
| 2010/0280397 A1 | 11/2010 | Feldman et al. | |
| 2011/0009914 A1 | 1/2011 | Brockway et al. | |
| 2011/0319772 A1 | 12/2011 | Ingle | |
| 2011/0319778 A1 | 12/2011 | Sweeney et al. | |
| 2011/0319779 A1 | 12/2011 | Sweeney et al. | |
| 2011/0319782 A1 | 12/2011 | Sweeney et al. | |

FOREIGN PATENT DOCUMENTS

| | | |
|---|---|---|
| EP | 1469910 B1 | 12/2006 |
| EP | 1515770 B1 | 6/2009 |
| JP | 2013531539 A | 8/2013 |
| WO | WO-9503086 A2 | 2/1995 |
| WO | WO-9527531 A1 | 10/1995 |
| WO | WO-2004103458 A2 | 12/2004 |
| WO | WO-2005089638 A1 | 9/2005 |
| WO | WO-2008054261 A1 | 5/2008 |
| WO | WO-2009058638 A1 | 5/2009 |
| WO | WO-2010033190 A2 | 3/2010 |
| WO | WO-2012005985 A2 | 1/2012 |
| WO | WO-2012005985 A3 | 1/2012 |
| WO | WO-2012005987 A2 | 1/2012 |
| WO | WO-2012005987 A3 | 1/2012 |
| WO | WO-2012005988 A2 | 1/2012 |
| WO | WO-2012005988 A3 | 1/2012 |
| WO | WO-2012005989 A2 | 1/2012 |
| WO | WO-2012005989 A3 | 1/2012 |
| WO | WO-2012005991 A2 | 1/2012 |
| WO | WO-2012005991 A3 | 1/2012 |

OTHER PUBLICATIONS

"U.S. Appl. No. 13/168,481, Examiner Interview Summary mailed Feb. 26, 2013", 3 pgs.

"U.S. Appl. No. 13/168,481, Non Final Office Action mailed Nov. 19, 2012", 5 pgs.

"U.S. Appl. No. 13/168,481, Notice of Allowance mailed Mar. 5, 2013", 5 pgs.

"U.S. Appl. No. 13/168,531, Response filed Jan. 8, 2013 to Restriction Requirement mailed Dec. 21, 2012", 9 pgs.

"U.S. Appl. No. 13/168,531, Restriction Requirement mailed Dec. 21, 2012", 6 pgs.

"U.S. Appl. No. 13/168,547, Non Final Office Action mailed Dec. 11, 2012", 10 pgs.

"International Application Serial No. PCT/US2011/041834, International Preliminary Report on Patentability mailed Jan. 17, 2013", 7 pgs.

"International Application Serial No. PCT/US2011/041834, International Search Report mailed Jan. 26, 2012", 3 pgs.

"International Application Serial No. PCT/US2011/041834, International Written Opinion mailed Jan. 26, 2012", 5 pgs.

"International Application Serial No. PCT/US2011/041850, International Preliminary Report on Patentability mailed Jan. 17, 2013", 7 pgs.

"International Application Serial No. PCT/US2011/041850, International Search Report mailed Feb. 1, 2012", 4 pgs.

"International Application Serial No. PCT/US2011/041850, International Written Opinion mailed Feb. 1, 2012", 5 pgs.

"International Application Serial No. PCT/US2011/041854, International Preliminary Report on Patentability mailed Jan. 17, 2013", 6 pgs.

"International Application Serial No. PCT/US2011/041854, International Search Report Mailed Jan. 26, 2012", 4 pgs.

"International Application Serial No. PCT/US2011/041854, International Written Opinion Mailed Jan. 26, 2012", 4 pgs.

"International Application Serial No. PCT/US2011/041860, International Preliminary Report on Patentability mailed Jan. 17, 2013", 7 pgs.

"International Application Serial No. PCT/US2011/041868, International Preliminary Report on Patentability mailed Jan. 17, 2013", 7 pgs.

"International Application Serial No. PCT/US2011/041868, International Search Report mailed Jan. 26, 2012", 4 pgs.

"International Application Serial No. PCT/US2011/041868, International Written Opinion mailed Jan. 26, 2012", 5 pgs.

"International Serial No. PCT/US2011/041860, International Search Report Jan. 26, 2012", 4 pgs.

"International Serial No. PCT/US2011/041860, International Written Opinion mailed Jan. 26, 2012", 5 pgs.

"Japanese Name Application Serial No. [Pending], Voluntary Amendment filed Dec. 27, 2012", With English Claims, 49 pgs.

"Lion's Twin-T Circuit Revisited", IEEE Engineering in Medicine and Biology, (Sep. 1992), 61-66.

Brusich, Sandro, et al., "Cardiac Lead Used as Contractility Sensor: Animal Study", HRS 2011, Innovators Poster Session—Esplanade Foyer Moscone South, (May 6, 2011), 7 pgs.

U.S. Appl. No. 13/168,471, Non Final Office Action mailed Nov. 12, 2013, 15 pgs.

U.S. Appl. No. 13/168,531, Response filed Jul. 31, 2013 to Non Final Office Action mailed May 14, 2013, 15 pgs.

U.S. Appl. No. 13/168,531, Non Final Office Action mailed May 14, 2013, 9 pgs.

U.S. Appl. No. 13/168,531, Notice of Allowance mailed Oct. 1, 2013, 8 pgs.

U.S. Appl. No. 13/168,547, Response filed Apr. 11, 2013 to Non Final Office Action mailed Dec. 11, 2012, 11 pgs.

U.S. Appl. No. 13/168,547, Notice of Allowance mailed Apr. 30, 2013, 8 pgs.

U.S. Appl. No. 13/168,547, PTO Response to Rule 312 Communication mailed Aug. 5, 2013, 2 pgs.

* cited by examiner

CARDIAC CONTRACTION DETECTION USING INFORMATION INDICATIVE OF LEAD MOTION

CLAIM OF PRIORITY

This patent application claims the benefit of priority, under 35 U.S.C. Section 119(e), to Ingle, U.S. Provisional Patent Application Ser. No. 61/359,430, entitled "Lead Motion Sensing Using Cable Microphonics," filed on Jun. 29, 2010, which is hereby incorporated by reference herein in its entirety.

CROSS REFERENCE TO RELATED APPLICATIONS

This patent application is related to:
(1) U.S. patent application Ser. No. 13/168,481, published as US Publication No. 2011/0319779 A1;
(2) U.S. patent application Ser. No. 13/168,531, published as US Publication No. 2011/0319778 A1; and
(3) U.S. patent application Ser. No. 13/168,547, published as US Publication No. 2011/0319782 A1; all filed Jun. 24, 2011, each of which is hereby incorporated herein by reference in its respective entirety.

BACKGROUND

An ambulatory medical device, such as an implantable medical device (IMD), can be configured for implant in a subject, such as a patient. An IMD can be configured to be coupled to a patient's heart such as via one or more implantable leads. Such an IMD can obtain diagnostic information or generate therapy to be provided to the patient, such as via the coupled implantable lead. Examples of such devices can include cardiac function management (CFM) devices including one or more of implantable pacemakers, implantable cardioverter-defibrillators (ICDs), cardiac resynchronization therapy devices (CRTs), or one or more other devices. Such devices can include one or more electrodes coupled, such as via the implantable lead, to circuitry located on or within the IMD. Such circuitry can be configured to monitor electrical activity, such as to obtain information indicative of electrical activity of the heart.

A cardiac electrotherapy device to measure cardiac contractions using an elongated lead body that forms a high frequency transmission line is mentioned in U.S. Pat. No. 5,693,074 entitled "Cardiac Electrotherapy Device for Cardiac Contraction Measurement."

A time domain reflectometry impedance sensor for measuring body impedance along a lead or catheter implanted in a patient's cardiovascular system is mentioned in U.S. Pat. No. 5,361,776 entitled "Time Domain Reflectometer Impedance Sensor Method of Use and Implantable Cardiac Stimulator Using Same."

OVERVIEW

Generally, an IMD can obtain information indicative of cardiac activity such as by monitoring cardiac electrical signals. For example, such events can include heart chamber contractions such as corresponding to electrical depolarization or repolarizaiton of cells in cardiac muscle tissue. In an example, the IMD can determine indications of the subject's cardiovascular health such as using electrical signals obtained by a sensing circuit configured to obtain physiologic information (e.g., a blood pressure, a thoracic impedance indicative of respiration or fluid accumulation status, etc.). By obtaining such information, the IMD can monitor the effectiveness of a therapy (e.g., a pacing therapy, a cardiac resynchronization therapy, etc.), detect a change in cardiovascular health (e.g., detect myocardial ischemia, stroke volume, or cardiac output), or detect lead dislodgement.

In an example, the IMD can obtain electrical signals, such as an intracardiac electrogram to monitor the effectiveness of a delivered therapy. For example, an IMD can estimate whether a delivered electrostimulation pulse evoked a contractile response in cardiac tissue (e.g., "capturing" the cardiac tissue). For example, electrical depolarization information obtained from the monitored cardiac electrical signals can be used such as to detect whether a corresponding muscle contraction was evoked. However, such evoked response detection techniques can have limitations. A variety of issues can prevent detection of an evoked response using cardiac electrical activity, such as the presence of noise, myopotentials unrelated to cardiac contraction, beat-to-beat variation in signal morphology or amplitude, or other factors.

Cardiac electrical activity can be sensed for other purposes, such as for detection of fusion (e.g., detection of a simultaneous or near-simultaneous occurrence of an intrinsic contraction slightly before or during delivery of electrostimulation). In one approach, a QRS-width can be estimated using sensed cardiac electrical information. But, such an approach can have limitations, as a diseased heart may exhibit abnormal electrical activity confounding such analysis based exclusively on sensed electrical activity.

In an example, the IMD can monitor cardiac electrical signals for an indication of a change in cardiac health, such as due to myocardial ischemia or congestive heart failure. Myocardial ischemia generally refers to a reduction of blood supply to at least a portion of myocardial tissue of the heart. Detecting ischemia early can be important to minimizing risk to the patient, damage to the heart, and can also reduce health care costs. Myocardial tissue damaged due to ischemia can be more susceptible to abnormal heart rhythms, such as fibrillation, and can impair the pumping function of the heart. In one approach, cardiac electrical signals sensed using an implantable lead or via surface ECG can be used such as to detect ischemia, such as using information about a deviation of an ST segment. For example, myocardial ischemia can impair depolarization or repolarization of at least a portion of the heart, delaying activation of another portion of the heart resulting in longer ST intervals. Again, such techniques can have limitations as not all ischemic events cause a detectable change in electrically-indicated ST segment elevation or duration.

Generally, congestive heart failure (HF) occurs when the heart is unable to deliver enough blood to meet the metabolic demands of the body. For example, HF can reduce cardiac output, can cause an increase to venous blood pressures, or can cause abnormal nerve and hormone responses of the body, which can progressively worsen heart function. For example, HF can impair the heart's ability to eject blood with each heartbeat (e.g., causing a reduced "stroke volume"), or can reduce the overall amount of blood pumped by the heart (e.g., causing a reduced cardiac output). In an example, an IMD can monitor HF disease progression using information correlative to a sensed cardiac electrical signal, or obtained blood pressure information. For example, the IMD can estimate cardiac output (CO) or stroke volume (SV) using one or more of a left ventricular pressure, an aortic pressure, a rate of change of left ventricular pressure (e.g. dP/dt), or a signal indicative of left ventricular activity (e.g., a left ventricular electrogram).

An IMD can be configured to use one or more implantable leads such as to deliver therapy or sense a physiologic signal. However, the ability to deliver therapy or to obtain physiologic information can be degraded or inhibited entirely by lead dislodgment. In an example, an IMD can be configured to monitor for lead dislodgment such as by using information from a signal indicative of cardiac electrical activity (e.g., an electrogram). For example, information associated with cardiac electrical signal amplitude, timing, morphology, or noise level can be used as an indicator of lead dislodgement.

The present inventors have recognized, among other things, that mechanical information indicative of cardiac, blood, or vascular motion can be detected such as by using a motion of one or more conductors electrically coupled to an ambulatory device, such as an IMD. Such information can be used by the IMD in one or more of detecting a change to cardiovascular health, monitoring the effectiveness of a generated therapy, or guiding therapy. Information indicative of the motion of the implantable lead can be used, in addition to, or instead of sensed cardiac electrical activity.

For example, an implantable lead electrically and mechanically tethered to the IMD can provide information indicative of the motion of the lead, such as using one or more electrical measurements as described in the following examples. Such information indicative of the motion of the implantable lead can be used to adjust therapy parameters (e.g., one or more of therapy timing, a therapy delivery location, one or more therapy energy levels, etc.), or to obtain information about the effectiveness of a cardiac therapy (e.g., electrostimulation). Such monitored mechanical information can be used to obtain diagnostic information about one or more cardiac conditions or diseases. The present inventors have also recognized, among other things, that such information can be obtained via measurement of variation in electrical parameters correlative to the motion of one or more therapy-conducting or activity-sensing conductors located on or within the lead assembly, without requiring a dedicated mechanical or acceleration sensor incorporated into the lead assembly.

In an example, an implantable medical device can include a receiver circuit configured to be electrically coupled to conductor comprising a portion of an implantable lead and be configured to obtain information indicative of a movement of the implantable lead due at least in part to a motion of a heart. The device can include a processor circuit configured to determine whether a cardiac mechanical contraction occurred during a specified interval included in the obtained information indicative of the movement of the implantable lead. The processor circuit can be configured to determine information about the cardiac mechanical contraction using the obtained information indicative of the movement of the implantable lead.

Example 1 can include subject matter (such as a system, a method, a means for performing acts, or a machine-readable medium including instructions that, when performed by the machine, cause the machine to perform acts, etc.) that can include an implantable medical device (IMD) that can include a receiver circuit configured to be electrically coupled to a conductor comprising a portion of an implantable lead and to obtain information indicative of a movement of the implantable lead due at least in part to a motion of a heart. The IMD can include a processor circuit configured to determine one or more of (1) whether a cardiac mechanical contraction occurred during a specified interval included in the obtained information indicative of the movement of the implantable lead, or (2) information about the cardiac mechanical contraction using the obtained information indicative of the movement of the implantable lead.

In Example 2, the subject matter of Example 1 can optionally be configured such that the processor circuit can determine whether a cardiac mechanical contraction occurred during a specified interval included in the obtained information indicative of the movement of the implantable lead.

In Example 3, the subject matter of Examples 1 or 2 can optionally be configured such that the processor circuit can determine information about a cardiac mechanical contraction using the obtained information indicative of the movement of the implantable lead.

In Example 4 the subject matter of one or any combination of Examples 1-3 can optionally be configured such that that apparatus can include an implantable lead configured to be located within or near the heart, wherein the implantable lead can include a piezoelectric acoustic transducer configured to receive acoustic information indicative of the movement of the implantable lead, wherein the piezoelectric acoustic transducer can be coupled to the conductor included in the implantable lead.

In Example 5, the subject matter of one or any combination of Examples 1-4 can optionally include an excitation circuit configured to provide a non-tissue stimulating, non-therapeutic electrical excitation signal to the implantable lead, the signal comprising a time-varying signal including a first range of frequencies.

In Example 6, the subject matter of one or any combination of Examples 1-5 can optionally be configured such that the information indicative of the movement of the implantable lead can include one or more of magnitude information or phase information, corresponding to one or more frequencies included in the first range of frequencies, the magnitude information, or phase information, determined at least in part using an electrical response signal provided by the implantable lead in response to the excitation signal and the movement of the implantable lead.

In Example 7, the subject matter of one or any combination of Examples 1-6 can optionally be configured such that one or more of the magnitude information, or the phase information, includes a time-varying portion corresponding to the movement of the implantable lead.

In Example 8, the subject matter of one or any combination of Examples 1-7 can optionally be configured such that the processor circuit can determine information about the mechanical contraction via determining one or more of (1) an interval between two loci included in a mechanical contraction waveform, (2) an amplitude corresponding to a portion of the mechanical contraction waveform, or (3) information indicative of a rate of change of a portion of the mechanical contraction waveform, wherein the processor circuit can be configured to obtain the mechanical contraction waveform at least in part via filtering the information indicative of the movement of the implantable lead.

In Example 9, the subject matter of one or any combination of Examples 1-8 can optionally be configured such that the processor can determine the amplitude corresponding to a portion of the mechanical contraction waveform using one or more of a central tendency, a peak-to-peak determination, a peak determination, a root-mean-square determination, a statistical ranking, or an absolute value of at least a portion of the mechanical contraction waveform.

In Example 10, the subject matter of one or any combination of Examples 1-9 can optionally be configured such that the two loci can include a first locus corresponding to a feature at or near an initiation of a cardiac contraction on the mechanical contraction waveform, or a second locus corresponding to a feature at or near a peak of the mechanical contraction waveform.

In Example 11, the subject matter of one or any combination of Examples 1-10 can optionally include an electrostimulation therapy circuit configured to provide an electrostimulation therapy to the heart, wherein, in response to information about whether a cardiac mechanical contraction occurred, the processor circuit can be configured to automatically adjust one or more of an electrostimulation pulse width, an electrostimulation pulse amplitude, or a timing of delivery of electrostimulation therapy to be provided by the electrostimulation therapy circuit.

In Example 12, the subject matter of one or any combination of Examples 1-11 can optionally include an implantable lead configured to be located within or near the heart, and the implantable lead can include an electrode configured to provide one or more of electrostimulation to the heart or to sense cardiac electrical activity.

In Example 13, the subject matter of Example 12 can optionally include a first lead located within or near a first location of the heart, and a second lead located within or near a second location of the heart.

In Example 14, the subject matter of Example 13 can optionally be configured such that information indicative of a movement of the implantable lead can include a composite mechanical contraction waveform determined using a first mechanical contraction waveform obtained from the first lead and a second mechanical contraction waveform obtained from the second lead.

In Example 15, the subject matter of one or any combination of Examples 1-14 can optionally be configured to include a conductor, wherein the conductor can include one or more of a cardiac therapy delivery conductor or a cardiac electrical activity sensing conductor, and the conductor can be coupled to an implantable electrode included as a portion of the implantable lead.

Example 16 can include, or can be combined with the subject matter of one or any combination of Examples 1-15 to optionally include, subject matter (such as an apparatus, a method, a means for performing acts, or a machine-readable medium including instructions that, when performed by the machine, cause the machine to obtain information indicative of the movement of an implantable lead, wherein the lead can include a conductor electrically coupled to a receiver circuit that can be included as a portion of the IMD, and wherein the movement can be due at least in part to a motion of a heart, and to determine one or more of (1) whether a cardiac mechanical contraction occurred during a specified interval included in the obtained information indicative of the movement of the implantable lead, or (2) information about the cardiac mechanical contraction using the obtained information indicative of the movement of the implantable lead.

In Example 17, the subject matter of Example 16 can optionally include instructions that, when executed by the processor, cause the IMD to filter the information indicative of the movement of the implantable lead to obtain a mechanical contraction waveform.

In Example 18, the subject matter of Examples 16 or 17 can optionally include instructions that, when executed by the processor, cause the IMD to determine information about the mechanical contraction via determining one or more of (1) an interval between two loci included in the mechanical contraction waveform, (2) an amplitude corresponding to a portion of the mechanical contraction waveform, or (3) information indicative of a rate of change of a portion of the mechanical contraction waveform.

In Example 19, the subject matter of one or any combination of Examples 16-18 can optionally include instructions that, when executed by the processor, cause the IMD to determine the amplitude corresponding to a portion of the mechanical contraction waveform using one or more of a central tendency, a peak-to-peak determination, a peak determination, a root-mean-square determination, a statistical ranking, or an absolute value of at least a portion of the mechanical contraction waveform.

In Example 20, the subject matter of one or any combination of Examples 16-19 can be configured such that the two loci include a first locus corresponding to a feature at or near initiation of a cardiac contraction on the mechanical contraction waveform, or a second locus corresponding to a feature at or near a peak of the mechanical contraction waveform.

In Example 21, the subject matter of one or any combination of Examples 16-20 can optionally include instructions that, when executed by the processor, cause the IMD to automatically adjust one or more of an electrostimulation pulse width, an electrostimulation pulse amplitude, or a timing of delivery of electrostimulation therapy to be provided by the electrostimulation therapy circuit, in response to the determination of whether a cardiac mechanical contraction occurred.

Example 22 can include subject matter, or can be combined with the subject matter of one or any combination of Examples 1-21, (such as a system, a method, a means for performing acts, or a machine-readable medium including instructions that, when performed by the machine, cause the machine to perform acts, etc.) that can include a means of obtaining information indicative of the movement of an implantable lead, the implantable lead including a conductor electrically coupled to a receiver circuit, the receiver circuit included as a portion of the IMD, and the movement due at least in part to a motion of a heart; and a means of determining one or more of (1) whether a cardiac mechanical contraction occurred during a specified interval included in the obtained information indicative of the movement of the implantable lead, or (2) information about the cardiac mechanical contraction using the obtained information indicative of the movement of the implantable lead.

In Example 23, the subject matter of Example 22 can include subject matter that can include a means of automatically adjusting one or more of an electrostimulation pulse width, an electrostimulation pulse amplitude, or a timing of delivery of electrostimulation therapy to be provided by the electrostimulation therapy circuit, in response to information about whether a cardiac mechanical contraction occurred.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
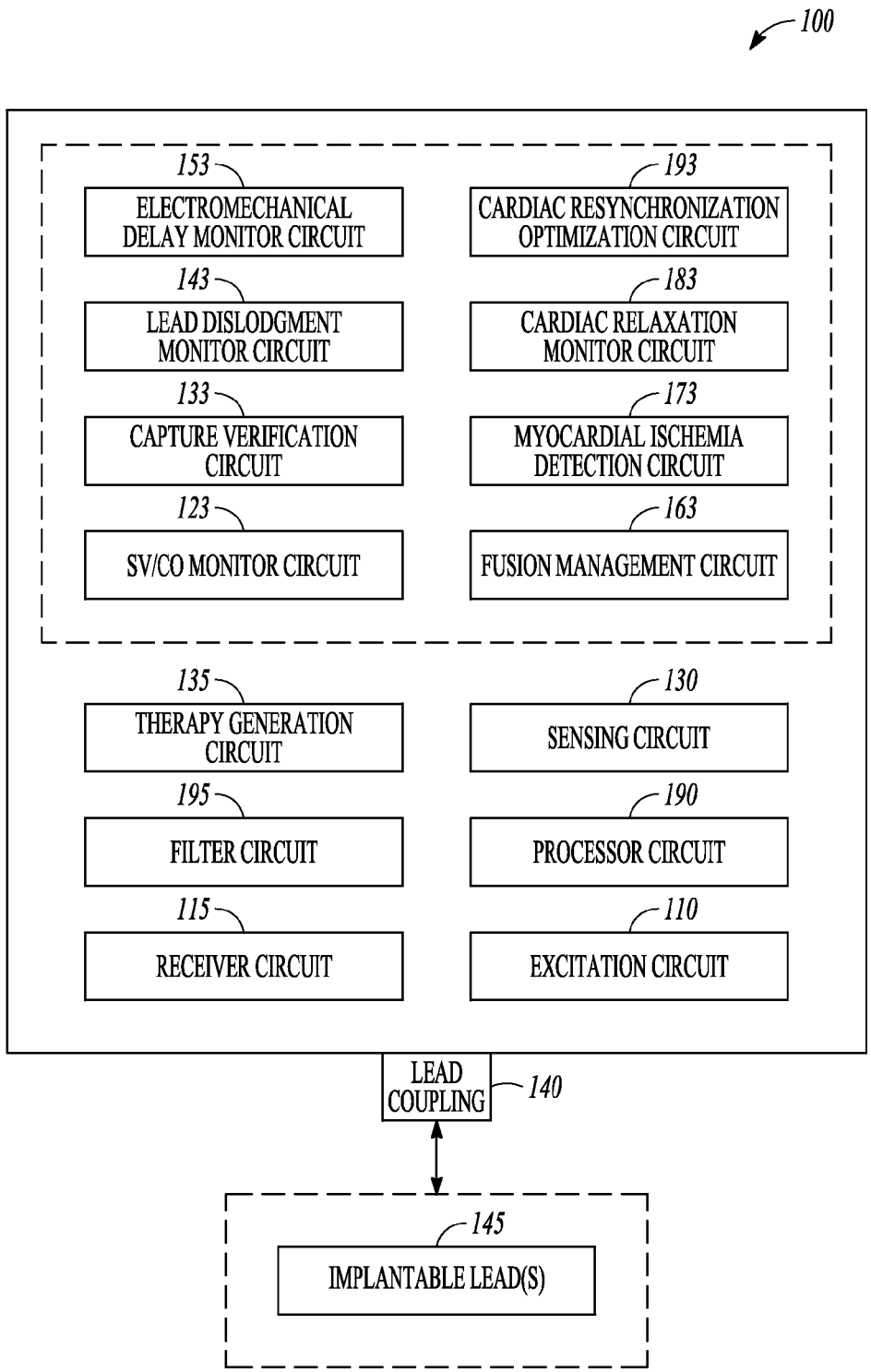
FIG. 1 illustrates generally an example of a portion of an ambulatory system for analyzing information indicative of the movement of an implantable lead.

FIG. 1 illustrates generally an example of a portion of an ambulatory system 100 that can be used for analyzing information indicative of the movement of an implantable lead. The ambulatory system 100 can include an ambulatory medical device, such as the implantable medical device (IMD) 105 that can include an excitation circuit 110, a receiver circuit 115, a sensing circuit 130, a therapy delivery circuit 135, a processor circuit 190, and a filter circuit 195. In an example, the IMD 105 can include an interconnection, such as the lead coupling 140, configured to electrically couple the IMD 105 to one or more implantable leads, such as the implantable lead 145. In an example, the processor circuit 190 can perform instructions corresponding functions of, or include one or more of, a stroke volume or cardiac output (SV/CO) monitor circuit 123, a capture verification circuit 133, a lead dislodgment monitor circuit 143, a electromechanical delay monitor circuit 153, a fusion management circuit 163, a myocardial ischemia detection circuit 173, a cardiac relaxation monitor circuit 183, or a cardiac resynchronization optimization circuit 193, such as discussed in the examples of FIG. 9.

One or more of the excitation circuit 110, the receiver circuit 115, the sensing circuit 130, the therapy delivery circuit 135, the processor circuit 190, the filter circuit 195, the SV/CO monitor circuit 123, the capture verification circuit 133, the lead dislodgment monitor circuit 143, the electromechanical delay monitor circuit 153, the fusion management circuit 163, the myocardial ischemia detection circuit 173, the cardiac relaxation monitor circuit 183, or the cardiac resynchronization optimization circuit 193 can be realized on or within a commonly shared substrate, such as on a commonly-shared integrated circuit, module, circuit board, or the like. In an example, one or more of the circuits of FIG. 1 can be included in one or more separate assemblies or separate ambulatory devices, such as using one or more wired or wireless communication techniques to exchange information between such devices.

The IMD 105 can include processing capability, such as the processor circuit 190. Various circuits, functions, or techniques described in the examples described above and below can be implemented, such as using an application-specific integrated circuit (ASIC) configured to perform one or more functions, or a general-purpose circuit programmed to perform such functions. Such a general-purpose circuit can include a microprocessor, a microcontroller, or a programmable logic circuit, or a portion of one or more of these. In an example, the IMD can include a processor-readable medium such as a memory circuit (e.g., an EEPROM, an SRAM, or one or more other memory technology devices), and the processor circuit 190 can be configured to perform one or more instructions stored on the processor-readable medium.

In an example, the IMD 105 can include an excitation circuit, such as the excitation circuit 110 that can be coupled to at least one of the receiver circuit 115 or the implantable lead 145. The excitation circuit 110 can be configured to provide a time varying signal including a first range of frequencies such as including a non-tissue stimulating, non-therapeutic electrical excitation signal, such as to the implantable lead 145. In an example, the excitation signal can include a time-varying voltage or current including one or more frequencies within a specified frequency range (e.g., a range from about 10 KHz to about 5 MHz, or from about 5 MHz to about 30 MHz, from about 30 MHz to about 150 MHz, or including one or more other ranges of frequencies). In an example, the excitation signal can include a pulsed electrical signal, such as including one or more current or voltage pulses including a specified or desired amplitude, duration, pulse repetition rate, duty cycle, or morphology, among other parameters.

In an example, the excitation circuit 110 can be coupled to one or more implantable leads, such as the implantable lead 145 via the lead coupling 140. The lead coupling 140 can include a header or other connector included as a portion, part, or component of the IMD 105. In an example, an impedance measurement can be made at least in part using the excitation circuit 110, such as to obtain the information indicative of lead motion. The impedance measurement can include injecting a current between a first terminal such as at least a portion of the lead coupling 140 and one or more other conductive elements, such as the housing of the IMD 105, or a second terminal, and measuring the voltage developed across the respective conductive elements. In an example, a synchronous current injection and voltage measurement can be used, such as discussed in relation to the physiologic impedance measurement techniques of the commonly assigned U.S. patent application Ser. No. 12/350,728, entitled "IMPEDANCE MEASUREMENT AND DEMODULATION USING IMPLANTABLE DEVICE," filed on Jan. 8, 2009, published as US Publication No. 2009/1777119 A1 which is herein incorporated by reference in its entirety, including its description of injecting one or more non-tissue-stimulating bi-phasic current pulses and synchronously measuring the voltage induced by the one or more bi-phasic current pulses.

In an example, the implantable lead 145 can be coupled to circuitry within the IMD 105 such as via the lead coupling 140 (e.g., a header or other connector block included as a portion of the IMD 105). For example, the implantable lead 145 can include one or more conductors (e.g., cardiac therapy delivery conductor, a cardiac electrical activity sensing conductor, etc.), such that can provide electrical coupling between one or more electrodes located at or near tissue (e.g., cardiac tissue, neural tissue, etc.) and the IMD 105. In an example, the implantable lead 145 can be located at a site within or on the body (e.g., including one or more surface, subcutaneous, or intravascularly-located electrodes or conductors).

In an example, the receiver circuit 115 can be electrically or communicatively coupled to one or more implantable leads, such as the implantable lead 145, such as through the lead coupling 140. For example, one or more separate conductors in the implantable lead 145 can be attached to one or more terminal blocks such as included in a lead coupling 140 such as attached to a housing of the IMD 105. For example, the lead coupling 140 can provide electrical contact between one or more conductors of the implantable lead 145 and circuitry within the IMD 105 (e.g., excitation circuit 110, the receiver circuit 115, the therapy generation circuit 135, etc.). In an example, the receiver circuit 115 can be configured to receive a response signal, such as including a signal indicative of the motion of the implantable lead, hereinafter referred to as a lead motion indicating (LMI) signal. For example, a response signal can be obtained in response to an interaction between an excitation signal, such as provided by the excitation circuit 110, and the electrical characteristics of the implantable lead 145 (e.g., one or more motion-dependent passive electrical characteristics of the lead) such as during a movement of the implantable lead 145. For example, such electrical characteristics of the lead can vary as portions of the lead are compressed or flexed, such as altering the spacing between portions of one or more conductors included in the lead assembly.

In an example, the receiver circuit 115 can be configured to receive or process one or more response signals obtained from one or more implantable leads 145 concurrently with or subsequently to the excitation circuit 110 providing the excitation signal to the one or more implantable leads. For example, the receiver circuit can be configured to receive magnitude information or phase information corresponding to one or more frequencies included in a range of frequencies provided in the excitation signal. In an example, the magnitude information or the phase information can include time-varying information that can include information indicative of the movement of the implantable lead 145.

For example, the receiver circuit 115 can be configured to obtain information about the movement of a first implantable lead located (e.g., a first LMI signal), such as located within or near a first location of the heart using a first response signal obtained from the first implantable lead. Additionally, the receiver circuit 115 can be configured to obtain information about the movement of a second implantable lead (e.g., a second LMI signal), such as located within or near a second location of the heart, using a second response signal obtained from the second implantable lead. For example, the information about the movement of an implantable lead can be determined or provided from the LMI signal (e.g., using information about an amplitude, a frequency, a phase, a noise floor, a signal-to-noise ratio, a duration between peaks or other features, a waveform morphology or shape, or one or more other characteristics of the LMI signal).

In an example, the receiver circuit 115 can be configured to process the response signal (e.g., using a filter), such as to provide a time-varying signal indicative of the motion of the implantable lead (e.g., the LMI signal) for analysis. For example, the response signal can include a first component (e.g., a carrier signal), such as including information about the excitation signal, and a second component (e.g., a signal indicative of lead motion that can modulate the carrier), such as the LMI signal. In an example, the LMI signal can include time-varying information indicative of the motion of the implantable lead. In an example, the receiver circuit 115 can be configured to transfer at least a portion of the LMI signal to a circuit configured for signal processing (e.g., processor circuit 190, etc.) to be analyzed. For example, the processor circuit 190 can analyze at least a portion of the LMI signal such as to obtain information indicative of the motion of the implantable lead such that can contain information about a cardiac mechanical contraction (e.g., a mechanical contraction waveform).

In an example, the receiver circuit 115 can be configured to determine amplitude information of one or more LMI signals. For example, the amplitude information can be determined such as by using one or more of a central tendency (e.g., an average, a median, a mean, etc.), a peak-to-peak determination, a peak determination, a root-mean-square determination, a relative indication of information about a portion of the LMI signal (e.g., a percentage of an absolute or local maximum or minimum), or an absolute value of at least a portion of the LMI signal. In an example, the receiver circuit 115 can be configured to analyze at least a portion of the LMI signal, such as to compare amplitude information obtained from the LMI signal to a criterion (e.g., a threshold) or to amplitude information corresponding to a second LMI signal.

In an example, the IMD 105 can include a filter circuit 195 such as can be communicatively coupled to one or more of the receiver circuit 115 or the processor circuit 190. In an example, the filter circuit 195 can be configured to provide an LMI waveform representative of a mechanical contraction. For example, the filter circuit 195 can provide the LMI waveform such as by using band-pass filter over a specified frequency range (e.g., from about 0.5 Hz to about 2 Hz, near 10 Hz, etc.). The provided mechanical contraction waveform can be conditioned such that the waveform has a zero average over long intervals or can approach zero during an interval of no motion. Although band-pass filters are generally described, any combination of analog or digital filters can be used, including one or more high pass filters, low pass filters, notch filters, passive filters (e.g., having "T" sections, "π" sections, "L" sections, etc.), active filters (e.g., Bessel filter, Chebyshev filter, Butterworth filter, etc.), IIR filters, FIR filters, or the like.

In an example, the IMD 105 can include a processor circuit 190 configured to be communicatively coupled to one or more of the excitation circuit 110, the receiver circuit 115, the sensing circuit 130, the therapy delivery circuit 135, or the filter circuit 195. In an example, the processor circuit 190 can be configured to receive information indicative of the motion of an implantable lead, such as an LMI signal, from one or more of the receiver circuit 115 or the filter circuit 195. In an example, the processor circuit 190 can be configured to determine whether a cardiac mechanical contraction occurred during a specified interval, such as included in at least a portion of the LMI signal, such as a mechanical cardiac waveform.

Movement of the implantable lead 145 can include a physical displacement of one or more portions of the implantable lead 145, such as with respect to an equilibrium position. In an illustrative example, the implantable lead 145 can undergo a physical displacement, such as from a mechanical coupling to, or physical contact with, moving tissue. In an example, the information indicative of movement of the implantable lead 145 can include a time varying signal (e.g., a LMI signal), where the LMI signal corresponds to a movement of the heart (e.g., a cardiac contraction cycle, an impact of a heart valve to the implantable lead 145, a frictional contact of cardiac tissue to the implantable lead 145, or mechanical contact of the lead to vibrating tissue, etc.).

In an example, the processor circuit 190 can be configured to obtain the mechanical contraction waveform at least in part using one or more filters, such as using the filter circuit 195. For example, the response signal, such as obtained by the receiver circuit 115, can be filtered using a band-pass filter configured to pass frequencies within a specified frequency range, such as between about 0.05 Hz and about 10 Hz, such as discussed below with FIG. 8. In an example, the filtered signal (e.g., the LMI signal) can include a waveform indicative of one or more cardiac mechanical contractions, such as a mechanical contraction waveform. In an example, the processor circuit 190 can be configured to analyze the mechanical contraction waveform continuously. In an example, the processor circuit 190 can be configured to analyze a specified duration of lead motion information including one or more mechanical contractions, such as during a specified duration of contraction information obtained at a specified time (e.g., once a minute, hourly, daily, weekly, or during one or more other times), or obtained following a specified event (e.g., a user initiated event, the occurrence of a physiological event, or in response to one or more other criteria).

In an example, the processor circuit 190 can be configured such as to obtain a mechanical contraction waveform corresponding to the mechanical motion of at least a portion of a heart (e.g., one or more of the right atrium, left atrium, right ventricle, or left ventricle). For example, the implantable lead 145 can be located within or near the right atrium (e.g., an atrial lead), where the motion of the implantable lead 145 can correspond primarily to the motion of the atrium during a mechanical contraction. In an example, the processor circuit 190 can be configured such as to obtain a mechanical contraction waveform corresponding to at least the mechanical contraction of a ventricle. For example, an implantable lead 145 can be implanted within or near a ventricle (e.g., within the right ventricle, within a coronary vein near the left ventricle, etc.) such as where the motion of the implantable lead 145 can correspond primarily to a mechanical contraction of the ventricle. In an example, the motion of the implantable lead 145 can include information about the motion of one or more portions of the heart. For example, the implantable lead 145 such as implanted in the right ventricle can pass through the right atrium and the mitral valve. Such placement can result in movement of the implantable lead caused by at least one of the right ventricle, the right atrium, or the mitral valve. Such a mechanical contraction waveform can include information about the mechanical motion of one or more portions of the heart.

For example, a portion of the mechanical contraction waveform, such as obtained from an implantable lead 145 located in the right ventricle, can include information corresponding to an atrial contraction (e.g., a peak, or a displacement), or a ventricular contraction (e.g., a peak of larger magnitude, or a larger displacement, such as compared to information corresponding to the atrial contraction).

In an example, the processor circuit 190 can generate a composite mechanical contraction waveform, such as by using a mixer circuit. Such composite mechanical contraction waveforms can include information about atrial motion, ventricular motion, motion of the implantable lead independent of the motion of the heart, or valve impacts. For example, the mixer circuit can combine one or more mechanical contraction waveforms additively, such as to provide a composite mechanical contraction waveform having information about atrial and ventricular contractions. In an example, the mixer circuit can be configured to combine at least a portion of two or more mechanical contraction waveforms such as to provide a mechanical contraction waveform primarily associated with ventricular motion or primarily associated with atrial motion In an example, the processor circuit 190 can be configured to determine information about one or more mechanical contractions of the heart such as using by using the mechanical contraction waveform. For example, the processor circuit 190 can be configured to use the mechanical contraction waveform information such as to determine at least one of (1) interval information (e.g., an interval between two loci included in the mechanical contraction waveform), (2) amplitude information (e.g., an amplitude corresponding to a portion of the mechanical contraction waveform), or (3) rate of change information (e.g., a rate of change of a magnitude over a portion of the mechanical contraction waveform).

In an example, the processor circuit 190 can be configured to obtain interval information of the mechanical contraction of the heart, such as including an interval between two loci included in a mechanical contraction waveform. For example, a first locus can include a locus corresponding to a feature at or near the initiation of a cardiac contraction, such as indicated on the mechanical contraction waveform. A second locus can include a locus corresponding to a feature at or near a peak of the mechanical contraction waveform. In an example, the interval information can include a duration associated with the contraction of the myocardium. The interval information between a locus at or near the initiation of a cardiac contraction and a second locus near the peak of the mechanical contraction waveform can include information about the health of the heart (e.g., the strength, forcefulness, or speed of a mechanical contraction). For example, a shorter duration between the initiation of a contraction and the peak value can be associated with a ventricular beat synchronized with an atrial beat. In an example, the interval information can include an interval between loci associated with successive or adjacent cardiac contractions such as included in a mechanical contraction waveform. For example, the interval information can include the interval between two successive or adjacent peaks on a mechanical contraction waveform, such as indicative of a heart rate or rhythm (e.g., such as for use in detection or classification of an arrhythmia).

In an example, the processor circuit 190 can be configured to obtain interval information between a locus on a first mechanical contraction waveform (e.g., obtained from a first implantable lead), and a locus on a second mechanical contraction waveform (e.g., obtained from a second implantable lead or obtained over a previous duration from either the first or second implantable lead). For example, a first mechanical contraction waveform, such as from an implantable lead 145 located in an atrium, can include information such as corresponding to at least an atrial contraction. A second mechanical contraction waveform, such as obtained from an implantable lead 145 located in or near a ventricle, can include information corresponding to at least a ventricular contraction. In an example, the processor circuit 190 can be configured to obtain interval information such as from between a feature (e.g., a locus at or near a peak indicative of an atrial contraction) on the first mechanical contraction waveform and a feature (e.g., a locus at or near the peak indicative of a ventricular contraction) on the second mechanical contraction waveform. Such interval information can be processed by the processor circuit 190 such as to determine information associated with cardiac synchrony (e.g., atrio-ventricular synchrony), or to adjust a therapy (e.g., CRT therapy), such as by one or more of adjusting or monitoring an atrio-ventricular delay (AVD).

In an example, the processor circuit 190 can be configured to obtain information about the mechanical contraction of the heart, such as including an amplitude corresponding to a portion of the mechanical contraction waveform. In an example, the processor circuit 190 can be configured to determine such amplitude information by using one or more of a central tendency (e.g., an average, a median, a mean, etc.), a peak-to-peak determination, a peak determination, a root-mean-square determination, a relative indication of information about a portion of the LMI signal such as a percentage of an absolute or local maximum or minimum or an absolute value of at least a portion of the mechanical contraction waveform. In an example, amplitude information, such as peak information, can correspond to a contracted state of the heart. In an example, an amplitude value of about zero (or another specified baseline), such as obtained from a filtered mechanical contraction waveform, can correspond to an "uncontracted" state of the heart such as during repolarization. For example, the processor circuit can determine a degree of cardiac contraction forcefulness or health such as by using the amplitude information, where larger amplitudes can be associated with greater contraction forcefulness.

In an example, the processor circuit 190 can be configured such as to determine a physiological condition or provide a therapy such as by using the amplitude information. For example, the processor circuit 190 can determine an energy or power corresponding to a portion of the mechanical contraction waveform, such as can be associated with stroke volume or cardiac output (e.g., via estimating an area under a curve formed by the mechanical contraction waveform, or via summing the square of successive waveform samples and then determining a square root of the sum, etc.).

In an example, the processor circuit can be configured to compare amplitude information of sampled mechanical contraction waveforms between each other, such as to detect a change in cardiac physiological status. For example, first amplitude information corresponding to a portion of the mechanical contraction waveform can be associated with a normal sinus rhythm (e.g., a baseline), and second amplitude information can correspond to an arrhythmic or unknown mechanical contraction waveform. The processor circuit 190 can use such first and second amplitude information such as to detect a morphology change such as can be indicative of an arrhythmia, an onset of myocardial ischemia, lead dislodgement, or one or more other conditions.

In an example, the processor circuit 190 can be configured to obtain information indicative of a rate of change over a portion of a mechanical contraction waveform, such as during a transition between a contracted state and an un-contracted state. For example, rate of change information (e.g., from about 10% to about 90%, or from about 90% to about 10% of a peak value) can provide an indication of cardiac efficiency. In an example, rate of change information can be obtained from a portion of a mechanical contraction waveform, such as between a loci associated with an "uncontracted" state (e.g., near zero), to a loci associated with a contracted state (e.g., at or near a peak), or vice versa. For example, rate of change information such as obtained between a first locus, such as at or near the peak of a mechanical contraction waveform, to a second locus, such as at or near a baseline (or near zero) amplitude portion, can be indicative of impaired ability of the heart to relax.

In an example, the IMD 105 can include the sensing circuit 130, such as to obtain a signal indicative of cardiac electrical activity. For example, the obtained signal can be used to provide a graphical representation of the cardiac electrical activity, such as an intracardiac electrogram. In an example, the IMD 105 can be configured to detect a cardiac condition (e.g. an arrhythmia) or therapy effectiveness (e.g., cardiac capture following a pacing pulse), such as using signal information (e.g., magnitude or interval information) detected using the sensing circuit 130, such as magnitude or interval information from the signal representative of cardiac electrical activity. For example, the processor circuit 190 can be configured to use electrogram timing information, such as a time interval between successive atrial contractions, ventricular contractions, or between an atrial contraction and a ventricular contraction.

In an example, the timing information can be compared to a criterion, such as to detect or classify an arrhythmia when the criterion has been met (e.g., exceeding a threshold). In an example, the criterion can vary based on one or more physiological conditions, such as can be detected using the signal information (e.g., a magnitude or timing information of a signal indicative of cardiac electrical activity). For example, the criterion can vary using automatic gain control such as to modify a threshold following a sensed beat. In an example, the arrhythmia detection circuit 120 can be configured to use the LMI signal to confirm an arrhythmia condition diagnosis, such as to avoid delivering inappropriate therapy In an example, the IMD 105 can be configured to generate an electrostimulation, such as using one or more of a pacing or a cardiac resynchronization therapy (CRT) circuit (e.g., the therapy generation circuit 135). Such a therapy generation circuit 135 can be configured to generate bradycardia pacing or a resynchronization electrostimulation therapy for delivery to cardiac tissue, or one or more other therapies. In an example, the therapy generation circuit 135 can include a neural stimulator device, such as to provide electrical, mechanical, optical, acoustic or chemical stimulation to one or more neural targets.

In an example, the therapy generation circuit 135 can include one or more of: a pacing circuit, an anti-tachyarrhythmia therapy circuit, a cardiac resynchronization therapy circuit, a cardiac contractility modulation (CCM) circuit, or one or more other therapy generation circuits. For example, the anti-tachyarrhythmia therapy circuit can include a defibrillation circuit, or an anti-tachyarrhythmia pacing (ATP) circuit, or the like. In an example, the therapy generation circuit 135 can be configured to determine a therapy, or therapy protocol, such as to guide an arrhythmia therapy.

In an example, the therapy generation circuit 135 can be configured to withhold generation of a therapy such as when an arrhythmia condition is not present. In an example, the therapy generation circuit 135 can be configured to withhold, or delay, generation of an arrhythmia therapy, such as when a rhythm, such as a detected arrhythmia, has been determined to be supraventricular in origin.

In an example, the therapy generation circuit 135, or the processor circuit 190, can be configured to automatically adjust one or more of an electrostimulation pulse width, an electrostimulation pulse amplitude, or a timing of delivery of electrostimulation therapy. Such adjustment can occur in response to information about whether a cardiac mechanical contraction occurred. For example, the processor circuit 190 can be configured to monitor the mechanical contraction waveform after the therapy generation circuit 135 generating a therapy to the heart (e.g., pacing energy). In response to information obtained while monitoring the therapy, the processor circuit 190 can determine information corresponding to the effectiveness of the delivered therapy (e.g., captured the myocardium, achieved fusion or another specified timing relationship between paced ventricular activation relative to an intrinsic atrial beat, or improved cardiac synchrony via CRT).

Figure 2:
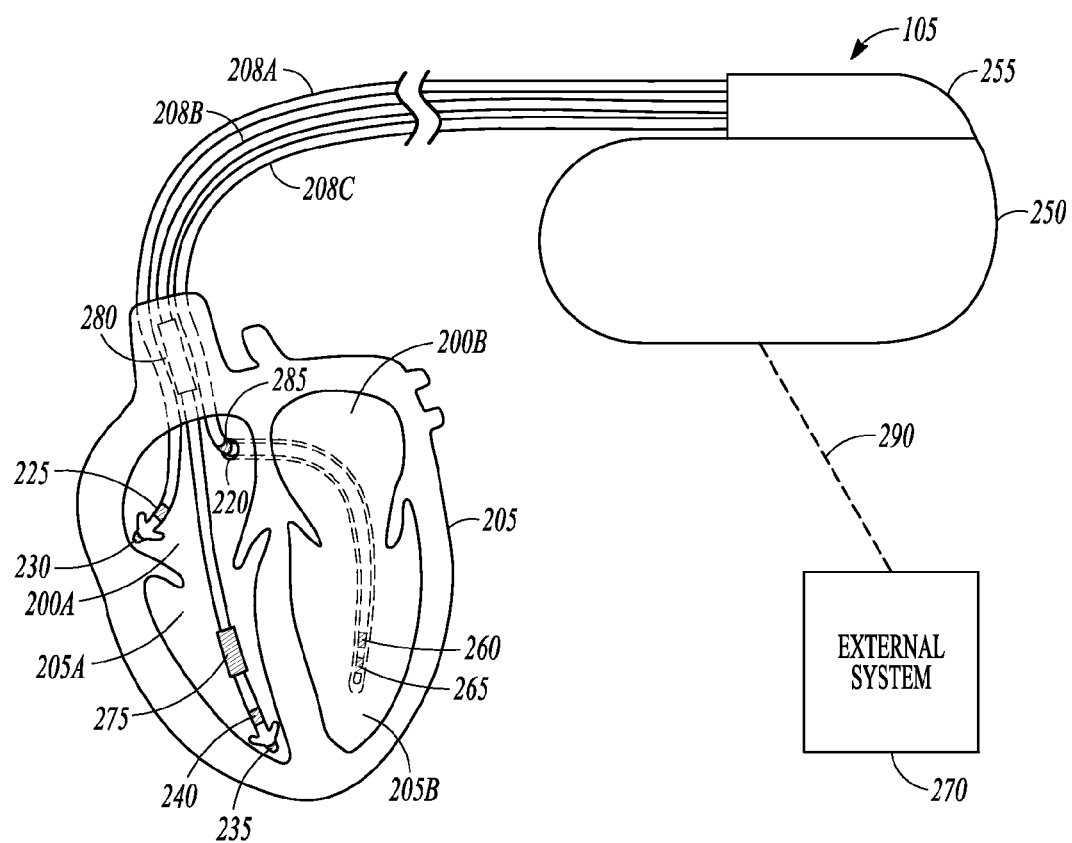
FIG. 2 illustrates generally a portion of a system that can include an implantable medical device.

FIG. 2 illustrates generally a portion of a system that can include an IMD 105. Examples of the IMD 105 can include cardiac function management (CFM) devices such as including one or more of implantable pacemakers, implantable cardioverter-defibrillators (ICDs), cardiac resynchronization therapy devices (CRTs), or one or more other devices. The system can include an IMD programmer or other external device 270, such as a local monitoring device, capable of communicating wirelessly, such as via wireless communication using a communicative coupling 290 with the IMD 105, using a communication or computer network, radio frequency (RF) signals, or other telemetry capabilities. In an example, a remote monitoring device can be communicatively coupled, such as via a communication or computer network, to a remote monitoring device, such as at a location different from the local monitoring device (e.g., a central server, a remotely-located caregiver workstation, etc.).

The IMD 105 can be coupled via one or more leads 208A-C to the heart 205. Cardiac leads 208A-C (e.g., the implantable lead 145) can include a proximal end coupled to the IMD 105 and a distal end, capable of being electrically coupled by one or more electrodes to one or more portions of the heart 205. The electrodes can deliver cardioversion, defibrillation, pacing, or resynchronization therapy, or combinations thereof, such as from the therapy generation circuit 135, to one or more chamber of the heart 205. The electrodes can be electrically coupled to sense amplifiers configured to receive electrical signals indicative of cardiac activity, such as the sensing circuit 130.

The heart 205 includes a right atrium 200A, a left atrium 200B, a right ventricle 205A, a left ventricle 205B, and a coronary sinus 220 extending from right atrium 200A. The atrial lead 208A can include electrodes (e.g., electrical contacts, such as a ring electrode 225, and a tip electrode 230, etc.) capable of being disposed in the atrium 100A of the heart 205, such as for sensing signals, delivering pacing therapy, or both, to the atrium 200A.

The ventricular lead 208B can include one or more electrodes, such as the tip electrode 235 and the ring electrode 240, such as for sensing signals, delivering pacing therapy, or both. The lead 208B can include additional electrodes, such as for delivering atrial cardioversion, atrial defibrillation, ventricular cardioversion, ventricular defibrillation, or combinations thereof to the heart 205. Such electrodes can have larger surface areas than do pacing electrodes, such as to handle larger energies involved in defibrillation. In an example, the lead 208B can deliver resynchronization therapy to the heart 205.

The IMD 105 can include a third cardiac lead 208C capable of being attached to the IMD 105 through the header 255. The third cardiac lead 208C can include one or more electrodes such as electrodes 260 and 265, such as placed in a coronary vein nearby the left ventricle (LV) 205B. The third cardiac lead 208C can include a ring electrode 285, such as positioned near the coronary sinus (CS) 220.

The lead 208B can include one or more of a first defibrillation coil electrode 275, such as located proximal to the tip and ring electrodes 235, 240, such as for placement in a right ventricle (RV), or a second defibrillation coil electrode 280, such as located proximal to the first defibrillation coil 275, the tip electrode 235, and the ring electrode 240, such as for placement in or near the superior vena cava (SVC). In an example, a cardioversion or a shock therapy can be delivered from the first coil (e.g., the RV coil 275) to the second coil (e.g., the SVC coil 280). In an example, the SVC coil 280 can be electrically tied to an electrode formed on a hermetically-sealed IMD housing 250 ("can"), such as to provide an adjustable defibrillation "vector" or "pathway" for energy to pass between the RV coil 275 and the housing 250 via the myocardium. In an example, the therapy can be delivered from the RV coil 275, such as only to the electrode formed on the IMD can 250. The present methods and systems can be adjustably configured to provide one or more pacing or defibrillation therapies across specified electrode configurations, such as using information about electrical or mechanical cardiac activity as described in the examples above and below.

Figure 3:
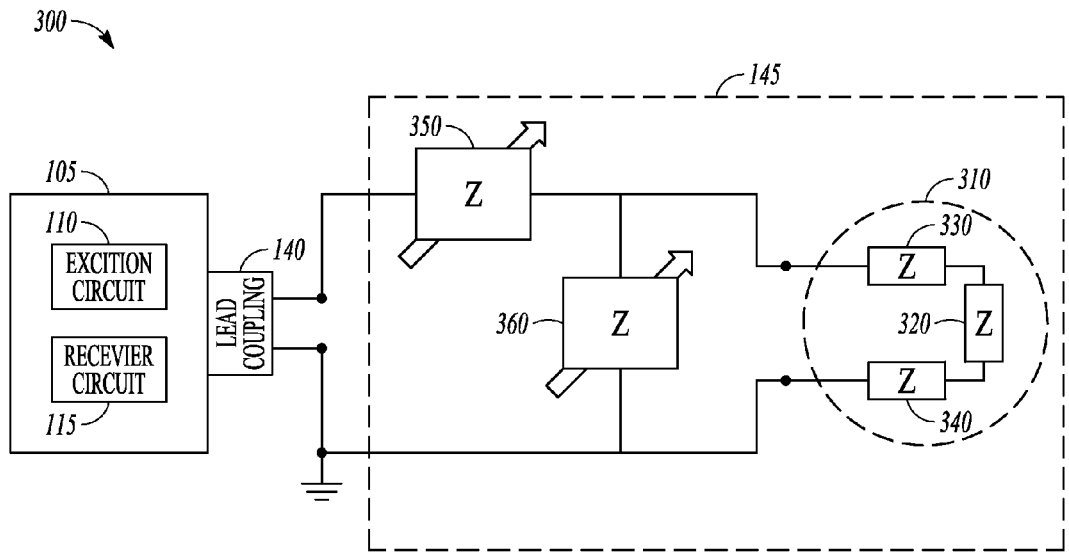
FIG. 3 illustrates generally a portion of a system that can include detecting information indicative of the movement of the implantable lead.

FIG. 3 illustrates generally a portion of a system 300 that can include detecting information indicative of the movement of one or more implantable leads, such as the implantable lead 145. In an example, the system 300 can include an IMD 105, and the implantable lead 145, such as configured to provide a therapy (e.g., an arrhythmia therapy) to a heart 205, to sense a physiological signal associated with a subject (e.g., an electrogram), or both. In an example, the IMD 105 can include the excitation circuit 110 and the receiver circuit 115, and the lead coupling 140 as described above. In an example, the implantable lead 145 can be configured to be implanted within a subject such that a distal end of the lead body 310 can be located within or near the heart 205 (e.g., at a tissue interface location), and a proximal end can be configured to be electrically coupled to the IMD 105 (e.g., at the lead coupling 140), such as to provide a therapy, to sense a physiological signal, or both. In an example, the excitation circuit 110 can be configured to provide an excitation signal to the implantable lead 145. Such an excitation signal can interact with the electrical characteristics of the implantable lead such as to provide a response signal, as can be obtained by the receiver circuit 115.

In an example, the implantable lead 145 can include one or more conductors (e.g., filers), such as one or more filers that spiral or otherwise traverse the length of the lead, such as from a connector at the proximal end of the lead to one or more electrodes along the lead or near the distal end. In an example, a lead body can be represented as a combination of resistive, capacitive, and inductive elements. In an example, the electrical characteristics of the implantable lead can be represented, such as using lead body impedance (e.g., lead impedance 350-360) and the distal end of the lead can be modeled, such as using one or more of an electrode impedance 330-340, a cardiac tissue interface impedance 320, or the like. In an example, the impedance 330-360 can represent the electrical characteristics of various lead portions (e.g., passive electrical characteristics such as the resistance of a filer, an inductance of a loop formed by one or more filers, a capacitance between one or more filers, etc.) over a specified frequency range. In an example, the tissue interface impedance can include electrode impedance, such as a characteristic impedance of an electrode, and an impedance 320 at the tissue interface, such as an impedance corresponding to a connection of the implantable lead to the cardiac tissue.

In an example, the impedances 320-360 can vary over a specified frequency range (e.g., from about 10 KHz to about 30 MHz, from about 30 MHz to about 150 MHz, etc.), corresponding to one or more of capacitive or inductive coupling between two or more portions of the implantable lead 145. In an example, an implantable lead can include an active element, such as an accelerometer, or piezoelectric elements, that can be used to obtain information about the motion of the implantable lead 145 separately from, or additionally to the passive electric characteristics.

Figure 6:
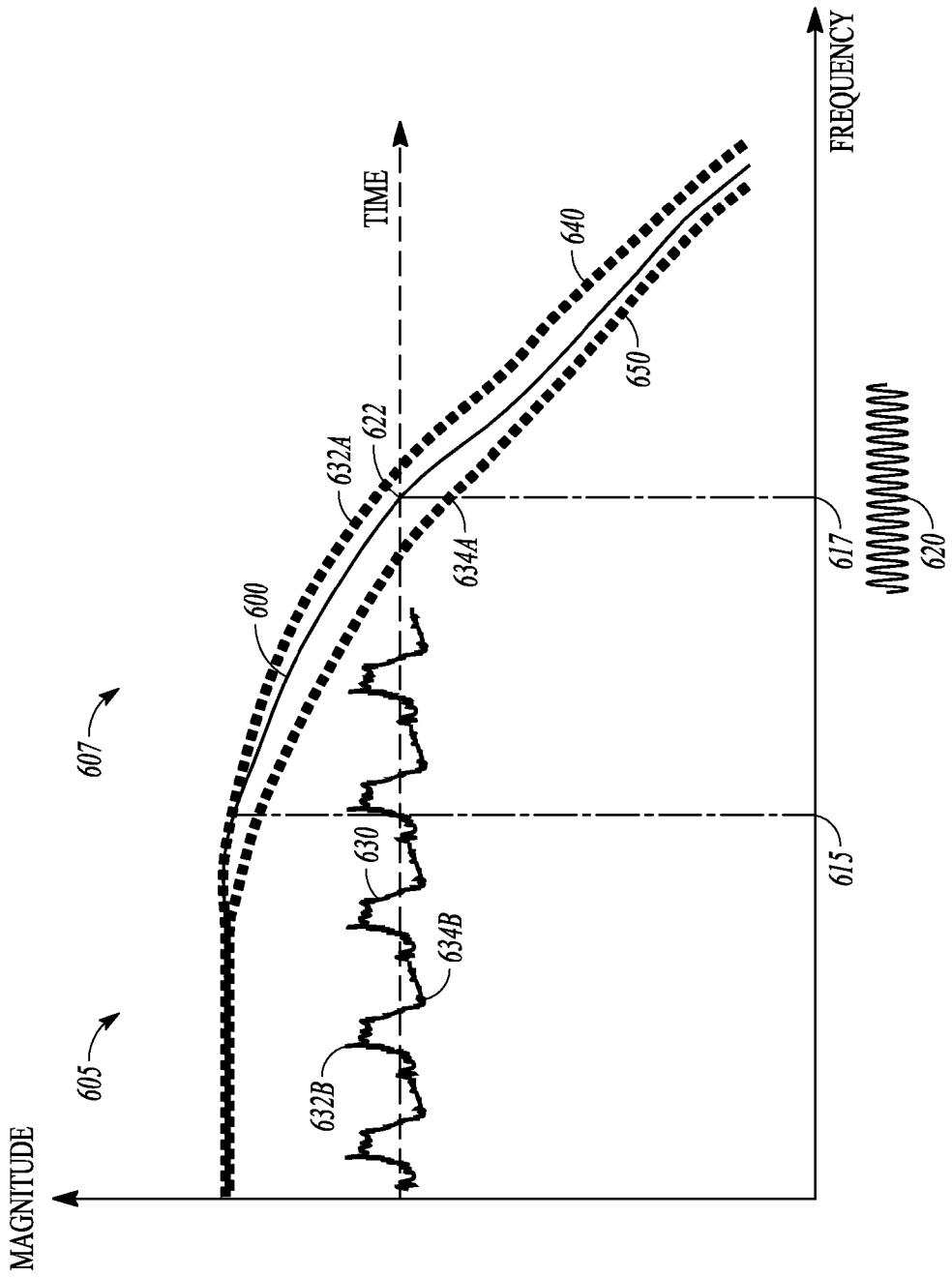
FIG. 6 illustrates generally an illustrative example of a relationship between the magnitude of a response signal vs. frequency.

In an example, the electrical characteristics of the implantable lead can vary as a function of frequency, such as shown in FIG. 6, over a specified frequency range (e.g., from about 10 KHz to about 100 KHz, from about 10 KHz to about 30 MHz, from about 10 MHz to about 150 MHz, etc.), such as a result of the capacitive or inductive interaction between a conductive portion of the lead and another conductor either located within the lead or elsewhere. In an example, the implantable lead 145 can be physically connected to the heart 205, or physically located near or within the heart 205, such that movement of the heart (e.g., a cardiac contraction cycle) can result in movement of the lead body. Such movement of the lead body can cause a corresponding change to the electrical characteristics (e.g., lead capacitance, lead inductance, etc.).

For example, the lead impedances 350-360 can vary as a function of time corresponding to the movement of the implantable lead, such as during a cardiac cycle. Lead motion can include movement, or physical manipulation, of the implantable lead due to motion, such as caused by a cardiac contraction cycle (e.g., bending, stretching, twisting, impact, torsion, compression, etc.). In an example, the motion of the implantable lead 145 can include physical disturbance to the lead due to impact (e.g., a heart valve impact), frictional movement (e.g., frictional contact to cardiac tissue, or other tissue), radial compression (e.g., such as due to variation in blood pressure), or the like. In an example, lead motion can include physical translation or rotation of the lead body relative to a point fixed in space (e.g., a point on the body, inertial frame, etc.), such as might be measurable with a lead based accelerometer.

Figure 4:
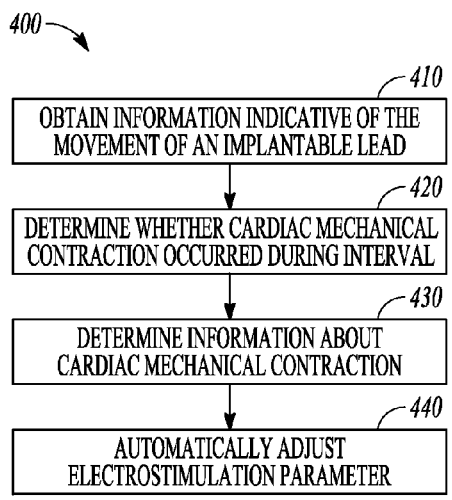
FIG. 4 illustrates generally an example of a technique for analyzing information indicative of the movement of the implantable lead.

FIG. 4 illustrates generally an example of a technique for analyzing information indicative of the movement of the implantable lead. At 410, information indicative of the motion of the implantable lead 145 (e.g., an LMI signal) can be obtained, such as using a response signal obtained from the implantable lead 145. In an example, the receiver circuit 115 can be configured to receive a response signal, such as received from the implantable lead 145, in response to a an excitation signal, such as delivered by the excitation circuit 110. In an example, the excitation circuit 110 can deliver an excitation signal over a specified frequency range. In an example, the interaction of electrical characteristics of the implantable lead 145 and the excitation signal can generate the response signal. Such electrical characteristics of the implantable lead 145, (e.g., lead impedances 350-360) can change in response to a motion of the implantable lead, such as caused by a motion of the heart 205. For example, the lead impedances 350-360, such as due to capacitive, or inductive coupling, can vary in time, such as caused by the time-varying motion of the implantable lead 145. For example, the response signal can be processed, such as using a filter, to determine a mechanical contraction waveform indicative of the motion of the implantable lead over one or more cardiac contraction cycles.

At 420, an ambulatory device, such as the IMD 105, can be configured to determine whether a cardiac mechanical contraction occurred during a specified interval such as included in the obtained information indicative of the movement of the implantable lead. In an example, the processor 190 can be configured to obtain at least a portion of the mechanical contraction waveform such as to determine whether a contraction has occurred between two loci on the waveform. For example, the loci can correspond to a location at or near the start of an "uncontracted" state of the heart. In an example, the information indicative of a cardiac mechanical contraction can correspond to an indication of cardiac relaxation (e.g., a magnitude at or near zero or some other specified baseline) followed by an indication of cardiac contraction (e.g., a magnitude crossing a specified threshold, or reaching a specified peak or peak-to-peak magnitude), such as followed by an indication of cardiac relaxation (e.g., the return to the "uncontracted" state at or near the baseline).

At 430, the IMD 105 can be configured such as to determine information about the cardiac mechanical contraction using the obtained information about the movement of the implantable lead. In an example, a processor, such as the processor 190, can determine information about the mechanical contraction via determining one or more of (1) an interval between two loci included in a mechanical contraction waveform, (2) an amplitude corresponding to a portion of the mechanical contraction waveform, or (3) information indicative of a rate of change of a portion of the mechanical contraction waveform, as described above. For example, the processor 190 can be configured to determine at least one of a central tendency, a peak-to-peak determination, a peak determination, a root-mean-square determination, a statistical ranking, or an absolute value of at least a portion of the mechanical contraction waveform.

At 440, the IMD 105 can be configured to adjust a generated therapy, such as by the therapy generation circuit 135, such as by using the information about the cardiac mechanical contraction. In an example, the therapy generation circuit 135 can adjust a generated therapy using one or more electrostimulation parameters, such as a pacing time, a pacing duration, a pacing site, a pacing energy, or by coordinating the delivery of pacing energy on two or more leads. For example, a processor circuit, such as the processor 190, can adjust a pacing timing such as by using interval information, such as an interval between a delivered pacing pulse and a resulting indication of a mechanical contraction. In an example, the processor 190 can determine whether a cardiac mechanical contraction occurred within a specified interval, such as by determining a rise time of a contraction between an "uncontracted" state and a contracted state. A pacing therapy parameter, such as for CRT, can be adjusted such as to obtain a specified change in rise time (e.g., increasing or decreasing a rate of change of the rise-time, or adjusting the rise time).

Figure 5:
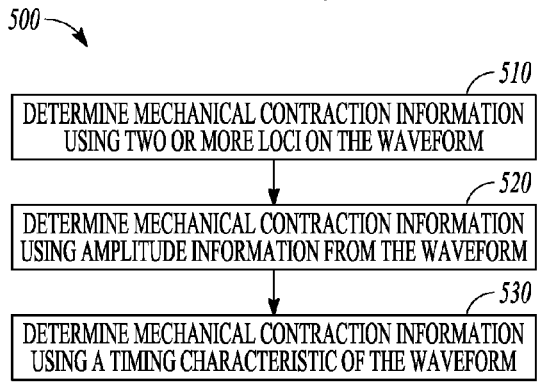
FIG. 5 illustrates generally an example of a technique for determining information about a cardiac mechanical contraction.

FIG. 5 illustrates generally an example of a technique 500 that can include determining information about a cardiac mechanical contraction, such as to guide a therapy or determine a physiological condition. At 510, the IMD 105 can determine interval information, such as to determine a heart rate indication, a rise time, or a fall time. At 510, a processor can determine information about the cardiac mechanical contraction, such as by determining two or more loci on the waveform, as described above. For example, the processor 190 can determine a locus such as located at or near a beginning of a contraction of a first cardiac contraction cycle, and a second locus similarly located on a successive or adjacent second cardiac contraction cycle such as can be indicative of a heart rate.

At 520, the IMD 105 can determine amplitude information such as described above (e.g., a peak magnitude, peak-to-peak magnitude, an average, etc.). The IMD 105 can determine amplitude information such as can include one or more of a central tendency (e.g., an average, a median, a mean, etc.), a peak-to-peak determination, a peak determination, a root-mean-square determination, a statistical ranking, or an absolute value of at least a portion of the mechanical contraction waveform. For example, amplitude information, such as peak information, can correspond to a contracted state of the heart.

At 530, the IMD 105 can determine whether to use rate of change information, such as described above. The IMD 105 can determine a rate of change, such as of a magnitude over a specified duration. For example, the processor 190 can determine a rise-time or a fall time as described above, such as to determine whether a fusion has been achieved such as between a paced ventricular beat and an intrinsic atrial beat.

FIG. 6 illustrates generally an illustrative example of a relationship between the magnitude of a response signal versus frequency. As described above, the IMD 105 can include a receiver circuit 115, for example, configured to receive a signal indicative of the motion of the implantable lead, such as the response signal, obtained in response to an excitation signal provided by the excitation circuit 110. In an example, the magnitude 600 of the response signal can vary as a function of frequency due the electrical characteristics of the implantable lead 145 over a specified frequency range. For example, a relatively stable or "flat" magnitude response (e.g., a magnitude value within a defined range) can result from the interaction of the electrical characteristics of the implantable lead 145 and the excitation signal in a first frequency range 605, such as between DC or near-DC (e.g., about 0 Hz) and a second frequency 615 (e.g., about 10 KHz), such as due to the resistive components of the lead impedances 350-360 having more influence than the capacitive, or inductive components. However, for an excitation signal within a second frequency range 607 (e.g., from about 50 MHz to about 150 MHz), the capacitive or inductive elements of the lead impedances 350-360 can dominate the response, such as causing the response signal magnitude 610 to decline as a function of frequency over the second frequency range 607.

In an example, the interaction of an excitation signal at a frequency, such as frequency 617, and the electrical characteristics of the implantable lead 145 can result in a response signal 620, such as having a magnitude 622. In an example, the electrical characteristics of the implantable lead 145 can result from inductive or capacitive coupling between portions of the implantable lead such as due to the position and or location of the implantable lead 145 within or near the heart. In an example, the motion of the heart, such as a cardiac contraction cycle, can result in corresponding motion of the implantable lead 145. In an example, the motion of the implantable lead can cause the electrical characteristics of the implantable lead 145 to vary as a function of time. For example, the motion of the implantable lead can cause the magnitude of the response signal to vary as a function of time over a specified frequency range. Such magnitude signals 640, 650, can result from the variance in the electrical characteristics due to motion of the implantable lead caused, at least in part, by motion of the heart 205.

In an example, an excitation signal at a frequency 617, such as provided by the excitation circuit 110, can interact with the time-varying electrical characteristics of the implantable lead 145, such as to provide a signal indicative of the motion of the implantable lead 145 (e.g., a response signal at least in part including an LMI signal 630). For example, the excitation signal at a frequency 617 can interact with the time-varying electrical characteristics of the implantable lead 145 during motion of the implantable lead. The motion of the implantable lead 145, such as caused a cardiac contraction cycle, can result in a response signal at a specified frequency having a time-varying magnitude value that can vary between a peak value 632A and a minimum value 634A. In an example, the response signal can include a carrier signal at the excitation frequency 617, and a modulating signal, such as a time-varying component resulting from the motion of the implantable lead (e.g., the LMI signal 630). For example, the magnitude of the LMI signal 630 can correspond to the time-varying magnitude of the response signal at the specified frequency such that the magnitude of the LMI signal 630 can vary between a peak value 632B and a minimum value 634B. In an example, the response signal can be conditioned such as to extract or otherwise provide the LMI signal for use by an analysis circuit, such as the arrhythmia classification circuit 120.

Phase information can also be obtained, such as with respect to a reference phase corresponding to the excitation signal. Thus, the techniques above can be applied generally to magnitude or phase information, or to a real part or imaginary part of the response signal, in the case of a complex response signal. Phase information can also be obtained, such as with respect to a reference phase corresponding to the excitation signal. Thus, the techniques above can be applied generally to magnitude or phase information, or to a real part or imaginary part of the response signal, in the case of a complex response signal.

Figure 7:
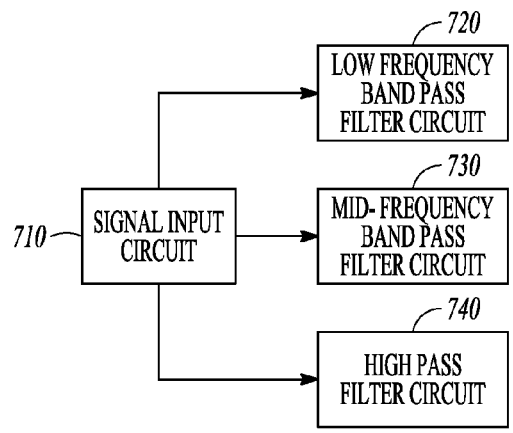
FIG. 7 illustrates generally an example of a system that can be used for conditioning a signal.

FIG. 7 illustrates generally an example of a system that can be used for conditioning a response signal for analysis. In an example, the receiver circuit 115 can include a signal input circuit 710, such as configured to receive a response signal from the implantable lead 145. In an example, the signal input circuit can include circuitry such as configured to provide the LMI signal such as provided or otherwise obtained from the response signal. For example, the LMI signal can be obtained via demodulation, such as to remove a carrier frequency 617, such as to provide the LMI signal (e.g., via AM demodulation such as envelope detection or filtering, or via FM demodulation such as using a phase-locked loop, etc.). In an example, the LMI signal can include information about the motion of the implantable lead, such as caused by mechanical manipulation of the one or more leads caused by motion of at least one of the heart muscle, a heart valve, respiratory musculature, lungs, skeletal musculature, a variation in blood pressure, or other forces acting on the one or more leads.

In an example, the receiver circuit 115 can include one or more filters to provide information about one or more physiological conditions associated with the heart, such as information about the motion of the implantable lead in the LMI signal. In an example, the implantable lead 145 can be moved slowly, such as due to bending resulting from a cardiac contraction cycle. The implantable lead 145 can move quickly, such as caused by an impact on the lead resulting from a valve closure. In an example, the LMI signal can be filtered in one or more frequency ranges, such as to distinguish between one or more causes of the motion of the implantable lead. In an example, the receiver circuit 115 can include a low-frequency band pass filter circuit 720, a mid-frequency band pass filter circuit 730, or a high pass filter circuit 740. In an example, the filter circuits 720-740 can include a near-DC filter circuit, such as a high pass filter circuit configured to attenuate or remove signal noise under a frequency (e.g., about 0.05 Hz), configured to provide a baseline such as by filtering near-DC signal components. For example, the baseline can correspond to a near zero-energy or near-zero magnitude LMI signal when the implantable lead is not moving. In an example, the near-DC filter circuit can be included in one or more of the low-frequency band pass filter circuit 720, the mid-frequency band pass filter circuit 730, or the high pass filter circuit 740.

In an example, the low-frequency band pass filter circuit 720 can be configured to filter the LMI signal, for example, at a low frequency range (e.g., from about 0.05 Hz to about 10 Hz), such as to provide information indicative of the motion of the implantable lead 145, such as due to mechanical motion of the heart 205. For example, the low-frequency band pass 720 filter can provide a filtered LMI signal representative of the motion of the implantable lead due to motion caused by a cardiac contraction cycle. In an example, the filtered LMI signal can provide information representative of motion of the one or more implantable leads such as can be useful for verification of capture of a pacing pulse, managing fusion in capture detection applications or CRT applications, or monitoring to detect a lead dislodgment. In an example, the filtered LMI signal can be used for monitoring myocardial contraction such as to optimize a CRT therapy, to detect myocardial ischemia, to determine relative changes in stroke volume, or cardiac output, to detect abnormalities with relaxation of the cardiac muscle, or to detect abnormal mechanical contraction and to monitor electro-mechanical delay in the myocardium.

In an example, the mid-frequency band pass filter circuit 730 can be configured to filter the LMI signal, such as over a mid-frequency range (e.g., from about 0.05 Hz to about 30 Hz), such as to provide information indicative of the motion of the implantable lead 145, such as due to mechanical motion of the heart 205. For example, the mid-frequency band pass filter 730 can provide a filtered LMI signal representative of the motion of the implantable lead due to motion caused by a cardiac contraction cycle. For example, the filtered LMI signal can provide information useful for decompensation detection, rhythm discrimination using myocardial contraction morphology or myocardial contraction spectrum, to guide therapy to determine if ATP should be attempted before a shock, or to determine the timing of the shock, arrhythmia detection, or assessing autonomic function. In an example, the filtered LMI signal can be used to monitor the integrity of the implantable lead.

In an example, the high pass filter circuit 740 can be configured to filter the LMI signal, such as to filter signal out signal components under a specified frequency range (e.g., above about 10 Hz), such as to provide information indicative of the motion of the implantable lead 145, such as due to mechanical motion of the heart 205. For example, the mid-frequency band pass filter 730 can provide a filtered LMI signal representative of the motion of the implantable lead due to motion caused by one or more portions of the heart during a cardiac contraction cycle (e.g., a valve impact, frictional contact between cardiac muscle and the implantable lead, etc.). For example, the filtered LMI signal can provide information useful to detect heart sounds, or to detect the timing and amplitude of valve impact on leads. In an example, the filtered LMI signal can be used to detect lead maturity (e.g., a connection between myocardial tissue and the implantable lead 145), or lead dislodgement. In an example, the filtered LMI signal can be used for dissynchrony measurement or CRT optimization, such as by detecting right side and left side heart sounds.

Figure 8:
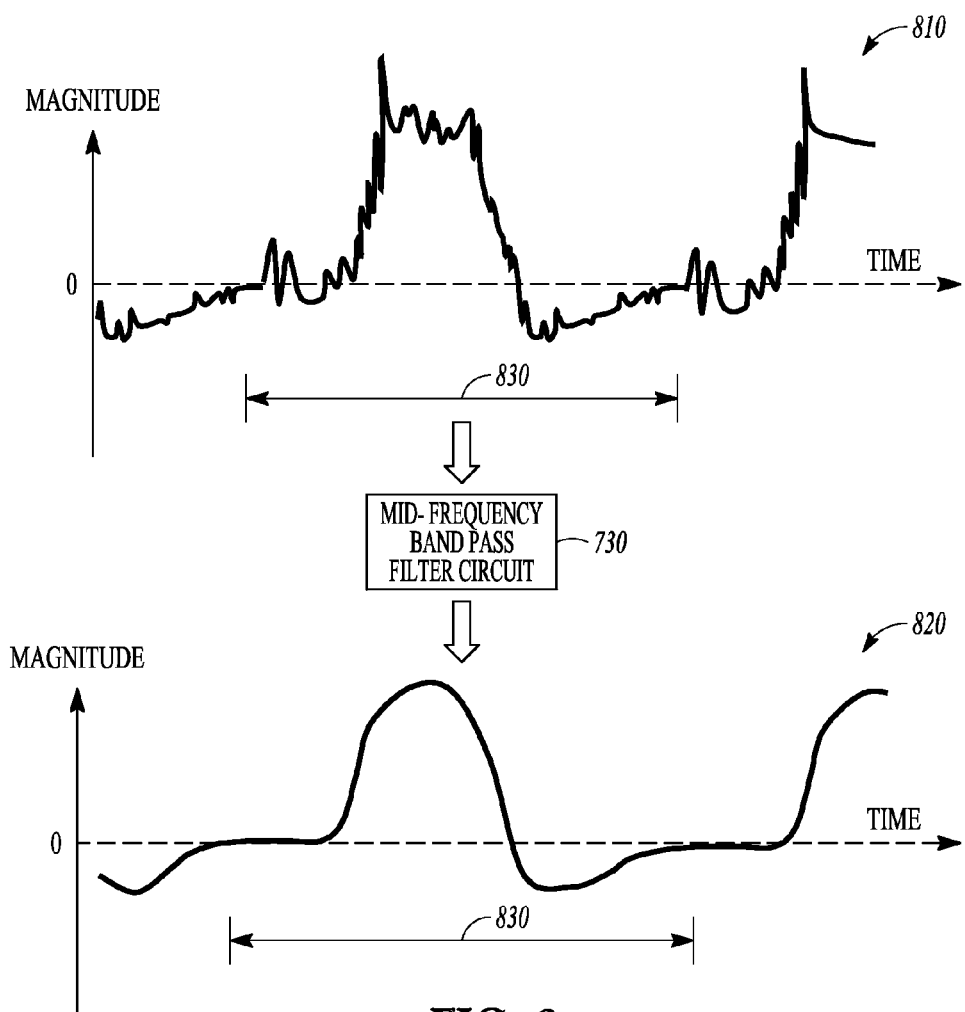
FIG. 8 illustrates generally an illustrative example that can include filtering or otherwise conditioning a response signal.

FIG. 8 illustrates generally an illustrative example that can include filtering or otherwise conditioning a response signal. In an example, an LMI signal can be received by the receiver circuit 115, such as can include an LMI signal indicative of the motion of the implantable lead 145, such as the LMI signal 810. In an example, the LMI signal 810 can be filtered, such as to provide information about the cardiac contraction cycle. For example, the LMI signal 810 can be filtered, such as by the mid-frequency band pass filter 730, such as to provide a filtered LMI signal 820 such as a mechanical contraction waveform.

Figure 9:
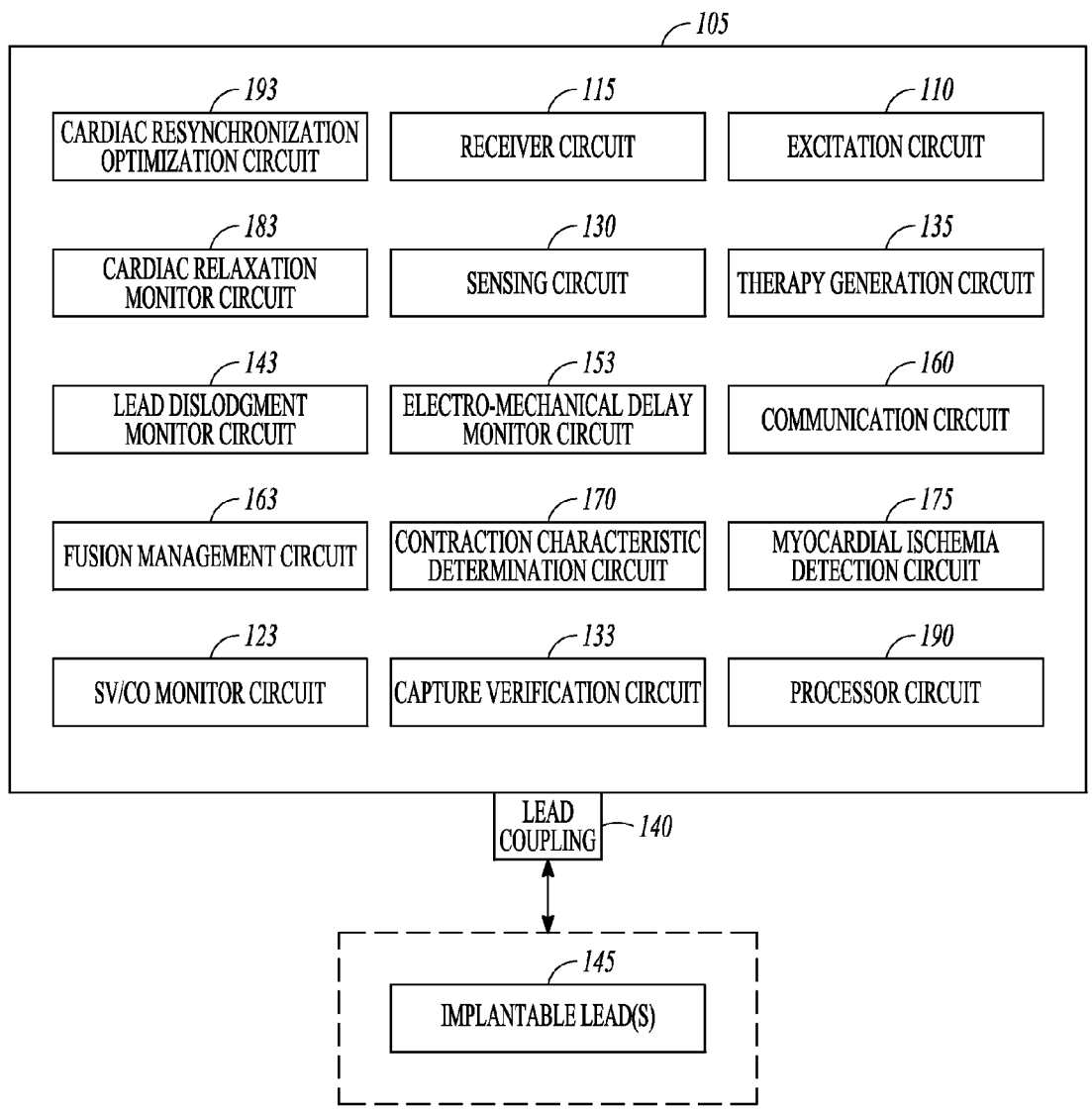
FIG. 9 illustrates generally an example of an ambulatory medical device that can be configured to analyze a signal indicative of the movement of the implantable lead.

FIG. 9 illustrates generally an example of an ambulatory medical device that can be configured to analyze a signal indicative of the movement of the implantable lead 145, such as for an indication of the movement of the heart 205 during a cardiac contraction cycle. In an example, the IMD 105 can include one or more of the excitation circuit 110, the receiver circuit 115, an arrhythmia detection circuit, an arrhythmia classification circuit, the sensing circuit 130, the therapy generation circuit 135, the lead interface connection 140, a communication circuit 160, the SV/CO monitor circuit 123, the capture verification circuit 133, the lead dislodgment monitor circuit 143, the electromechanical delay monitor circuit 153, the fusion management circuit 163, the myocardial ischemia detection circuit 173, the cardiac relaxation monitor circuit 183, the cardiac resynchronization optimization circuit 193, or a processor circuit 190.

In an example, the processor circuit 190 can include the capture verification circuit 133, such as to provide information corresponding to the effectiveness of a therapy, such as a pacing therapy delivered by the therapy delivery circuit 135. For example, the capture verification circuit 133 can provide information, such as included in at least a portion of a mechanical contraction waveform, capable of determining whether a delivered therapy (e.g., a pacing pulse) produced an expected result. For example, the capture verification circuit 133 can determine information corresponding to character and timing of the resulting cardiac contraction. For example, the capture verification circuit 133 can determine interval information, such as an interval between a delivery of a therapy (e.g., a pacing pulse) and a ventricular contraction. For example, the capture verification circuit 133 can use the interval information such as to determine whether cardiac capture has occurred, such as when the time interval between the intrinsic atrial beat and a mechanical indication of a paced ventricular contraction meets a specified criterion (e.g., occurs within about 200 ms, or within another specified interval).

In an example, the capture verification circuit 133 can be configured to provide capture verification information using the mechanical contraction waveform such as to provide capture verification information additionally, or alternatively, to using a signal indicative of cardiac electrical activity (e.g., a signal corresponding to a portion of an electrogram such as provided by the sensing circuit 130). For example, a feature of the mechanical contraction waveform (e.g., a portion of a waveform near a peak magnitude) can be associated with an electrical indication of a contraction (e.g., a QRS portion of an electrical signal). The capture verification circuit 133 can be configured to use the mechanical contraction waveform to verify capture verification information, such as from an electrogram analysis, such as when capture verification information fails to be determined from the electrogram (e.g., due to noise or one or more other factor inhibiting or preventing detection of an evoked response via analysis of sensed cardiac electrical activity).

The processor circuit 190 can be configured such as to use a feature of a portion of a signal indicative of cardiac electrical activity (e.g., a QRS structure, or an indication of a paced pulse) as a fiducial (e.g., a marker or other reference to provide a time index). For example, the processor circuit 190 can use the fiducial such as to align a signal indicative of cardiac electrical activity to a mechanical contraction waveform. In an example, the processor circuit 190 can be configured such as to use the fiducial as a trigger for analysis of a mechanical contraction waveform. For example, the capture verification circuit 133 can be configured to use a fiducial associated with the delivery of a pacing pulse to trigger an analysis of at least a portion of the mechanical contraction waveform for an indication of a cardiac contraction such as to confirm capture. For example, capture can be verified such as by detecting that a mechanical contraction occurred within a specified threshold following the delivered pacing pulse (e.g., within a range between about 100 ms and about 200 ms, or one or more other ranges).

In an example, the processor circuit 190 can include the SV/CO monitor circuit 123 configured to monitor stroke volume (SV) or cardiac output (CO), such as to monitor changes in SV or changes to CO (e.g., determine a change in SV or CO). SV and CO can represent the heart's ability to perform work, such that SV can represent the heart's ability to pump blood with each beat and CO can represent the amount of blood pumped by the heart (e.g., liters per minute). For example, CO can be determined using a formula (CO=SV× HR), where the units of each are as follows: CO=liters/minute; SV=liters/beat; and heart rate (HR) is in beats/minute. In an example, SV can be determined using a relative indication of information, such as the difference between the end-diastolic volume (EDV) and the end-systolic volume (ESV), such as can be determined in a generally-used technique using an echocardiogram.

In an example, the SV/CO monitor circuit 123 can be configured to determine an indication of change to at least one of SV or CO using one or more mechanical contraction waveforms without requiring an echocardiogram, such as to determine amplitude, rate of change information, interval information, or cardiac synchrony information associated with a portion of one or more cardiac contraction waveforms. In an example, an implantable lead located within or near the heart, such as the implantable lead 145, can provide information corresponding to the mechanical contraction of the heart, such as when the mechanical placement and electrical behavior of the implantable lead becomes more stable over time (e.g., "matures"). For example, the implantable lead 145 can become mechanically anchored such as tissue ingrowth or endothelialization to a portion of the heart (e.g., endocardium or epicardium). In an example, fibrous tissue growth can provide a secure mechanical connection between the implantable lead 145 and the heart tissue, such as to provide a stable (e.g., consistent or repeatable) mechanical contraction waveform representative of movement of at least a portion of the heart.

In an example, the SV/CO monitor 123 can be configured to determine SV or CO using information from at least a portion of the mechanical contraction waveform, alone or in combination with, one or more physiological signals received from the sensor circuit 130 (e.g., a cardiac electrical activity signal, a blood pressure signal, an oxygen saturation signal, etc.). For example, SV can be indicated using a blood pressure signal such as disclosed in relation to resynchronization therapy techniques of the commonly assigned U.S. Pat. No. 7,158,830, entitled "METHOD AND APPARATUS FOR OPTIMIZING STROKE VOLUME DURING DDD RESYNCHRONIZAITON THERAPY USING ADJUSTABLE ATRIO-VENTRICULAR DELAYS," which is herein incorporated by reference in its entirety, including its description of maximizing stroke volume using a technique to calculate AVD for optimal timing of a ventricular pacing pulse. In an example, the SV/CO monitor circuit 123 can be configured such as to determine an indication of SV or CO using at least one of amplitude information, interval information, or rate of change information from of at least a portion of the mechanical contraction waveform, as described above. For example, the SV/CO monitor circuit 123 can determine amplitude information such as to indicate a change in mechanical contraction forcefulness (e.g., an increase or decrease in amplitude).

In an example, the processor circuit 190 can include the lead dislodgment monitor circuit 143, such as to determine a status associated with the connection of the one or more implantable leads to the heart. In an example, the lead dislodgment monitor circuit 143 can be configured such as to monitor a mechanical contraction waveform, such as to determine an indication of a change to the mechanical contraction waveform (e.g., an indication of a lead dislodgment). For example, the lead dislodgment monitor circuit 143 can determine a change to the mechanical contraction waveform such as resulting from a change to the location of the implantable lead 145 (e.g., a sudden change in waveform morphology or shape). In an example, the lead dislodgment monitor 143 can be configured to determine the indication of lead dislodgment of the implantable lead 145 using information obtained from one or more of a mechanical contraction signal, or a signal indicative of cardiac electrical activity, each sensed using the signals sensed from the implantable lead 145.

In an example, the processor circuit 190 can include the fusion management circuit 163 that can be configured to determine fusion information such as can be used to adjust therapy parameters. In an example, the IMD 105 can be configured such as to provide a therapy (e.g., CRT) to provide appropriately timed electrical stimulation to one or more heart chambers to improve the coordination of atrial and/or ventricular contractions. Generally, CRT can simultaneously generate pacing pulses to both ventricles, can generate pacing pulses separated by a specified biventricular offset interval, or can generate pacing pulses after a specified AVD interval with respect to the detection of an intrinsic atrial contraction or a generated atrial pacing pulse. A fusion beat can occur when two cardiac depolarizations from different initiation sites (e.g., an intrinsic beat and a paced beat) merge in a particular heart chamber (e.g., the left ventricle). Pseudo-fusion can occur when a pacing pulse is delivered such as during a spontaneous P wave during atrial pacing or on a spontaneous QRS complex during ventricular pacing. In pseudo-fusion, the pacing pulse may be ineffective because the tissue around the electrode has already spontaneously depolarized and is in its refractory period. Such fusion and pseudo-fusion beats can exhibit various morphologies, such as can be determined using information from at least a portion of an electrogram or an LMI signal. In an example, the fusion management circuit 163 can be configured to manage fusion (e.g., fusion or pseudo-fusion in the left ventricle) resulting from a depolarization interaction between a propagated depolarization (e.g., such as from an intrinsic beat, an atrial pacing pulse, a right ventricular pacing pulse) and a left ventricular pacing pulse.

In an example, the depolarization patterns of a ventricle can differ for a paced beat, an intrinsically activated beat, or a fusion beat, such as discussed in relation to the techniques to determine fusion statistics of the commonly assigned U.S. patent application Ser. No. 12/781,411, entitled "SYSTEMS AND METHODS FOR THE GENERATION AND DISPLAY OF FUSION STATISTICS," filed on May 17, 2010, published as US Publication No. 2010/0305646 A1 which is herein incorporated by reference in its entirety, including its description of determining and analyzing electrogram morphological patterns to determine fusion statistics. In an example, the fusion management circuit 163 can be configured to analyze a morphological pattern of at least a portion of a mechanical contraction waveform (e.g., compare to a template from a normal sinus contraction) such as to indicate fusion. For example, a fusion indicating morphological pattern can be indicated such as by a waveform shape indicating a longer contraction (e.g., wider than the template by greater than a threshold), or a shape indicating a dyssynchronous contraction (e.g., a lower peak, or multiple peaks over a single contraction).

In an example, the fusion management circuit 163 can be configured to analyze at least one of timing information, amplitude information, or rate change information such as can be determined from one or more portions of a mechanical contraction waveform. For example, the fusion management circuit 163 can be configured to determine information corresponding to a heart transitioning between an "uncontracted" state to a contracted state, and back, such as using the mechanical contraction waveform. In an example, the fusion management circuit 163 can be configured to identify fusion, such as by comparing a mechanical contraction waveform over two or more cardiac contraction cycles. For example, fusion can be indicated such as by using contraction time (e.g., rise time meeting a specified criterion), such as indicated during a portion of the mechanical contraction waveform.

In an example, the fusion management circuit 163 can be configured to provide one or more of fusion information or therapy adjustment parameters, such as to the therapy delivery circuit 135. In an example, the fusion management circuit 163 can be configured to determine one or more of a pacing parameter (e.g., a timing parameter, a pacing site parameter) for left ventricular pacing, or for right ventricular pacing, such as determined using information from a portion of one or more mechanical contraction waveforms.

In an example, the processor circuit 190 can include the myocardial ischemia detection circuit 173, such as to determine an indication of myocardial ischemia using information included in a cardiac contraction waveform, as described above. In an example, the myocardial ischemia detection circuit 173 can be configured such as to identify an ischemic event using a comparison of one or more portions of cardiac contraction waveforms, such as using amplitude information (e.g., a morphology of the LMI response waveform corresponding to a cardiac contraction cycle). For example, myocardial ischemia can result from a reduction of the blood supply to a portion of the heart that can alter or inhibit cardiac function. Such altered or inhibited cardiac function can manifest as an altered mechanical contraction waveform obtained from one or more of the implantable leads 145.

For example, the myocardial ischemia detection circuit 173 can be configured to compare a portion of the mechanical contraction waveform over a first duration to a corresponding portion of the mechanical contraction waveform over a second duration, such that information indicative of myocardial ischemia can be determined. For example, myocardial ischemia at a portion of the heart can result in a decrease in vigor of the cardiac contraction, such as can be indicated by comparing a portion of a mechanical contraction waveform over two or more specified durations such as to detect a change in morphology. In an example, the myocardial ischemia detection circuit 173 can be configured to determine an indication of myocardial ischemia using one or more of a mechanical contraction waveform, or one or more portions of a signal indicative of cardiac electrical activity (e.g., an ST segment of an ECG).

In an example, the myocardial ischemia detection circuit 173 can be configured to determine an indication of one or more of an acute myocardial ischemia, or a transient myocardial ischemia, such as using one or more mechanical contraction waveforms. In an example, the myocardial ischemia detection circuit 173 can be configured to analyze a portion of the one or more mechanical contraction waveforms continuously, or over specified durations for an indication of myocardial ischemia. In an example, the myocardial ischemia detection circuit 173 can be configured to analyze at least a portion of the mechanical contraction waveforms, occasionally (e.g., once every few minutes, hourly, several times per day, or during or between one or more other specified intervals) for an indication of myocardial ischemia. In an example, the myocardial ischemia detection circuit 173 can be configured to analyze a portion of the one or more LMI signals, such as a mechanical contraction waveform for an indication of myocardial ischemia as a result of a physiological signal, such as a physiological signal obtained by the processor circuit 190 from the sensing circuit 130.

In an example, the processor circuit 190 can include the cardiac relaxation monitor circuit 183, such as to analyze one or more mechanical contraction waveforms such as to determine relaxation information about the myocardium. For example, the cardiac relaxation monitor circuit 183 can be configured to analyze one or more of amplitude information, interval information, or rate of change information, as described above. In an example, the cardiac relaxation monitor circuit 183 can be configured to analyze a portion of a mechanical contraction waveform such as a portion associated with the transition from the contracted state to the "uncontracted" state of the myocardium.

In an example, the cardiac relaxation monitor circuit 183 can be configured such as to detect one or more physiologic conditions that can impair cardiac function, such as HF (e.g., diastolic or systolic heart failure) or fluid overload. For example, an increased fall time can indicate an abnormal calcium cycling in the cardiac cells, a decreased myocardial perfusion, an electrolyte disturbance, or one or more other metabolic conditions. In an example, the cardiac relaxation monitor circuit 183 can be configured such as to compare a mechanical contraction waveform from for a current time duration to a reference obtained previously.

In an example, the cardiac relaxation monitor circuit 183 can be configured to analyze a portion of a mechanical contraction waveform, such as a fall time (e.g., between 10% and 90% of the peak value), such as to obtain information corresponding to cardiac relaxation. If, for example, the fall time information meets the criterion for an increased duration for heart relaxation, such as the fall time exceeding a threshold, the cardiac relaxation monitor circuit 183 can generate an indication of impaired cardiac relaxation. If the fall time information indicates a decrease in fall time, such as meeting a criterion (e.g., where a difference between a baseline fall time and a measured fall time exceeds a threshold), the cardiac relaxation monitor circuit 183 can generate an indication of increased filling pressure, such as to the left atrium or pulmonary vein.

In an example, the processor circuit 190 can include the cardiac resynchronization optimization circuit 193, such as to synchronize a mechanical atrial contraction to a ventricular contraction, (e.g., synchronizing a ventricular pacing therapy to an intrinsic atrial beat) or to synchronize a right ventricle contraction to a left ventricle contraction (e.g., synchronizing delivery of a right ventricular pacing pulse to a left ventricular pacing pulse, selecting a pacing site for at least one of the right ventricle or the left ventricle). For example, the cardiac resynchronization optimization circuit 193 can be configured to synchronize a ventricular pacing pulse to an intrinsic atrial beat, such as by using magnitude information, interval information, or rate of change information, as described above. Similarly, the cardiac resynchronization optimization circuit 193 can be configured to synchronize a right ventricular pacing pulse to a left ventricular pacing pulse, such as by using magnitude information, interval information, or rate of change information.

In an example, the cardiac resynchronization optimization circuit 193 can be configured to synchronize the mechanical contractions of at least two portions of the heart), such that CO can meet the physiologic demand with a minimum or reduced amount of expended energy as compared to a diseased heart's intrinsic contractile behavior. For example, the cardiac resynchronization optimization circuit 193 can be configured to determine timing information and pacing site information such as can be used for generating a pacing pulse. For example, the cardiac resynchronization optimization circuit 193 can be configured to automatically adjust at least one of a right ventricular pacing pulse timing parameter or a left ventricular pacing pulse timing parameter, such as by using mechanical contraction information corresponding to sensed or paced atrial activity. The cardiac resynchronization optimization circuit 193 can be configured to automatically adjust a left ventricular pacing timing parameter such as by using mechanical contraction information associated with sensed or paced right ventricular activity (e.g., biventricular delay (VVD) or AVD). In an example, at least one of a left ventricular pacing site or a right ventricular pacing site can be determined such as by using magnitude information, interval information, or rate of change information as described above.

In an example, the IMD 105 can be configured to present one or more of the magnitude information, timing information, or rate of change information to a caregiver (e.g., a clinician), such as for diagnosis or therapy adjustments, via an external device (e.g., a programmer on the external network 270). For example, the clinician can manually adjust at least one of a right ventricular pacing pulse timing parameter or a left ventricular pacing pulse timing parameter, such as by using mechanical contraction information corresponding to sensed or paced atrial activity presented via the programmer on the external network 270.

Figure 10:
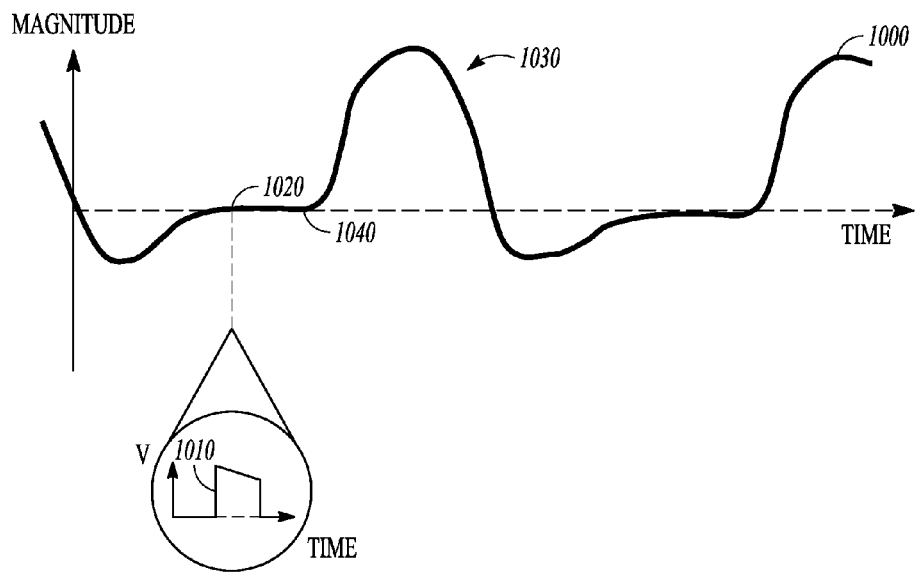
FIG. 10 illustrates generally an illustrative example of a relationship between a pacing pulse and a mechanical cardiac contraction.

FIG. 10 illustrates generally an illustrative example of a relationship between a pacing pulse 1010 and a mechanical cardiac contraction 1030. A patient receiving a pacing therapy, such as a pacing therapy for treating an arrhythmia, the mechanical contraction waveform 1000 can provide an indication of therapy effectiveness (e.g., capture verification information). Such an indication can be determined such as by using interval information between time of the generation 1020 of the pacing pulse 1010 and a time 1040 at or near the start of the mechanical cardiac contraction 1030. In an example, capture verification information can be determined, such as by the processor circuit 190, using a portion of signal indicative of cardiac electrical activity (e.g., electrogram information indicative of electrical depolarization following pacing pulse generation). However, electrical depolarization alone may not be indicative of capture, such as due to one or more sources of electrical signal interference (e.g., fusion with another beat, variation in sensed event timing or morphology, noise, etc.). In an example, the processor circuit 190 can receive, such as from the receiver circuit 115 or the filter circuit 195, an LMI signal, such as including the mechanical contraction waveform 1000. A pacing pulse 1010 can be deemed to have captured a corresponding contraction 1030 such as when the interval between the time of generation 1020 and a point near or at the start of a cardiac mechanical contraction is less than a threshold (e.g., within about 100 ms, or about 200 ms, of a delivered electrostimulation pulse).

Figure 11:
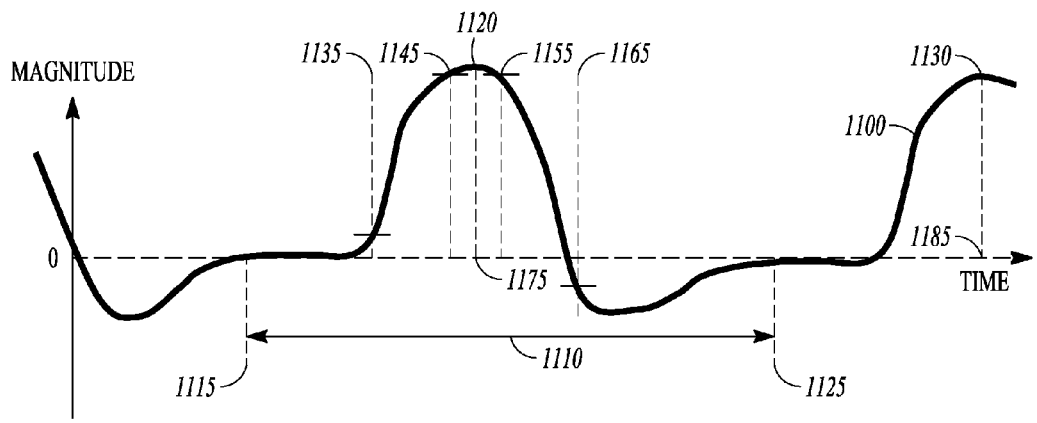
FIG. 11 illustrates generally an illustrative example of information that can be determined from a mechanical contraction waveform.

FIG. 11 illustrates generally an illustrative example of information that can be determined from a mechanical contraction waveform 1100. In an example, a mechanical contraction waveform 1100 can be obtained from one or more implantable leads 145 such as to provide information indicative of a mechanical cardiac contraction. In an example, the mechanical contraction waveform 1100 can include interval information such as between a first locus at 1115 and a second locus 1125, such as can be indicative of a mechanical contraction cycle 1110 of the heart.

In an example, the mechanical contraction waveform 1100 can include peak information 1120, 1130, such as can indicate a peak magnitude associated with the mechanical contraction of the heart. For example, an interval associated with successive or adjacent peaks 1120, 1130 can provide interval information (e.g., between time 1175 and time 1185), such as can be indicative of a heart rate.

In an example, the mechanical contraction waveform can include rate of change information such as a rise time (e.g., between time 1135 and time 1145) or a fall time (e.g. between time 1155 and time 1165). For example, the rise time can be computed between two or more times associated with a specified magnitudes, such as time 1135 associated with a magnitude 10% of the peak value and time 1145 associated with a magnitude of 90% of the peak value, or using one or more other criteria. Conversely, a fall time can be computed between time 1155 associated with a magnitude of 90% of the peak value and time 1165 associated with a magnitude of 10% of the peak value, or using one or more other criteria.

Figure 12:
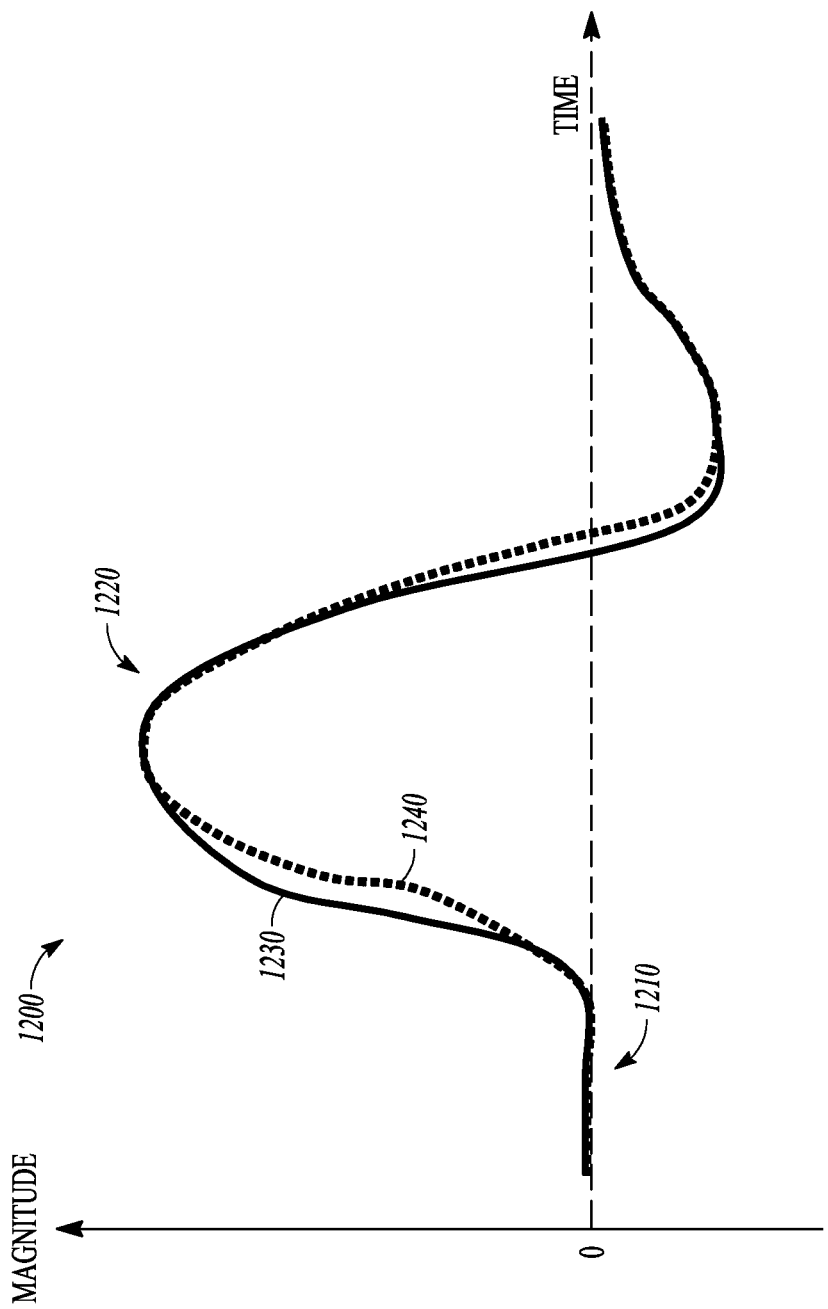
FIG. 12 illustrates generally an illustrative example of information indicative of a change to cardiac health information using information indicative of the movement of the implantable lead.

FIG. 12 illustrates generally an illustrative example of information indicative of a change to cardiac health information using indicative of the movement of the implantable lead 145. For example, a comparison of two or more portions of a mechanical contraction waveform 1220, such as by the myocardial ischemia detection circuit 173, can provide an indication of a change to cardiac health (e.g., an onset of myocardial ischemia). For example, myocardial ischemia can be generally defined as the reduction of blood supply to at least a portion of the heart. Insufficient blood supply can cause the tissue of the heart to become hypoxic, or anoxic, and can eventually cause the heart tissue to die.

In an example, a template, such as at least a portion of a cardiac contraction waveform indicative of a sinus rhythm 1230 (e.g., a mechanical contraction cycle), can be aligned with corresponding features of successive or adjacent portions of the mechanical contraction waveform, such as an indication of an "uncontracted" state 1210 just before a contraction. In an example, a portion of a cardiac contraction cycle 1240 can differ from the template 1230 such as to indicate a change in myocardial function, such as can be indicative of an ischemic condition (e.g., a difference in area under the curve over at least a portion of the waveform exceeds a threshold, or a morphological difference between the curves).

Figure 13:
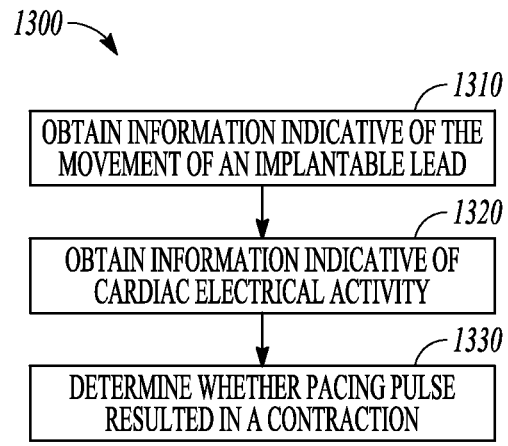
FIG. 13 illustrates generally a technique for capture verification of mechanical motion resulting from a delivered pacing therapy using information indicative of the movement of the implantable lead.

FIG. 13 illustrates generally a technique 1300 for capture verification of mechanical motion resulting from a delivered pacing therapy using information indicative of the movement of the implantable lead. At 1310, information indicative of the motion of the implantable lead 145 can be obtained such as by the capture verification circuit 133, such as to obtain at least a portion of a mechanical contraction waveform indicative of a mechanical contraction (e.g., a portion of the mechanical contraction waveform including peak information). For example, the capture verification circuit 133 can obtain peak information corresponding to a ventricular beat. At 1320, information indicative of cardiac electrical activity (e.g., a portion indicating a QRS feature associated with a ventricular beat) can be obtained such as by the sensing circuit 130, as described above. For example, the capture verification circuit 133 can obtain information associated with a pacing pulse, or a QRS feature, such as by using the sensing circuit 130.

At 1330, the capture verification circuit 133 can determine whether a delivered pacing pulse, as indicated by the signal indicative of electrical activity, captured a corresponding contraction, such as by using at least a portion of the mechanical contraction waveform or the signal indicative of electrical activity. In an example, the capture verification circuit 133 can be configured to determine capture verification information (e.g., whether a pacing pulse captured the myocardium) from an analysis of one or more mechanical contraction waveforms, such as using one or more LMI signals from one or more implantable leads 145. In an example, the capture verification circuit 133 can be configured to analyze the mechanical contraction waveform such as to determine capture verification information using information associated with the delivery of the therapy, such as timing information (e.g., a duration between an indication of a pacing pulse and an indication at or near the beginning of a contraction). For example, the capture verification circuit 133 can be configured to determine an indication of a ventricular contraction such as by analyzing whether the one or more mechanical contraction waveforms moved away from a baseline, within a specified duration (e.g., about 100 ms, about 200 ms, etc.).

In an example, the capture verification circuit 133 can indicate whether the cardiac contraction was captured by the delivered therapy, such as by using a threshold. For example, the capture verification circuit 133 can indicate that the cardiac contraction was captured by the therapy, such as when the amplitude of the mechanical contraction waveform is greater than a first threshold within a specified duration. Similarly, the capture verification circuit 133 can indicate that the delivered therapy failed to capture the cardiac contraction, such as when the amplitude of the mechanical contraction waveform failed to exceed the first threshold value within the specified duration.

Figure 14:
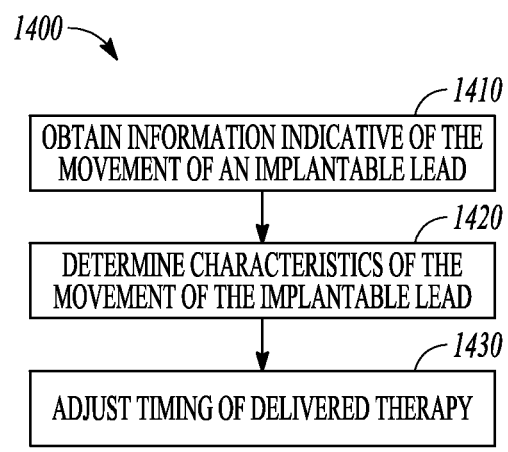
FIG. 14 illustrates generally a technique for managing fusion of paced beats to intrinsic beats during a pacing therapy using information indicative of the movement of the implantable lead.

FIG. 14 illustrates generally a technique 1400 for managing fusion of paced beats to intrinsic beats during a pacing therapy using information indicative of the movement of the implantable lead 145. At 1410, information indicative of the motion of the implantable lead 145 can be obtained such as by the fusion management circuit 163, such as to obtain at least a portion of a mechanical contraction waveform indicative of a mechanical contraction (e.g., amplitude information, interval information, or rate of change information), as described above. At 1420, the fusion management circuit 163 can determine one or more characteristics of the movement of the implantable lead, such as one or more of peak information, peak-to-peak information, timing information (e.g., a rise time), such as can be determined from one or more portions of one or more mechanical contraction waveforms, as described above. In an example, the fusion management circuit 163 can be configured determine fusion information such as to adjust a pacing parameter, at a specified interval (e.g., hourly, daily, etc.).

At 1430, the fusion management circuit 163 can be configured to automatically adjust one or more of the pacing parameters such as to meet a criterion (e.g., provide a rise time under a specified threshold value, or provide a peak to peak magnitude value greater than a specified threshold), For example, a pacing parameter can be automatically adjusted, such as by the fusion management circuit 163, such that a comparison of two or more mechanical contraction cycles can determine a pacing characteristic that can result in either a mechanical contraction cycle having at least one of the shortest possible rise time, or the largest peak-to-peak value. A pacing parameter can be a timing parameter such that can adjust the timing of the delivery of a ventricular pacing pulse (e.g., a right ventricular pacing parameter, a left ventricular pacing parameter, or both), such as in response to an intrinsic atrial contraction. In an example, the fusion management circuit 163 can be configured to be communicatively coupled, such as via the communication circuit 160 using a communication link (e.g., a wired connection, a wireless connection, a RF connection, a communication network, a computer network, etc.) to a monitoring device (e.g., local monitoring device, remote monitoring device, programmer, etc.), such as to provide fusion information to a user. In an example, the fusion management device 163 can be configured to receive one or more pacing adjustment or amplitude adjustment parameters, such as entered by a user.

Figure 15:
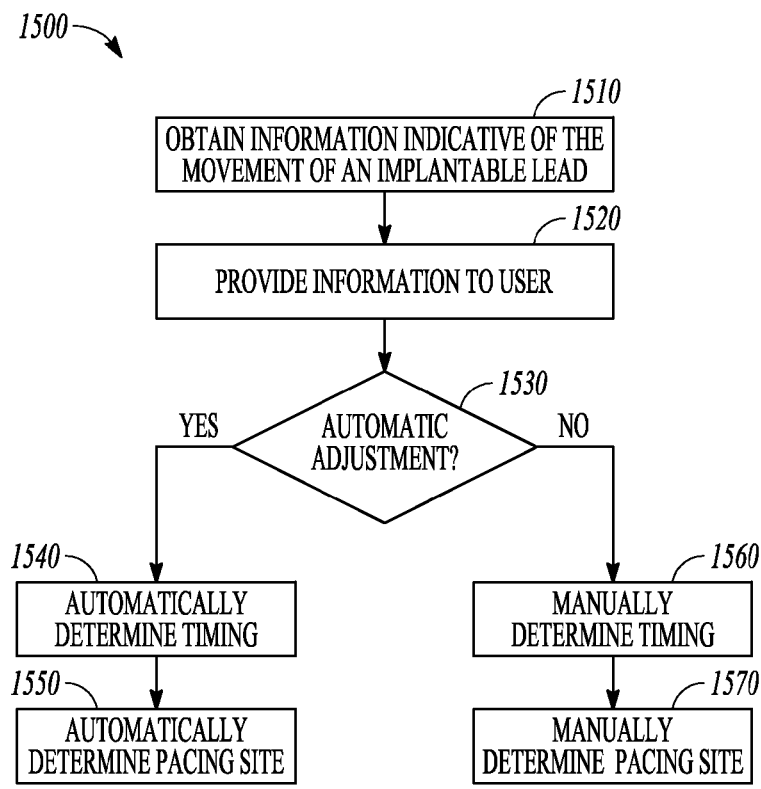
FIG. 15 illustrates generally a technique for managing a cardiac resynchronization therapy using information indicative of the movement of the implantable lead.

FIG. 15 illustrates generally a technique 1500 for optimizing a cardiac resynchronization therapy using indicative of the movement of the implantable lead. At 1510, the processor circuit 190, such as can include a cardiac resynchronization optimization circuit 193 can be configured to obtain information indicative of the motion of the implantable lead 145. Such information can include at least a portion of a mechanical contraction waveform indicative of a mechanical contraction of the heart (e.g., amplitude information, interval information, or rate of change information), as described above. At 1520, the cardiac resynchronization optimization circuit 193 can be configured to be communicatively coupled, such as via the communication circuit 160 using a communication link (e.g., a wired connection, a wireless connection, a RF connection, a communication network, a computer network, etc.) to a monitoring device (e.g., local monitoring device, remote monitoring device, programmer, etc.), such as to provide resynchronization optimization information to a user. For example, the user (e.g., a clinician, physician, caregiver, etc.) can obtain the information indicative of the mechanical contraction of the heart such as via a programmer, such as to allow the user to review the information such as to aid in diagnosis, or to allow for manual entry of adjustment parameters (e.g., a pacing timing, a pacing site, or a pacing energy).

At 1530, the IMD 105 can determine whether to automatically adjust one or more pacing parameters. For example, the user can select, such as using the programmer, whether to allow IMD 105 to automatically adjust the therapy or to manually enter a therapy adjustment. If at 1530, an automatic adjustment is defined, the IMD 105, such as using the cardiac resynchronization optimization circuit 193, can determine at least one of a timing adjustment at 1540, or a pacing site adjustment at 1550. However, if at 1530, a manual adjustment is defined, the IMD 105 can be configured to receive, such as via the programmer, one or more of a timing adjustment at 1560, or a pacing site adjustment at 1570, such as entered by the user.

For example, the resynchronization optimization circuit 193 can be configured to determine a pacing parameter adjustment such as having optimal characteristics, such as having the fastest rise time (e.g., as indicated between the "uncontracted" state and the contracted state), or having the largest peak-to-peak value. Such a pacing parameter adjustment can include at least one of a right ventricle pacing time adjustment such as determined using interval information associated with atrial activity (e.g., an intrinsic or paced contraction), or a left ventricle pacing time adjustment using interval information associated with at least one of atrial activity, or ventricular activity. For example, the left ventricle pacing time adjustment can be determined using information (e.g., timing, rate of change, or amplitude information) associated with paced or sensed atrial activity, left ventricle activity, or right ventricle activity.

A pacing site adjustment parameter can be used such as to select an optimal pacing site (e.g., having the shortest rise time, or the highest magnitude) using the information from at least a portion of the mechanical contraction waveform. Such a pacing site adjustment parameter can be determined using information from one or more implantable leads, such as to determine an optimal pacing site from one or more pacing sites included on a lead located near the left ventricle, the one or more pacing sites on a RV lead, or both.

Figure 16:
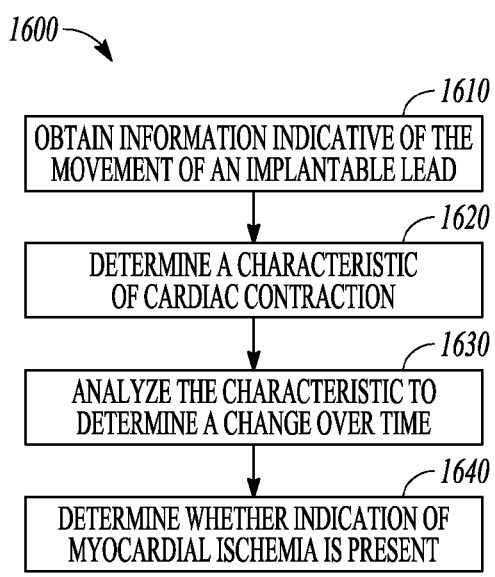
FIG. 16 illustrates generally a technique for detecting myocardial ischemia using information indicative of the movement of the implantable lead.

FIG. 16 illustrates generally a technique 1600 for detecting myocardial ischemia using information indicative of the movement of the implantable lead 145. At 1610, the IMD 105, such as by the myocardial ischemia detection circuit 173, can be configured to obtain information indicative of the motion of the implantable lead 145. Such information can include at least a portion of a mechanical contraction waveform indicative of a mechanical contraction of the heart (e.g., amplitude information, interval information, or rate of change information), as described above. In an example, the myocardial ischemia detection circuit 173 can be configured to monitor at least a portion of a cardiac contraction waveform indicative of a sinus rhythm. For example, the myocardial ischemia detection circuit 173 can be configured to use amplitude information such as to determine morphological features (e.g., a template) such as can be indicative of a mechanical contraction cycle during a normal sinus rhythm as depicted in FIG. 12.

At 1620, a characteristic (e.g., a peak magnitude, a peak-to-peak magnitude, a rise time, etc.) of the mechanical contraction waveform can be determined such as can be indicative of the mechanical contraction of the heart over one or more cardiac contraction cycles. In an example, the myocardial ischemia detection circuit 173 can be configured such as to determine contraction morphology associated with a normal mechanical contraction cycle, such as using one or more mechanical contraction waveforms, over one or more cardiac cycles At 1630, the myocardial ischemia detection circuit 173 can be configured such as to analyze contraction information using one or more criteria, such as can be indicative of myocardial ischemia. In an example, the contraction information can be analyzed, such as by the myocardial ischemia detection circuit 173, to determine a change over a duration of time (e.g., sudden but persistent changes). In an example, the myocardial ischemia detection circuit 173 can be configured to analyze contraction information from a current duration, a previous duration, or both.

At 1640, the myocardial ischemia detection circuit 173 can be configured such as to determine whether an indication of myocardial ischemia is present, such as using the analysis of the contraction information (e.g., a sudden, but persistent, morphological change). In an example, the myocardial ischemia detection circuit 173 can be configured such as to detect sudden or consistent changes over a specified duration, such as by using the contraction morphologies. For example, the myocardial ischemia detection circuit 173 can be configured to compare contraction morphology from a first duration to contraction morphology of a second duration.

In an example, the contraction morphology can be determined using a central tendency (e.g., an average, a mean, a median, etc.) of the contraction morphology information from previous analyses. In an example, the one or more contraction morphologies, such as determined by the myocardial ischemia detection circuit 173, can be compared using information about the area between contraction morphology from a first duration and contraction morphology from a second duration. Such an area can be compared to a criterion (e.g., a threshold) such as to indicate ischemia when the area meets the criteria (e.g., exceeds the threshold).

In an example, the myocardial ischemia detection circuit 173 can be configured such as to analyze the one or more mechanical contraction signals at a specified time of day. In an example, the myocardial ischemia detection circuit 173 can be configured such as to compare a contraction morphology associated with the current duration to one or more of the contraction morphologies over a recent duration. In an example, the myocardial ischemia detection circuit 173 can be configured to analyze the one or more contraction morphologies associated with one or more durations, such as in response to a physiologic signal (e.g., an activity level signal) such as obtained by the sensing circuit 130. Such contraction morphologies can be compared in response to a signal indicative of at least one of a low activity level or a low heart rate.

In an example, the myocardial ischemia detection circuit 173 can be configured to filter or selectively obtain the mechanical contraction waveform such as to exclude a mechanical contraction cycle indicative of an abnormal beat (e.g., a premature atrial contraction, a premature ventricular contraction, etc.). In an example, the myocardial ischemia detection circuit 173 can be configured to analyze portions of one or more mechanical contraction waveforms corresponding to a specified range of heart rates.

Figure 17:
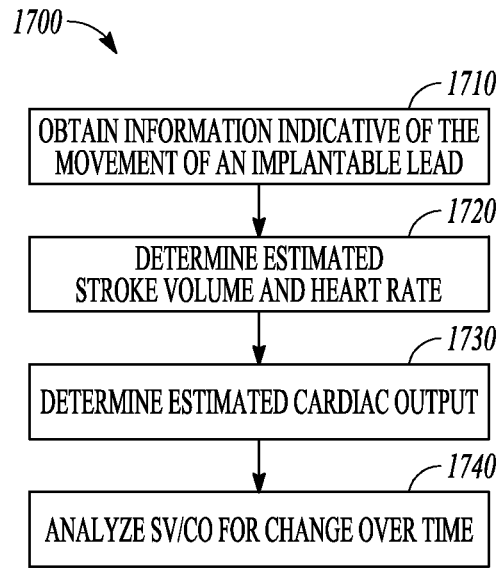
FIG. 17 illustrates generally a technique to determine at least one of stroke volume or cardiac output using information indicative of the movement of the implantable lead.

FIG. 17 illustrates generally a technique 1700 to determine stroke volume or cardiac output using indicative of the movement of the implantable lead 145. At 1710, the IMD 105, such as by the SV/CO monitor circuit 123, can be configured to obtain information indicative of the motion of the implantable lead 145. Such information can include at least a portion of a mechanical contraction waveform indicative of a mechanical contraction of the heart (e.g., amplitude information, interval information, or rate of change information), as described above.

At 1720, the information indicative of the motion of the implantable lead 145 can be analyzed such as to determine at least one of an estimated SV or a heart rate. Such a SV can be estimated such as by using amplitude information such as can indicate a change in mechanical contraction strength (e.g., an increase or decrease in amplitude). In an example, contraction strength can be related to an enlargement of the heart or increased stiffness of at least a portion the heart. In an example, the SV/CO monitor circuit 123 can be configured to estimate a SV, such as using information including an area under the curve of the one or more mechanical contraction waveforms during one or more cardiac contraction cycles. In an example, the area under the curve of the one or more mechanical contraction waveforms can be determined using a central tendency (e.g., an average, a median, etc.) of the area under the curve of the one or more mechanical contraction waveforms during the one or more cardiac contraction cycles. In an example, the SV/CO monitor circuit 123 can be configured to estimate a SV, such as by using difference information between a maximum and a minimum amplitude of each of the one or more mechanical contraction waveforms, such as obtained from the one or more implantable leads 145. In an example, the difference information can include a central tendency (e.g., an average, a median, etc.) of the area under the curve of the one or more mechanical contraction waveforms during the one or more cardiac contraction cycles.

A heart rate can be estimated such as by using interval information, such as an interval between two similar features (e.g., loci at or near a peak) associated with successive or adjacent mechanical contraction cycles. In an example, the heart rate can include a central tendency of the contraction rate estimated for two or more mechanical contraction cycles. In an example, the heart rate can be determined from a signal indicative of cardiac electrical activity, such as obtained from the sensing circuit 130. In an example, the SV/CO monitor circuit 123 can be configured to analyze the one or more mechanical contraction signals continuously, or at a specified interval (e.g., once per minute, once per hour, daily, etc.). In an example, the SV/CO monitor circuit 123 can be configured to analyze the one or more mechanical contraction signals after a trigger condition occurs, such as a physiologic signal from the subject meeting a criterion. At 1730, an estimated CO can be determined such as by using the estimated SV and the heart rate (HR), such as by using CO=SV×HR.

At 1740, SV and CO can be monitored, such as to detect a change to either SO or CO over time. In an example, the SV/CO monitor circuit 123 can be configured to determine information corresponding to a relative change of one or more of SV or CO. In an example, an estimated SV associated with a first duration can be compared with at least one estimated SV associated with a second duration, such as to determine a relative change in SV. In an example, an estimated CO associated with a first duration can be compared with at least one estimated CO associated with a second duration, such as to determine a relative change in CO.

Figure 18:
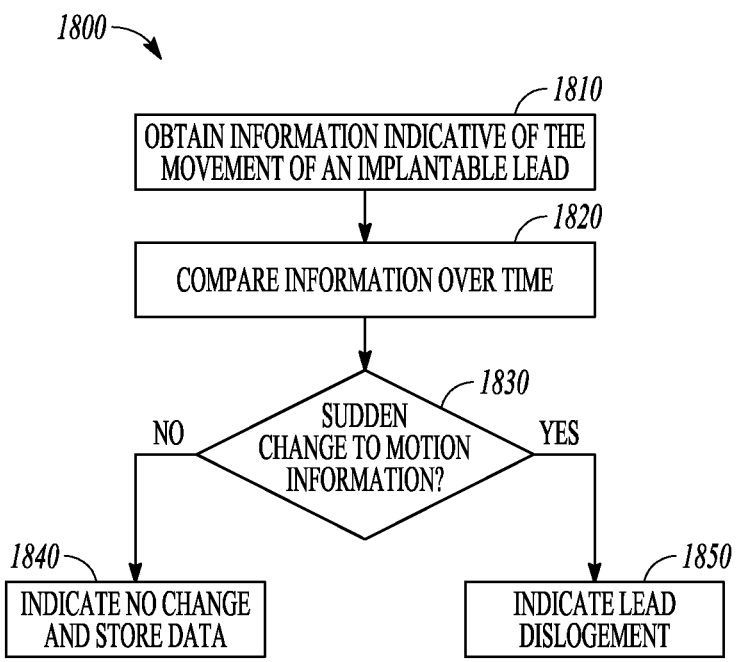
FIG. 18 illustrates generally a technique to detect lead dislodgement using information indicative of the movement of the implantable lead.

FIG. 18 illustrates generally a technique 1800 to detect lead dislodgement using information indicative of the movement of the implantable lead 145. At 1810, the IMD 105, such as by the lead dislodgement monitor circuit 143, can be configured to obtain information indicative of the motion of the implantable lead 145. Such information can include at least a portion of a mechanical contraction waveform indicative of a mechanical contraction of the heart 205 (e.g., amplitude information, interval information, or rate of change information), as described above. In an example, lead dislodgment monitor 143 can be configured to determine motion information from the mechanical contraction waveform, such as by analyzing the waveform at a specified interval (e.g., once per day). In an example, information indicative of a normal sinus rhythm, such as template associated with a portion of a mechanical contraction waveform indicative of a matured lead (e.g., secured to fibril tissue of an endocardium, as described above).

At 1820, the LMI signal of a current cycle can be compared to the template indicative of a normal sinus rhythm such as to determine a sudden change in a motion profile (e.g., peak information, peak-to-peak information, rise time, fall time, magnitude morphology, etc.). In an example, the lead dislodgement monitor 143 can be configured such as to compare first information (e.g., a portion of mechanical contraction waveform morphology) from a first time to second motion information at a second time to determine an lead dislodgement (e.g., sudden change in motion). At 1830, if the lead dislodgment monitor 143 detects a change in the motion information from the implantable lead 145 (e.g., having a difference greater than a threshold), then the lead dislodgment monitor 143 can indicate a lead dislodgment at 1850. Otherwise, at 1840, the lead dislodgement monitor can indicate that no dislodgement was detected. Such indications that no dislodgement was detected, the portion of the mechanical contraction waveform indicative of the motion of the implantable lead can be stored, or otherwise used (e.g., averaged with previously stored information), such as to determine an indication of a stable or mature lead.

Figure 19:
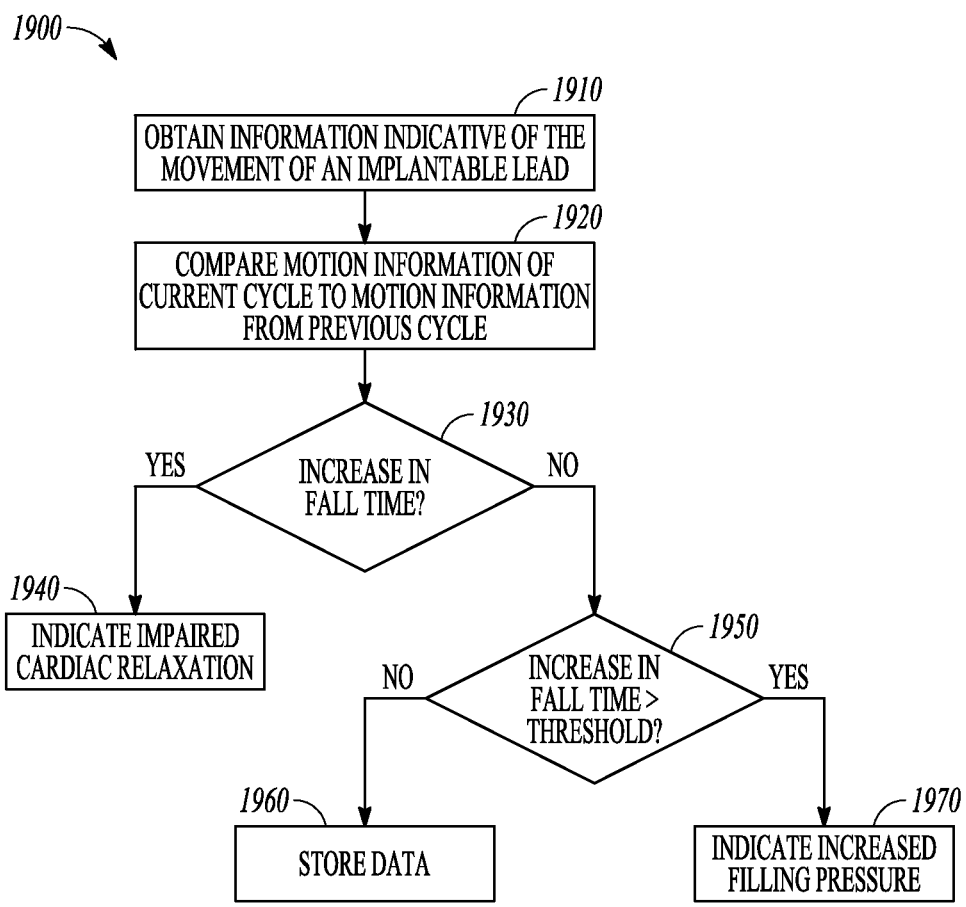
FIG. 19 illustrates generally a technique to monitor cardiac relaxation using information indicative of the movement of the implantable lead.

FIG. 19 illustrates generally a technique to monitor cardiac relaxation using information indicative of the movement of the implantable lead 145. At 1910, the processor circuit 190, such as by using the cardiac relaxation monitor circuit 183, can obtain information representative of the motion of the implantable lead 145, such as determined above. At 1920, the cardiac relaxation monitor circuit 183 can compare the motion information, such as a rate of change of the magnitude during a transition from a contracted state to an "uncontracted" state. For example, the cardiac relaxation monitor circuit 183 can be configured to compare rate of change information, such as measured during a current duration, to rate of change information such as determined during one or more previous durations. For example, previously measured rate of change information can include fall time information during a normal sinus rhythm (e.g., during a single mechanical contraction cycle, or a using a central tendency over two or more mechanical contraction cycles).

At 1930, the cardiac relaxation monitor circuit 183 can determine whether the fall time information has increased. For example, the cardiac relaxation monitor circuit 183 can be configured to compare current fall time information to previous fall time information (e.g., corresponding to at least one previous duration), such as can indicate a reduction in the ability of the myocardial tissue to relax when current fall time information exceeds the previous fall time information. If at 1930, an increase in fall time is detected, then an indication of impaired cardiac relaxation can be indicated, such as by the cardiac relaxation monitor circuit 183 at 1940. If, however, no change was indicated (e.g., such as the fall time information remaining within a specified range), flow continues to 1950.

At 1950, an increase in fall time can be detected such as by comparing the current fall time to a criterion. If the fall time meets the criterion (e.g., exceeds a threshold), an indication of increased filling pressure, such as to the pulmonary veins or the left atrium, can be indicated at 1970, such as by the cardiac relaxation monitor circuit 183. If, however, the fall time does not meet the criterion, then the fall time information can be stored, such as for use in future comparisons, at 1960.

In an example, the cardiac relaxation monitor circuit 183 can be configured such that a portion of the mechanical contraction waveform can be measured at a specified interval (e.g., once per day). For example, the cardiac relaxation monitor can determine, such as at a specified time, a fall time (e.g., a portion of a signal between 10% of the peak value and 90% of the peak value). In an example, the cardiac relaxation monitor circuit 183 can be configured to compare a portion of a mechanical contraction waveform associated with a current duration to a corresponding portion of the mechanical contraction waveform associated with at least one duration measured previously. In an example, the cardiac relaxation monitor circuit 183 can be configured to determine an increase in fall time such that the difference between the fall time of the current duration and the fall time of the at least one previous duration meets a criterion (e.g., exceeds a threshold).

ADDITIONAL EXAMPLES

Generally, a healthy heart can provide at least two distinct heart sounds. The first sound, "S1," is typically produced by the closing of the atrioventricular valve leaflets. The second sound, "S2," is typically produced by the closing of the semilunar valve leaflets. In a clinical setting, these events can be detected such as through cardiac auscultation by an examiner, using a stethoscope.

In some individuals, various cardiac conditions can cause additional detectable mechanical vibrations, though these may or may not be audible to the examiner. For example, a heart murmur can occur when blood is flowing harder or faster than in an otherwise healthy individual. Such a murmur can indicate a serious heart problem or merely a benign cardiac event. In another example, an "S3" sound, also known as a protodiastolic gallop, can indicate a failing left ventricle. An "S4" sound, also known as presystolic gallop, can sometimes be detected in patients exhibiting restrictive cardiomyopathy.

In addition to vibrations or sounds indicative of heart function, blood flowing through blood vessels can also produce detectable vibrations useful for diagnosis and assessment of various medical conditions. The location, velocity, and pressure of blood flow are variables that can be assessed by detection of such vibration, among other variables. Thus, mechanical vibration monitoring capabilities can be included in an implantable or an ambulatory medical device, such as to store such information for later review or analysis, or to respond to such mechanical information. For example, an individual with an implantable medical device, such as a pacemaker, can benefit from mechanical vibration monitoring, including heart sound monitoring. Such monitoring can be used for diagnosis, or an initiation or adjustment of treatment. By identifying a mechanical vibration (e.g., including one or more heart sounds), therapy can be tailored to an individual's needs, or heart sound abnormalities can be provided to a caregiver for assessment or treatment.

Implantable acoustic and mechanical transducers can be used in detecting heart and blood mechanical vibrations (e.g., including one or more heart sounds). However, the resulting acoustic information from these transducers can produce a low signal level that can be degraded by extraneous noise. Furthermore, devices having a dedicated acoustic or mechanical transducer can require additional sensors within, on, or attached to the implantable or ambulatory device, such as resulting in a greater surface area, physical volume, or number of interconnects as compared to a comparable implantable device lacking such a dedicated acoustic or mechanical transducer.

The present inventor has recognized, among other things, that mechanical information indicative of cardiac, blood, or vascular motion can be detected using a motion of one or more conductors electrically coupled to the ambulatory or implantable device. For example, the present inventors have also recognized that an implantable lead electrically and mechanically tethered to an implantable or ambulatory medical device can provide information indicative of the motion of the lead, such as using one or more electrical measurements as described in the following examples, such as to detect cardiac, blood, or vascular motion. Such information indicative of motion can also be used to time or to verify the effectiveness of a cardiac therapy (e.g., electrostimulation), in addition to diagnosing one or more cardiac conditions.

An ambulatory medical device can include an excitation circuit configured to be electrically coupled to an implantable lead, the excitation circuit configured to provide a non-tissue-stimulating first signal to the implantable lead when the implantable lead is located at or near a tissue site. In an example, the system can include a detection circuit configured to be electrically coupled to the implantable lead and configured to receive a second signal, in response to the first signal, from the implantable lead, the second signal determined at least in part by a motion of the implantable lead.

Figure 20:
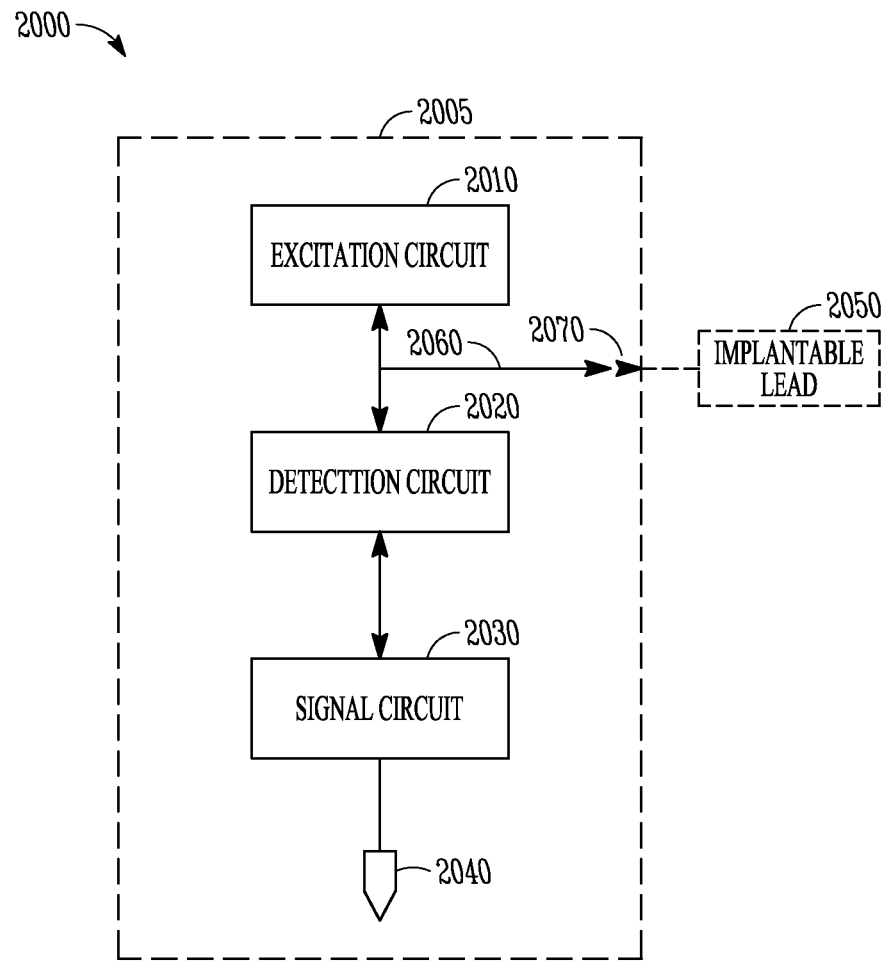
FIG. 20 illustrates generally an example of a system comprising an ambulatory medical device that can include an excitation circuit, a detection circuit, a coupling to an implantable lead, a signal processor, or an output.

FIG. 20 is a diagram illustrating generally an example of a system 2000 comprising an ambulatory medical device 2005 that can include an excitation circuit 2010, a detection circuit 2020, a signal processor 2030, an output 2040, an interconnect 2060, or a lead coupling 2070. In an example, an implantable lead 2050 can be coupled to the lead coupling 2070. One or more of the excitation circuit 2010, detection circuit 2020, signal processor 2030, output 2040, or interconnect 2060 can be realized on or within a commonly shared substrate, such as on a commonly-shared integrated circuit, module, circuit board, or the like. In another example, each block can be included in a physically separate ambulatory device, such devices coupled as shown in the example of FIG. 20, such as using one or more wired or wireless communicative couplings.

In the example of FIG. 20, the ambulatory medical device 2005 can include a cardiac stimulator, such as including pacing or cardiac resynchronization therapy (CRT) circuitry configured to deliver pacing or resynchronization energies to cardiac tissue. In an example, the ambulatory medical device 2005 can include a neural stimulator device, such as to provide electrical, mechanical, optical, acoustic, or chemical stimulation to one or more neural targets.

In the example of FIG. 20, the excitation circuit 2010 can be coupled to a detection circuit 2020. The excitation circuit 2010 generally provides an excitation energy, such as including a first signal. In an example, the first signal can include an oscillating electrical signal, such as a time-varying voltage or current. In an example, the first signal can include a pulsed electrical signal, such as including one or more current or voltage pulses including a specified amplitude, duration, pulse repetition rate, duty cycle, or morphology, among other parameters. In an example, the excitation circuit 2010 can be coupled to the lead coupling 2070 via interconnect 2060, such as using a header or other connector included as a portion, part, or component of the ambulatory medical device 2005.

In the example of FIG. 20, an implantable lead 2050 can be coupled to the lead coupling 2070. For example, the implantable lead 2050 can include one or more conductors. In an example, the implantable lead 2050, such as coupled to the implantable lead coupling 2070, can be located at a site within or on the body (e.g., including one or more surface, subcutaneous, or intravascularly-located electrodes or conductors). In an example, the implantable lead 2050 can be implanted or otherwise place within a body, such as within or near a heart, either temporarily or more permanently, such as for ambulatory monitoring or therapy delivery.

In the example of FIG. 20, the detection circuit 2020 can be coupled both to a signal processor 2030 and the lead coupling 2070 via a commonly-shared interconnect 2060. In an example, the implantable lead 2050, or an external lead, can be coupled to the lead coupling 2070. In an example, the detection circuit 2020 can be configured to receive a second signal provided by the implantable lead 2050. For example, the detection circuit 2020 can be configured to interpret or processes the first signal, such as by providing the first signal to the implantable lead 2050 before or during receiving the second signal.

In the example of FIG. 20, the detection circuit 2020 can be configured to receive a second signal, such as from the implantable lead 2050 via the lead coupling 2070 and the interconnect 2060 (e.g., in response to the first signal). In an example, the detection circuit 2020 can be configured to interpret and process a received second signal before transmitting the received second signal to the signal processor 2030. For example, the detection circuit 2020 can be configured to determine a first characteristic of the second signal (e.g., information about an amplitude, frequency, noise floor, signal-to-noise ratio, or one or more other characteristics). In an example, the amplitude characteristic of the second signal can be compared to a threshold value, and the result of the comparison can be used to determine if the received second signal can be further processed by the signal processor 2030. For example, if the amplitude of the second signal meets or exceeds a threshold value, the detection circuit 2020 can be configured to transmit the second signal to the signal processor 2030 for further analysis. Conversely, if the amplitude of the second signal is below the threshold value, the detection circuit can withhold transmission of the second signal or otherwise indicate to the signal processor 2030 that further analysis should be withheld (e.g., if the second signal is so low in amplitude that extraction of motion information would be difficult).

In the example of FIG. 20, the signal processor 2030 can be coupled to the detection circuit 2020 and the output 2040. In an example, the signal processor 2030 can be configured to receive information derived from the second signal. The signal processor 2030 can be configured to extract from the second signal information indicative of motion of the implantable lead 2050. Such motion of the implantable lead 2050 can include a physical displacement of any constituent element of implantable lead 2050 with respect to an equilibrium position. In an illustrative example, the implantable lead 2050 can experience a physical displacement because the implantable lead is mechanically coupled to a vibrating tissue, such as implanted within or near contractile tissue in the heart. In an example, the information indicative of motion of the implantable lead 2050 can include audible or acoustic information such as provided by a heart sound, or other higher or lower-frequency mechanical information not necessarily within the audible frequency spectrum.

In an example, information indicative of motion of the implantable lead 2050 can include impedance information, such as including a change in lead impedance determined at least in part by mechanically coupling cardiac or vascular mechanical vibrations to the implantable lead 2050. For example, impedance information can be interpreted by the signal processor 2030 to detect, classify, or monitor one or more physiological events. Such physiological events can include the closing of the atrioventricular or semilunar valve leaflets in the heart.

In the example of FIG. 20, the output 2040 can be coupled to the signal processor 2030. In an example, the output 2040 can receive information from the signal processor 2030. The received information can be passed through an output 2040 to one or more other portions, parts, or components of the ambulatory medical device 2005. In an example, the output 2040 can be coupled to another device via a wired or wireless communicative connection (e.g., to transfer information to one or more other implantable or ambulatory devices, or to an external assembly). In an example, the signal processor 2030 can perform one or more signal adjustments such as impedance or level adjustments, among others, before providing the lead motion information to the one or more other portions via the output 2040.

Figure 21:
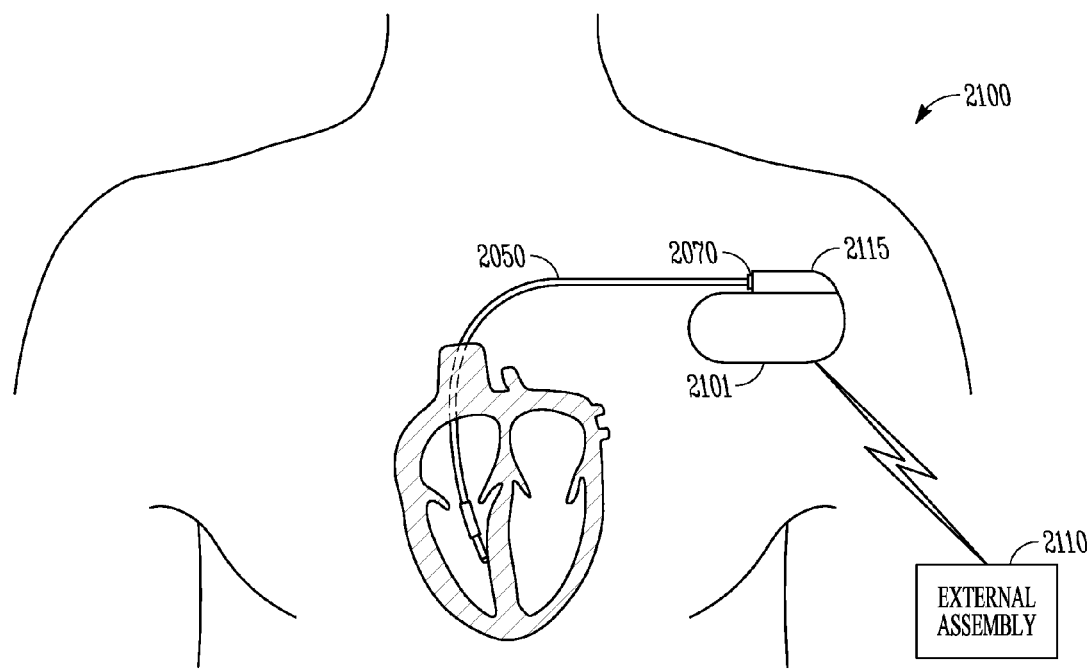
FIG. 21 illustrates generally an example of a portion of a system that can include an implantable medical device, an implantable lead, or a communicative coupling between the implantable medical device and an external assembly.

FIG. 21 illustrates generally an example of a system 2100 that can include an implantable medical device 2105. In this example, the implantable medical device 2105 can include one or more implantable lead couplings, such as a lead coupling 2070. In certain examples, the implantable medical device 2105 includes a hermetically-sealed or similar housing 2101 coupled to the implantable lead coupling 2070. For example, the housing 2101 can include titanium or other biocompatible material, such as one or more other conductive materials.

In the example of FIG. 21, the system 2100 can include an implantable lead 2050 implanted in a heart, such as implanted endocardially via an intravascular route from one or more of a subclavian vein or a femoral artery. In an example, the implantable lead 2050 can include one or more conductors, such as one or more concentric or laterally-separated conductors. In an example, one or more conductors can include a braided or coiled shield conductor. The one or more conductors can be insulated from one another and from the environment surrounding the implantable lead 2050, such as using a silicone or a poly-ether-ether-ketone (PEEK) insulation, among others. In an example, the conductors to be used for mechanical vibration sensing can be selected based on measurement of RF coupling or an AC impedance between the conductors. Such RF coupling or impedance measurements can be used to determine a conductor pair or combination likely to exhibit higher mechanical vibration sensitivity than other pairs or combinations. Such measurements can also be used to find a conductor pair or combination including an input impedance most closely matched to a conjugate of the output impedance of one or more of a detection circuit, excitation circuit, or interconnect as shown in FIG. 20, and FIGS. 22-24.

In an example, the implantable medical device 2105 can be configured to communicate with the external assembly 2110. The communication between the implantable medical device 2105 and an external assembly 2110 can be wireless or through a wired connection, or using one or more other communication schemes (e.g., using an optical communication link or an acoustic communication link, among others). For example, the external assembly 2110 can be a portion or part of a patient management system, such as including or in communication with one or more remote or web-based clients communicatively coupled to one or more servers comprising medical and patient databases.

In an example, the implantable medical device can include one or more of a pacemaker, a defibrillator, an implantable monitor, a drug delivery device, a cardiac resynchronization therapy device, a neural stimulation device, or one or more other implantable assemblies configured to monitor a person or configured to provide one or more treatments to the person. Such monitoring or treatment can include, among others, electrostimulation of tissue such as cardiac tissue, or electrical monitoring of muscular or cardiac activity, among others.

Figure 22:
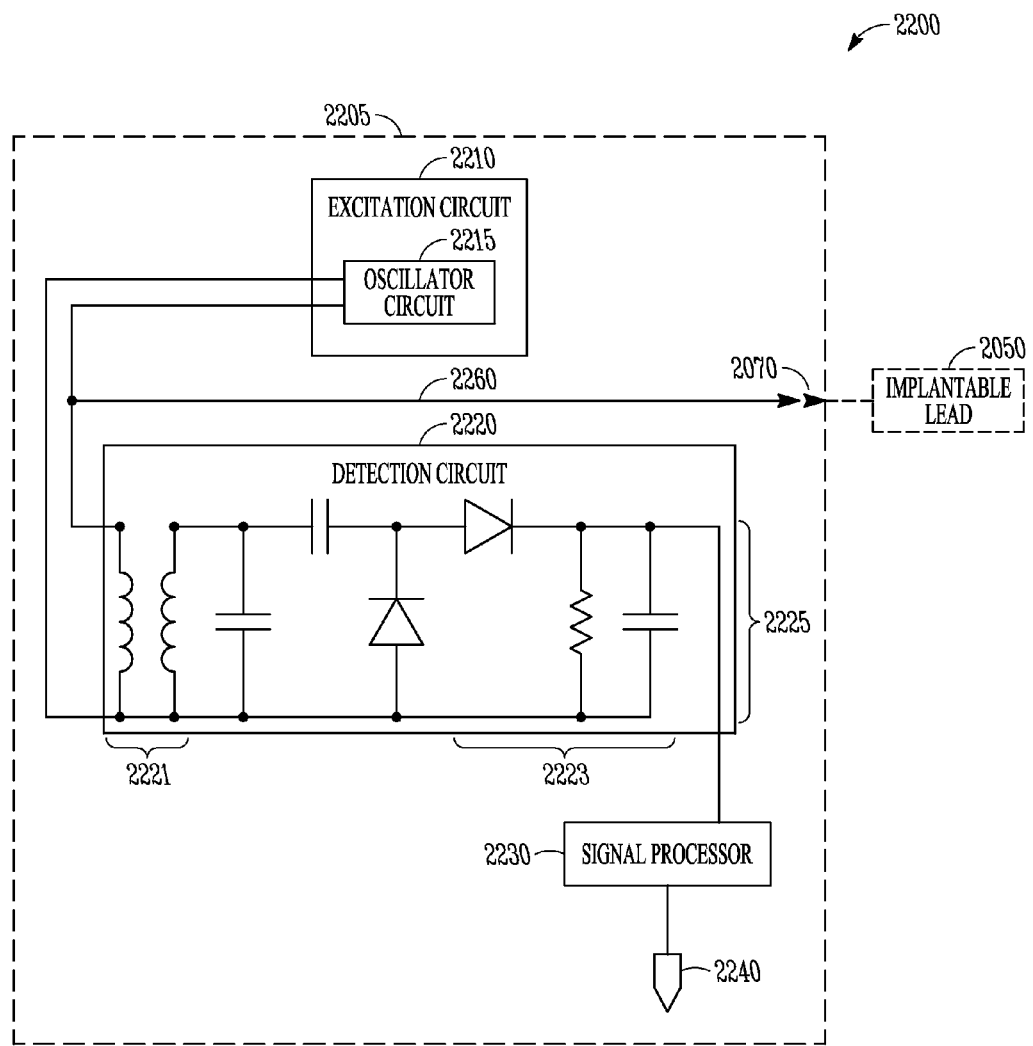
FIG. 22 illustrates generally an example of a portion of a system comprising an excitation circuit that can include an oscillator circuit, a detection circuit, a coupling to an implantable lead, a signal processor circuit, or an output.

FIG. 22 illustrates generally an example of a system 2200 that can include an ambulatory medical device 2205, such as including an implantable device as shown in the example of FIG. 21, an externally-worn assembly, or a combination of implantable and external portions. In this example, an excitation circuit 2210 can include an oscillator circuit 2215 such as configured to provide a first signal. In an example, the oscillator circuit can provide an RF signal (e.g. from about 10 to about 30 MHz), such as including a specified current level.

In an example, an interconnect 2260 can be coupled to one or more of the excitation circuit 2210 or a detection circuit 2220. In this example, the first signal (e.g., an excitation current signal) can be provided by the excitation circuit 2210 to develop a voltage across two conductors included in the lead coupling 2070 via the interconnect 2260. For example, the first signal can include one or more current signals provided to one of the conductors, and received from the other conductor. The detection circuit 2220 can be configured to receive a second signal (e.g. a developed voltage) across the lead coupling 2070.

In an example, the detection circuit 2220 can include a demodulation circuit 2225. The demodulation circuit 2225 can include an envelope detector 2223 or a tuned resonant transformer 2221 that can be impedance-matched to one or more other attached components. In an example, the envelope detector 2223 can demodulate or extract a relatively low frequency component of time-varying voltage from the second signal, such as containing information indicative of motion of an implantable lead 2050 attached to the lead coupling 2070. The demodulation circuit 2225 can be coupled to a signal processor 2230. In an example, the signal processor 2230 can be configured to extract information indicative of motion of the implantable lead 2050, such as including protodiastolic or presystolic gallop sounds, or other mechanical vibrations such as indicative of blood flow, or pressure, among others.

In an example, additional elements can be included in the system 2200 to enhance sensitivity or provide additional mechanical event information. For example, multiple implantable leads can be implanted in multiple locations within or on a body and lead motion information can be collected from one or more of the multiple locations. For example, a second lead comprising at least one electrical conductor can be coupled to a second lead coupling, or the implantable lead 2050 can include multiple electrical conductors that can be coupled to one or more lead couplings. In an example, one or more mechanical events can provide a change in the impedance of the system comprising the multiple conductors, such as detectable using the second signal provided in response to the first signal. In an example, the signal processor 2230 can be coupled to an output 2240, and extracted information indicative of motion of the implantable lead 2050 can be communicated to another assembly via the output 2240. Such other assemblies can include, among others, an additional ambulatory medical device located internally or externally to a body, or an external assembly 2110, a combination of one or more implantable and external assemblies.

Figure 23:
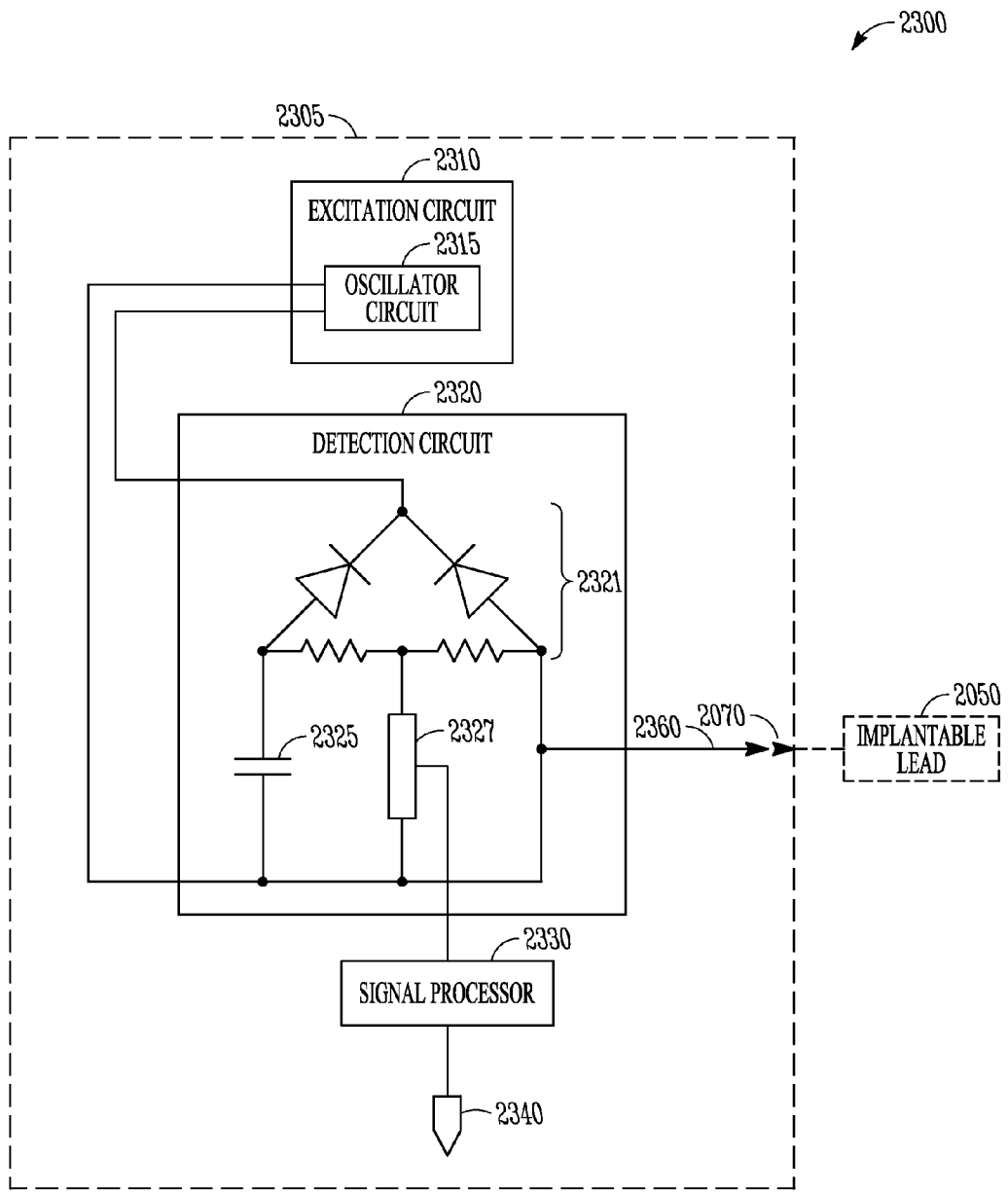
FIG. 23 illustrates generally an example of a portion of a system comprising an excitation circuit that can include an oscillator circuit, a detection circuit comprising a coupling to an implantable lead and a bridge circuit, a signal processor circuit, or an output.

FIG. 23 illustrates generally an example of a system 2300 including ambulatory medical device 2305, such as including an implantable device as shown in the example of FIG. 21, an externally-worn assembly, or a combination of implantable and external assemblies. In this example, an excitation circuit 2310 can include an oscillator circuit 2315 configured to provide a first signal, such as provided to a portion of a detection circuit 2320. In an example, an interconnect 2360 can be coupled to the detection circuit 2320. The detection circuit 2320 can include a bridge circuit 2321, a capacitive element 2325, or an envelope detector 2327, among other components or portions. In the example of FIG. 23, the sensitivity of detection circuit 2320 can vary with respect to a specified excitation frequency. In an illustrative example, the oscillator circuit 2315 can provide a first signal including a sine wave signal with a frequency of around 100 KHz to 1 MHz (or including one or more other frequencies). The bridge circuit 2321 can include one or more diodes or other rectifiers exhibiting low forward resistance, such as one or more germanium diode (e.g. type 1N60). In this example, the bridge circuit 2321 can include resistors of about the same values. The implantable lead 2050 can provide a capacitance, and the capacitive element 2325 can include a specified capacitance value approximately equal to the capacitance provided by the implantable lead 2050 when implantable lead 2050 is in equilibrium (e.g., relatively motionless, or subject to a specified baseline of vibration or motion). The capacitance provided by the implantable lead 2050 can be one or more capacitances provided between two or more conductors, such as included in a single implantable lead 2050, or between conductors respectively included in two or more implantable leads. Generally, the one or more capacitances can be provided by a combination of multiple conductors, and such capacitances can be combined in a series or parallel configuration, such as each including a capacitance contribution from one or more pairs of conductors. In an example, the capacitance can be provided between conductors of physically separate implantable leads. Such lead capacitance can vary in proportion or with respect to motion or vibration coupled to the lead such as from surrounding tissue or blood motion. In an example, the envelope detector 2327 can include a relatively high input impedance to achieve a specified sensitivity of the system 2300. The envelope detector 2327 can include one or more of a diode or rectifier detector, or a synchronous detector, such as to improve noise rejection, selectivity, or one or more other characteristics.

In an example, a signal processor 2330 can be configured to receive a signal from the detection circuit 2320, such as provided at least in part by the envelope detector 2327. For example, the signal processor 2330 can be configured to extract information from the received voltage signal indicating a motion of an implantable lead 2050. In an example, the signal processor 2330 can include a low pass filter circuit to process the signal received from the detection circuit 2320. In an example, the signal processor 2330 includes an amplification circuit, or one or more other circuits or components, such as to amplify the received signal. In an example, the signal processor 2330 can include an analog-to-digital converter to convert the information indicative of motion into a digital data signal, such as for storage, further processing, or for presentation to a caregiver or clinician.

In an example, an output 2340 can be configured to receive a signal from the signal processor 2330, and the output 2340 can be configured to transfer the information indicative of motion of the implantable lead 2050 to another implantable or ambulatory medical device, or to an external assembly such as the external assembly 2110 using a wireless or wired communicative coupling. In an example, the output 2340 can be configured to communicate with one or more external assemblies including one or more tabletop or handheld electronic devices (e.g. a cell phone, smart phone, tablet, laptop, or personal digital assistant (PDA), among others), in addition to or instead of one or more external assemblies dedicated for medical diagnosis or assessment.

In an illustrative example, one or more of the detection circuit 2320 or the signal processor 2330 can receive a second signal in response to the first signal, and the second signal can include a portion in-phase with the first signal, and a second portion in quadrature (e.g., ninety degrees out of phase) with the first signal. In this illustrative example, the detection circuit 2320 or the signal processor 2330 can use the quadrature component of the second signal to determine the change in capacitance of the lead system, thus canceling out the effect of the resistive component of an impedance presented by the lead 2050 to the measurement circuit.

Figure 24:
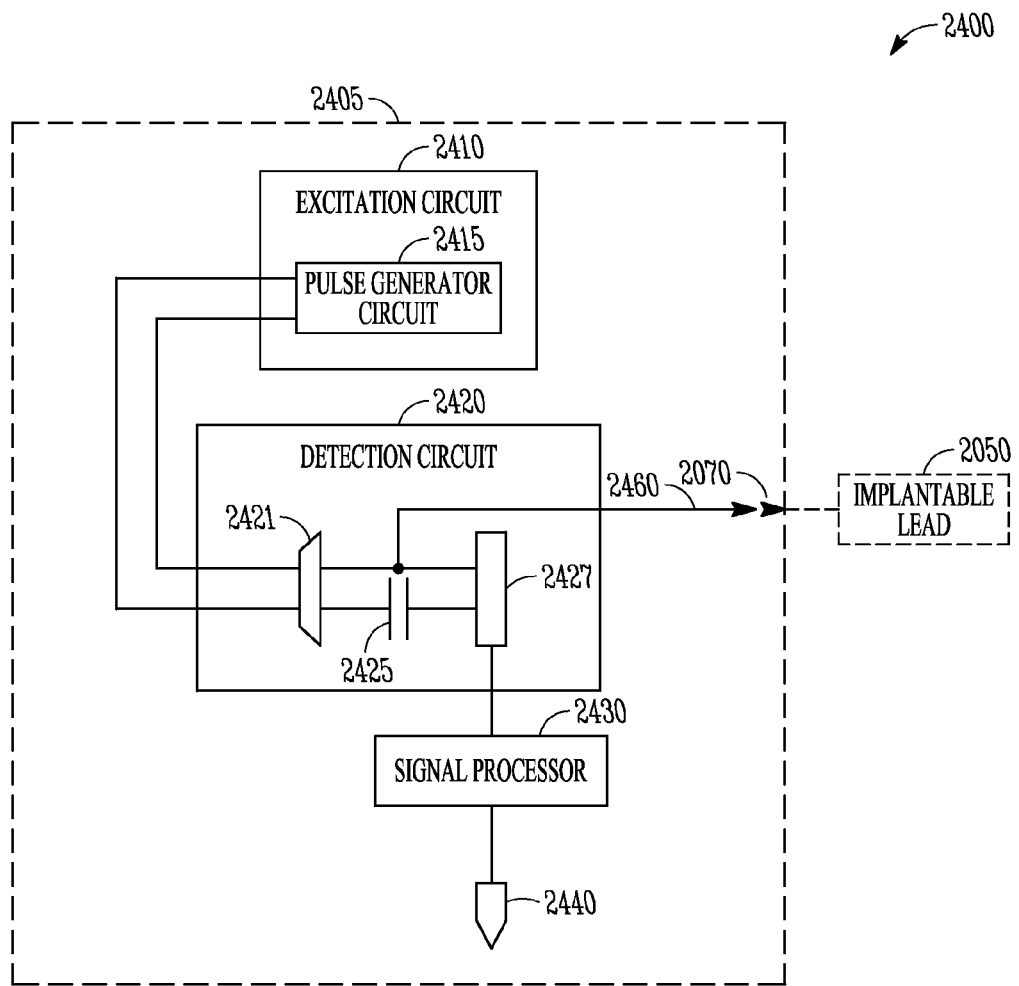
FIG. 24 illustrates generally an example of a portion of a system that can include an excitation circuit such as including a pulse generator circuit, a detection circuit including a coupling to an implantable lead and a voltage detector, a signal processor circuit, or an output.

FIG. 24 illustrates generally an example of a system 2400 including ambulatory medical device 2405, such as including an implantable device as shown in the example of FIG. 21, or an externally-worn assembly. In this example, an excitation circuit 2410 can include a pulse generator circuit 2415 configured to provide a first signal, and a detection circuit 2420. In an example, the detection circuit 2420 can include a multiplexer 2421, a capacitive element 2425, or a voltage detector 2427. In an example, the multiplexer 2421 can be configured to select among one or more inputs, wherein the inputs can be coupled to the excitation circuit 2410, or another signal-generating source. In an example, the multiplexer 2421 can be under the control of the detection circuit 2420 or another component of the ambulatory medical device 2405. An interconnect 2460, the voltage detector 2427, or a lead coupling 2070, among other components, can be coupled to the multiplexer 2421.

One or more portions of the system 2400, such as the interconnect 2460, multiplexer 2421, or voltage detector 2427, can be implemented on a rigid or flexible circuit board, such as including one or more application specific integrated circuits, among other components. In an example, the lead coupling 2070 can be implemented via an electrical and mechanical interconnect in a header block that can be attached to the housing 2101 of an implantable medical device housing, such as shown in FIG. 21. The housing 2101 of the implantable medical device itself can be used as one of the conductors for capacitance or impedance measurement.

In an example, the excitation circuit 2410 can be coupled to the multiplexer 2421. In an example, the multiplexer 2421 can be configured to couple the excitation circuit 2410 to each of the interconnect 2460 and the capacitive element 2425, concurrently or successively. In an example, the concurrent or successive coupling can be performed by the multiplexer 2421 under the direction of a logic circuit included as a portion of the detection circuit 2420. For example, the logic circuit can include a counter or timer such as to provide one or more counts or durations to be used by the logic circuit to switch the state of the multiplexer 2421, such as after a specified duration of time elapses as indicated by the counter or timer. In an example, the logic circuit can be configured to count a number of pulses provided by the excitation circuit 2410. In this example, the logic circuit can be configured to switch the state of the multiplexer 2421, such as after a specified count of a number of pulses is met or exceeded as indicated by the counter.

In the example of FIG. 24, the multiplexer 2421 can be configured to couple the first signal to a first capacitance provided by implantable lead 2050. In an example, a first voltage can be developed across the first capacitance in response to the first signal. A second signal that includes the first voltage can be received by the voltage detector 2427. In this example, a signal processor 2430 can receive the output of the voltage detector 2427. In an example, the signal processor 2430 can be configured to compare the received signal from the first capacitance to a threshold voltage (e.g., monitoring a charging of the first capacitance to reach the specified threshold voltage).

In the example of FIG. 24, the multiplexer 2421 can be configured to couple the first signal to a second capacitance provided by the capacitive element 2425 (e.g., a "reference capacitance," charged using the same or a similar first signal). In an example, the multiplexer 2421 can be configured to provide the first signal to each of the first capacitance and second capacitance, either separately, sequentially, or in combination. In an example, a second voltage can be developed across the second capacitance in response to the first signal. In an example, the second signal that includes the second voltage can be received by the voltage detector 2427. In this example, a signal processor 2430 can receive the output of the voltage detector 2427. In an example, the signal processor 2430 can be configured to compare the received signal from the second capacitance to the specified threshold voltage (e.g., monitoring a charging of the second "reference" capacitance to reach the specified threshold voltage).

In the example of FIG. 24, the signal processor 2430 can be configured to determine a relative indication of information (e.g., a ratio, a difference, etc.) derived from one or more of the first or second voltages measured with respect to the first or second capacitances. Coupling of mechanical vibration to the implantable lead 2050, or other motion of the lead, can cause a detectable change in the capacitance of the lead. For example, the second signal received from the first capacitance can differ from the second signal received from the second capacitance in response to a similar excitation by the first signal. In this manner, a variation between a reference capacitance (e.g., provided by capacitive element 2425) and the capacitance of the lead can be used to provide information corresponding to motion of the implantable lead. In an example, capacitive element 2425 can include, among other things, an additional specified capacitance such as provided by a discrete capacitor, a second implantable lead, or combination of conductors, a number of interconnected implantable leads, or a capacitive transducer.

In the example of FIG. 24, the first signal can charge the first capacitance to a first specified threshold voltage, and a corresponding duration of the charge time can be determined (e.g., such as when the first capacitance is charged using a sequence of current pulses or a constant current). In an example, the voltage detector 2427 can be configured to receive the first voltage in response to the charging of the first capacitance. In this example, the signal processor 2430 can be configured to determine a duration of a first charge time, corresponding to a duration where the first voltage is between a lower threshold (e.g., around 0 Volts), and an upper threshold (e.g., the first specified voltage threshold). In an example, the signal processor 2430 can be configured to determine a duration of a second charge time, corresponding to a duration where the second voltage is between the lower and upper thresholds. If the capacitance of the capacitive element 2425 and the lead capacitance are roughly equal, the determined first and second charge times can be roughly equal, such as when the lead 2050 is at rest or equilibrium.

In the example of FIG. 24, the excitation signal (e.g., the first signal), can include a series of current pulses having a specified peak current level, duration, pulse repetition rate, duty cycle, etc. The signal processor 2430 can be configured to count a number of pulses delivered to the lead 2050, or to a capacitive element 2425. For example, the voltage detector 2427 can be configured to receive pulsed signals and the signal processor 2430 can be configured to count the received pulsed signals. In an example, the signal processor 2430 can be configured to count a first count of a number of pulses provided to the first capacitance, such as to reach the specified threshold voltage (e.g., the pulse count can be a proxy for a measurement of a charge time duration, such as when pulses of determinable width and level are used). In an example, the signal processor 2430 can be configured to extract from the first count an indication of lead motion, since the variation in the lead capacitance can provide a difference in a number of pulses needed to reach the specified threshold, such as compared with a baseline number of pulses corresponding to a lead at rest or in equilibrium.

In an example, the sensitivity of the system 2400 can be enhanced by using a comparison between a second capacitance (e.g., a reference capacitance or another pair or combination of lead conductors) and the capacitance of the lead 2050. The signal processor 2430 can be configured to count a second count of a number of pulses provided to the second capacitance (e.g., using a series of pulses of determinable width or level, as above). For example, the signal processor 2430 can be configured to extract from the first and second counts a relative indication of information that can indicate lead motion (e.g., a difference, or ratio, etc., between the first and second counts of pulses). In an illustrative example, the signal processor 2430 can measure multiple pulse durations and perform comparison operations, such as including using one or more techniques disclosed in Pelletier et al. U.S. Pat. No. 4,011,500 entitled "PHYSICAL DISPLACEMENT SENSING WITH DIFFERENTIAL CAPACITOR," which is hereby incorporated by reference in its entirety, including its disclosure of using a differential capacitor to detect a physical displacement.

In an example, an output 2440 can be configured to receive information from the signal processor 2430, and to transfer such information to one or more other portions of the ambulatory medical device 2405, or to communicate with an external assembly.

Figure 25:
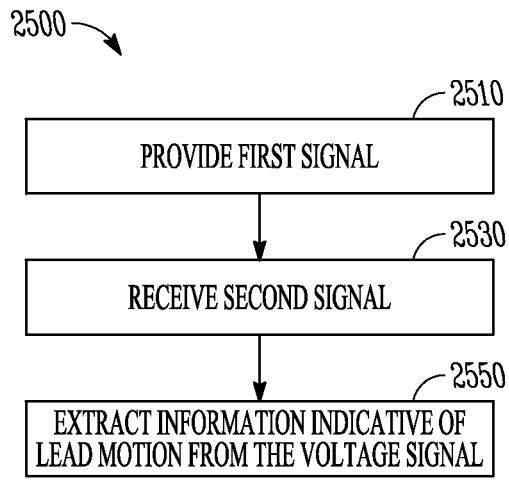
FIG. 25 illustrates generally an example that can include providing a first signal, receiving a second signal, or extracting information indicative of lead motion from the second signal.

FIG. 25 illustrates generally an example 2500 that can include providing a first signal, receiving a second signal, or extracting information indicative of lead motion from the second signal, such as using circuitry or techniques as discussed above in the examples of FIGS. 20-24.

At 2510, a first signal can be provided to excite the ambulatory medical device 2005. In an example, the first signal can be a non-tissue-stimulating electrical signal. For example, the first signal can be an AC signal generated or provided by an excitation circuit 2010. In an example, the first signal can be provided to an implantable lead 2050.

At 2530, a second signal can be received in response to the first signal. In an example, the detection circuit 2020 can be configured to receive the second signal from the implantable lead 2050. In an example, the second signal can include, among other signals, a phase-shifted or modulated version of the first signal, a voltage signal, a logic signal, or a data signal including information indicative of motion of the implantable lead.

At 2550, information can be extracted from the second signal. The extracted information can indicate motion of the implantable lead 2050. In an example, the information can indicate a relative or absolute indication of a displacement of the implantable lead 2050. In an example, the information can include an electrical representation of mechanical vibration or motion coupled to the lead, such as including a heart sound, a blood pressure sound, or respiratory sound, among others.

Figure 26:
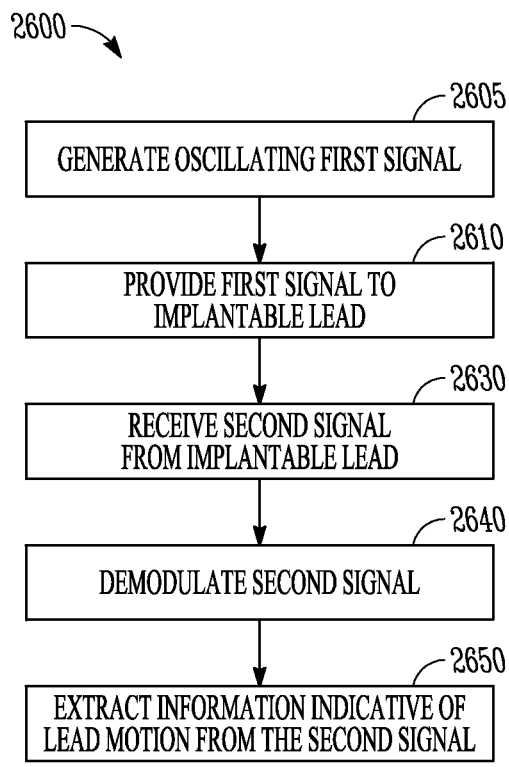
FIG. 26 illustrates generally an example that can include generating an oscillating first signal, providing the first signal to an implantable lead, receiving a second signal from the implantable lead, demodulating the second signal, or extracting information indicative of lead motion from the second signal.

FIG. 26 illustrates generally an example 2600 that can include generating an oscillating first signal, providing the first signal to an implantable lead, receiving a second signal from the implantable lead, demodulating the second signal, or extracting information indicative of lead motion, such as using circuitry or techniques discussed above with respect to FIGS. 20-24.

At 2605, a first signal can be generated by an oscillator circuit included in an excitation circuit 2010. In an example, the oscillator circuit can include a Colpitts oscillator. In an example, the first signal can include an AC signal and the frequency of oscillation can be tunable such as to achieve a specified sensitivity.

At 2610, the first signal can be provided to the implantable lead 2050, such as via an interconnect 2260 and a lead coupling 2070. In an example, the first signal can be coupled through a series capacitor with high DC or near-DC impedance to create a relatively constant current signal into the implantable lead 2050. In an example, a change in capacitance of the implantable lead 2050 can modulate the impedance of the circuit comprising the implantable lead 2050, the lead coupling 2070, and the interconnect 2260.

At 2630, a second signal can be received from the implantable lead 2050, such as in response to the first signal. In an example, the modulated impedance of the circuit comprising the implantable lead 2050, the lead coupling 2070, and the interconnect 2260 can produce the second signal in response to the first signal such that the second signal can be different than the first signal.

At 2640, the second signal can be demodulated to recover the information indicative of lead motion. In an example, the second signal can be received by a detection circuit 2220 wherein a demodulation circuit 2225 can be used to demodulate the received second signal. The demodulation circuit 2225 can include a tuned resonant transformer 2221 or an envelope detector 2223, wherein the transformer 2221 can be configured to provide an impedance-matched coupling between the second signal and the envelope detector. In an example, the second signal can include a voltage that can be detected between conductors in the implantable lead 2050, including a voltage that can include a phase-shifted version of the first signal. In this example, information indicative of lead motion can be realized by extracting a relatively low frequency component of a time-varying voltage from the second signal using the envelope detector 2223. In an example, the second signal comprises a large DC voltage with a small AC voltage superimposed, wherein the AC voltage can result from the response of the first signal to the modulated impedance. In an example, the implantable lead 2050 can be implanted in a heart and provided with the first signal. In this example, the resulting AC component of the second signal can include information about heart wall motion (or information indicative of one or more other mechanical vibrations coupled to the lead 2050).

At 2650, information can be extracted from the demodulated second signal that can indicate motion of the implantable lead 2050. In an example, the second signal can be received from the implantable lead 2050. In an example, the second signal can be relatively constant over time (e.g., relatively constant in frequency or in amplitude, among other parameters) for a stationary or immobilized implantable lead 2050 because the impedance of the implantable lead 2050 can remain relatively unchanged at equilibrium. However, as the implantable lead 2050 undergoes movement (or as mechanical vibration is coupled to the lead), the movement of the implantable lead 2050 can modulate or change the impedance of the system containing the one or more conductors in the implantable lead 2050, and the second signal can deviate from its relatively constant amplitude or frequency. For example, a mechanical vibration coupled to the implantable lead 2050 can produce a microphonic effect such as receiving the vibration information by the implantable lead 2050 and providing a second signal in response to the first signal that is analogous to the received vibration. In this example, the mechanical vibration is effectively translated to an analogous electrical signal.

In an example, more than one implantable lead can be included in the ambulatory medical device 2200, as previously described. In this example, the first signal can be provided to the system comprising the multiple implantable leads and the second signal can be received from the same system. In an example, the relative or independent motion of the two or more leads can modulate the impedance of the system comprising the leads. In an example, the additional leads can provide a greater magnitude of impedance modulation of the system comprising the sensing elements, therefore exaggerating the response signal under some circumstances (e.g., using a "differential" measurement of multiple lead impedances or capacitances). Under some other set of circumstances, the impedance modulation of the system comprising the multiple sensing elements may have a nullifying effect on the response signal. In such an example, the implantable leads can be implanted or configured, or the conductors used for sensing can be selected, in such a manner as to create a specified response or sensitivity.

In an example, the demodulated signal can be provided to a signal processor 2230 for further extracting the information indicative of motion of the implantable lead 2050. In an example, the second signal can be high pass filtered to remove the low frequency wall motion and isolate higher frequency blood flow motion information. In this example, the pitch of the resulting signal can be related to the velocity of the blood flow. In an example, a demodulated and filtered signal can be transmitted, such as via an output 2240, to an external assembly, such as for visual or audible presentation to a clinician or care giver, such as using an audio amplifier. In an example, an examiner can listen to the blood flow information or the heart wall motion information provided by the medical device. For example, when the information indicative of motion includes a subsonic or ultrasonic component, such components can be respectively upconverted or downconverted (e.g., adjusted in speed or frequency) for playback using an audible range of frequencies.

Figure 27:
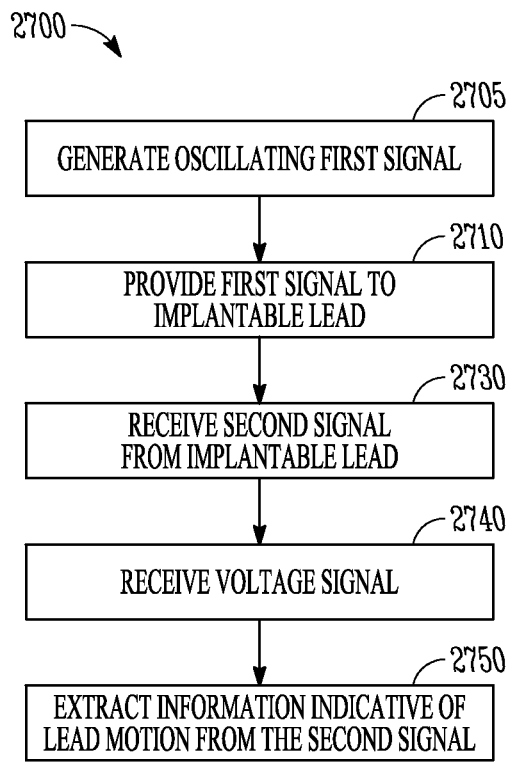
FIG. 27 illustrates generally an example of a portion of a method such as including generating an oscillating first signal, providing the first signal to an implantable lead, receiving a second signal from the implantable lead, receiving a voltage, or extracting information indicative of lead motion from the received voltage.

FIG. 27 illustrates generally an example 2700 that can include generating an oscillating first signal, providing the first signal to an implantable lead, receiving a second signal from the implantable lead, receiving a voltage signal, or extracting information indicative of lead motion from the voltage signal, such as using circuitry or techniques discussed above with respect to FIGS. 20-24.

At 2705, a first signal can be generated by an oscillator circuit included in excitation circuit 2010. In an example, the oscillator circuit can include a Pierce oscillator. In an example, the frequency of oscillation can in part determine the sensitivity of a system 2300. The frequency of the first signal can be specified to correspond to one or more frequencies that exhibit a change in impedance of an implantable lead 2050 at least in part due to motion of the implantable lead 2050.

At 2710, a first signal can be provided to the implantable lead 2050. In an example, the first signal can be an AC signal routed through a bridge circuit 2321. In this example, the implantable lead 2050 can form a portion (e.g., one of the legs) of the bridge circuit 2321. In an example, a capacitive element 2325 forms the leg of the bridge circuit 2321 that is opposite the implantable lead 2050. In an example, positive half cycles of the first signal can charge a first capacitance provided by the implantable lead 2050. In an example, the capacitive element 2325 can act as a second capacitance, which can be charged during negative half cycles of the first signal.

At 2730, a second signal can be received from the implantable lead 2050 wherein the second signal can be a response to the first signal. In an example, the second signal can be a voltage signal indicating a voltage across the first capacitance, and thus a change in capacitance of the implantable lead 2050 can be transformed into a voltage signal. The second signal can be a voltage signal indicating a voltage across the second capacitance.

At 2740, the voltage signal can be received. In an example, a voltage signal indicating a change in capacitance can be received by the envelope detector 2327. In an example, the envelope detector 2327 can be a diode or rectifier detector or a synchronous detector operating at the same frequency as the first signal. In an example, the voltage across the envelope detector 2327 can include a relatively constant value (e.g., amplitude or frequency) when the implantable lead 2050 is at equilibrium. However, when the capacitance of implantable lead 2050 changes, such as during a movement of the implantable lead 2050, the voltage across the envelope detector 2327 can change by an amount proportional to the displacement of the implantable lead 2050, the magnitude of the change in capacitance indicative of displacement.

At 2750, information can be extracted from the envelope detector 2327 that can be indicative of motion of the implantable lead 2050. In an example, a signal can be transmitted to an external source and amplified by an audio amplifier. In an example, an examiner can listen to heart sound information, as discussed above in the example of FIG. 26. In an example, heart wall motion information can be isolated and visually or audibly presented to the examiner (e.g., a clinician or caregiver).

Figure 28:
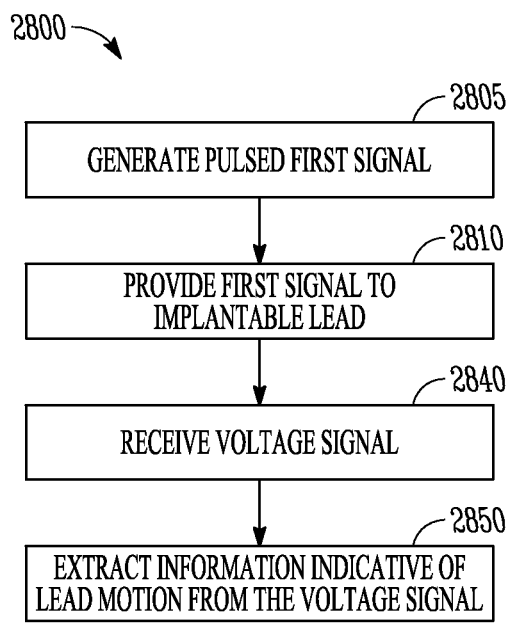
FIG. 28 illustrates generally an example that can include generating a pulsed first signal, providing the first signal to an implantable lead, receiving a voltage, or extracting information indicative of lead motion from the received voltage.

FIG. 28 illustrates generally an example 2800 that can include generating a pulsed first signal, providing the first signal to an implantable lead, receiving a voltage, or extracting information indicative of lead motion, such as using circuitry or techniques discussed above with respect to FIGS. 20-24.

At 2805, a first signal can be generated by a pulse generator. In an example, the pulse generator can produce a sequence of square wave pulses, or pulses having one or more other specified levels, duty cycles, repetition rates, or the like.

At 2810, a first signal can be provided to an implantable lead 2050. In an example, a first signal can be received from the excitation circuit 2410 by the detection circuit 2420. The received first signal can be coupled to the multiplexer 2421 in detection circuit 2420. In an example, the multiplexer 2421 can be coupled to the implantable lead 2050 via the interconnect 2460 and the lead coupling 2070. In an example, the detection circuit 2420 can include a multiplexer 2421 that can control the coupling of the first signal to the implantable lead 2050. The multiplexer 2421 can also be configured to apply a first signal to the capacitive element 2425.

At 2840, a voltage signal can be received. In an example, the multiplexer 2421 can be configured to apply a first signal to the implantable lead 2050 for a specified duration of time. In an example, the voltage signal can include a first voltage measurement of the implantable lead after a specified duration of time. In an example, the multiplexer 2421 can be configured to apply a first signal to the capacitive element 2425 for a specified duration of time (e.g., to charge the capacitive element 2425). The voltage signal can include a second voltage measurement of the capacitive element 2425 after a specified duration of time.

At 2850, information can be extracted from one or more of the first or second voltage signals indicative of motion of an implantable lead 2050. In an example, the voltage signal can be compared to a specified threshold voltage, or one or more voltage signals can be compared to an array of threshold voltages.

Figure 29:
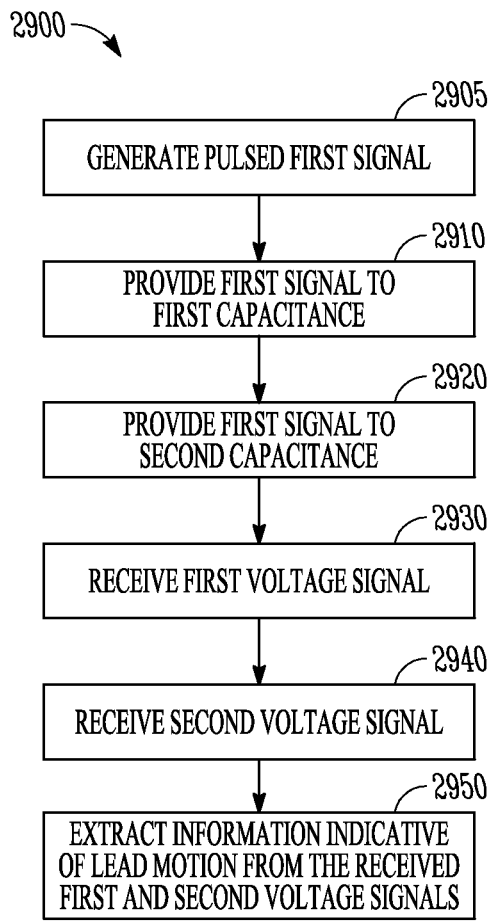
FIG. 29 illustrates generally an example that can include generating a pulsed first signal, providing the first signal to a first capacitance, providing the first signal to a second capacitance, receiving a first voltage, receiving a second voltage, or extracting information indicative of lead motion from the received first and second voltages.

FIG. 29 illustrates generally an example 2900 that can include generating a pulsed first signal, providing the pulsed first signal to a first capacitance, providing the pulsed first signal to a second capacitance, receiving a first voltage, receiving a second voltage, or extracting information indicative of lead motion.

At 2905, a first signal can be generated by a pulse generator. In an example, the pulse generator can produce pulses such as including one or more current or voltage pulses including pulses of a specified amplitude, duty cycle, or morphology, among other parameters.

At 2910, a first signal can be provided to a first capacitance. In an example, the first capacitance can be provided at least in part by the implantable lead 2050. In an example, the first signal can be received from the excitation circuit 2410 by the detection circuit 2420. The received first signal can be coupled to the multiplexer 2421 in the detection circuit 2420. The multiplexer 2421 can be coupled to the implantable lead 2050 via the interconnect 2460 and the lead coupling 2070. In an example, the detection circuit 2420 can operate the multiplexer 2421 to determine when a first signal can be applied to the implantable lead 2050.

At 2920, the first signal can be similarly provided to the second capacitance. For example, the second capacitance can be provided by the capacitive element 2425. In an example, the multiplexer 2421 can be coupled to the capacitive element 2425. In an example, the detection circuit 2420 can operate the multiplexer 2421 to controllably couple the first signal to the second capacitance. The capacitive element 2425 can be a discrete or distributed capacitor or a combination of capacitors providing a specified capacitance value, a second implantable lead, or an array of interconnected implantable leads or conductors, among others.

At 2930, a first voltage signal can be received. The first voltage signal can be a signal in response to the first signal. In an example, the first voltage signal can indicate, among other things, a charge level of the first capacitance or a first count of a number of pulses provided by the first signal.

At 2940, the second voltage signal can be received. The second voltage signal can be a signal in response to the first signal. In an example, the second voltage signal can indicate, among other things, a charge level of the second capacitance or a second count of a number of pulses provided by the first signal.

At 2950, information can be extracted from the first and second voltage signals indicative of motion of the implantable lead 2050. In an example, the first and second voltage signals can represent, respectively, a duration of respective first and second capacitor charge times. In this example, the first charge time can include an interval wherein the voltage across the first capacitance is between a lower voltage threshold and an upper voltage threshold. Similarly, the second charge time can include an interval wherein the voltage across the second capacitance is between the lower and upper voltage thresholds. In an example, information indicative of lead motion can be extracted by determining a relative indication of the first and second durations. For example, the first duration can be measured to be greater or lesser than the second duration. For example, the difference between the first and second durations can indicate the magnitude of the displacement of the implantable lead 2050, wherein the displacement causes a change in the first capacitance. In an example, when the first and second duration of a charge time are approximately equivalent, the relative indication of information can indicate that the implantable lead 2050 is stationary or otherwise at equilibrium.

In an example, the first voltage signal can represent a first count of a number of pulses provided to the first capacitance. Similarly, the second voltage signal can represent a second count of a number of pulses provided to the second capacitance. In an example, information indicative of lead motion can be extracted by determining a relative indication of the first and second counts. For example, the difference between the first and second counts can indicate the magnitude of the displacement of the implantable lead 2050, wherein the displacement causes a change in the first capacitance. In an example, when the first and second counts are approximately equivalent or unchanging, the relative indication of information can indicate that the implantable lead 2050 is stationary or otherwise at equilibrium.

Figure 30:
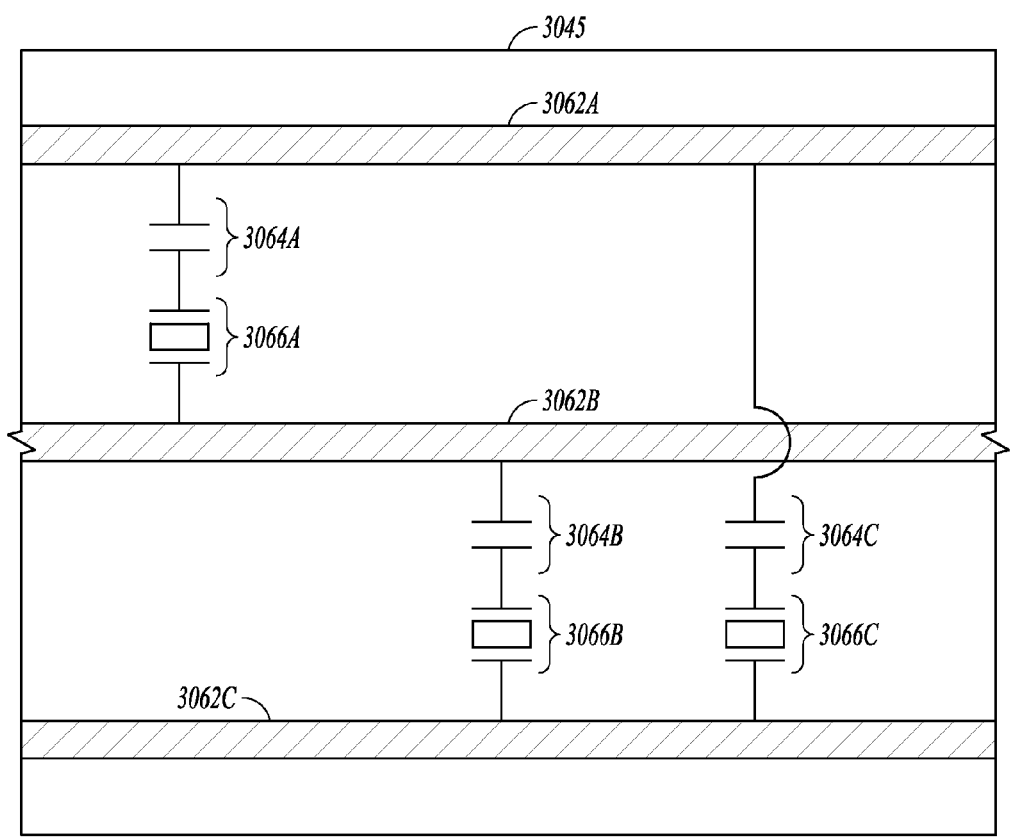
FIG. 30 illustrates generally an example of a portion of an implantable lead assembly that can include one or more transducers.

FIG. 30 illustrates generally an example of a portion of an implantable lead assembly 3045 that can include one or more piezoelectric transducers. In the example of FIG. 30, the implantable lead can include a first conductor 3062A, a second conductor 3062B, or a third conductor 3062C. A first transducer 3066A can be located on or within the lead assembly 3045, such as electrically coupled between the first conductor 3062A and the second conductor 3062B, such as including a first series capacitor 3064A (e.g., a DC-blocking capacitor). Similarly, a second transducer 3066B can be electrically coupled between the second conductor 3062B and the third conductor 3062C, such as via a second series capacitor 3064B. A third transducer 3066C can be electrically coupled between the first conductor 3062A and the third conductor 3062C, such as via a third series capacitor 3064C. Thus, in the example of FIG. 30, one or more of the transducers 3066A-C can be sampled or addressed via measurement or stimulation of a desired conductor pair (e.g., first and third conductors 3062A-C to address the third transducer 3066C, etc.).

In an example, one or more of the transducers 3066A-C can be excited such as to convert a non-therapeutic, non-stimulating electrical signal into acoustic energy (e.g., to provide acoustic energy such as ultrasonic energy). Conversely, one or more of the transducers 3066A-C can be configured for one or more of passive reception of acoustic energy (or mechanical vibration), or for reception of the acoustic transmission provided by another transducer, or the transducer being excited can modulate the excitation signal in response to received mechanical or acoustic energy. One or more of the conductors 3062A-C can be therapy delivery or cardiac electrical activity sensing conductors (e.g., the lead assembly 3045 need not carry extra conductors dedicated for use by the one or more transducers 3066A-C).

One or more of the transducers 3066A-C can include a piezoelectric construction, such as including metal or other conductive materials coupled to a lead-zirconate titanate material (PZT) piezoelectric material or coupled to a polyvinylidene fluoride (PVDF) piezoelectric material. For example, one or more of transducers 3066A-C can be used to measure blood velocity or other physiologic velocities relative to the transducer location, such as using a Doppler technique (e.g., a continuous-wave Doppler flow measurement). For example, a flow signal obtained using such techniques can include a high-frequency portion corresponding to the moving blood, a low frequency portion corresponding to heart wall motion, and a near-DC component such as corresponding to phase noise of an oscillator used to excite the transducer.

In an example, acoustic transmissions can be made between one of the transducers 3066A-C and another one of the transducers 3066A-C, such as to obtain information about a distance between various transducers 3066A-C. Such a distance can be determined via measurement of the time-delay between initiating an acoustic transmission at a first location and receiving a corresponding transmission at a second location. Thus, in the example of FIG. 30, such time-of-flight measurements can provide independent information about three different distances (e.g., between pairs of transducers 3066A-C, or between one or more of the transducers 3066A-C and another acoustic transmitter or receiver elsewhere), which can be tracked to reveal relative changes in displacement of portions of the implantable lead 3045. Multipath or other errors can be controlled or reduced such as by time-gating the received acoustic energy such as to capture the first (e.g., direct) or other desired time-of-flight between a desired transmit-receive transducer pair.

The selection of piezoelectric materials and operating frequency ranges can include considerations of size or mechanical flexibility, or directivity of resulting acoustic (e.g., ultrasonic) transmission or reception. For example, the frequency can be selected to be high enough that the corresponding acoustic wavelength is small with respect to the dimensions of the transducer, providing more omni-directional transmission or reception of acoustic energy.

In an example, the one or more transducers 3066A-C can be addressed using a frequency-selective technique. For example, a resonant device such as a thickness-mode PZT device can be excited with a burst of electrical energy corresponding to the PZT device's resonant frequency. Two or more transducers can be placed parallel to each other electrically, such as at specified locations along the implantable lead assembly 3045, such as including staggered or offset resonant frequencies, such as to provide spatially-addressable transducers that can be addressed using a desired frequency range corresponding to the resonant of a desired transducer at a specified location.

In an example, one or more of the transducers 3066A-C need not be resonant. For example, non-resonant PVDF transducers can be used interchangeably for transmission or reception of acoustic energy. In an example, a narrow-band PZT transmitting transducer can be used, and a broadband PVDF receiving transducer can be used. In this manner, the PVDF receiver need not be carefully matched or tuned to the PZT transmitter.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus including an implantable medical device, the implantable medical device (IMD) comprising:
a receiver circuit, configured to be electrically coupled to a conductor comprising a portion of an implantable lead, the receiver circuit configured to receive a response of the conductor of the implantable lead to an excitation signal applied to excite the conductor of the implantable lead, the response based on the excitation signal and modulated according to a change in an electrical characteristic of the conductor itself, to obtain information about the excited conductor itself that is indicative of a movement of the implantable lead due at least in part to a motion of a heart; and
a processor circuit configured to determine one or more of (1) whether a cardiac mechanical contraction occurred during a specified interval included in the obtained information indicative of the movement of the implantable lead, or (2) information about the cardiac mechanical contraction using the obtained information indicative of the movement of the implantable lead.

2. The apparatus of claim 1, wherein the processor circuit is configured to determine whether a cardiac mechanical contraction occurred during a specified interval included in the obtained information indicative of the movement of the implantable lead.

3. The apparatus of claim 1, wherein the processor circuit is configured to determine information about a cardiac mechanical contraction using the obtained information indicative of the movement of the implantable lead.

4. The apparatus of claim 1, further comprising an implantable lead configured to be located within or near the heart, wherein the implantable lead comprises a piezoelectric acoustic transducer configured to receive acoustic information indicative of the movement of the implantable lead, the piezoelectric acoustic transducer coupled to the conductor included in the implantable lead.

5. The apparatus of claim 1, wherein the IMD comprises an excitation circuit configured to provide a non-tissue stimulating, non-therapeutic electrical excitation signal to the implantable lead, the signal comprising a time-varying signal including a first range of frequencies.

6. The apparatus of claim 5, wherein the information indicative of the movement of the implantable lead includes one or more of magnitude information, or phase information, corresponding to one or more frequencies included in the first range of frequencies, the magnitude information, or phase information, determined at least in part using an electrical response signal provided by the implantable lead in response to the excitation signal and the movement of the implantable lead.

7. The apparatus of claim 6, wherein one or more of the magnitude information, or the phase information, includes a time-varying portion corresponding to the movement of the implantable lead.

8. The apparatus of claim 1, wherein the processor circuit is configured to determine information about the mechanical contraction via determining one or more of (1) an interval between two loci included in a mechanical contraction waveform, (2) an amplitude corresponding to a portion of the mechanical contraction waveform, or (3) information indicative of a rate of change of a portion of the mechanical contraction waveform, wherein the processor circuit is configured to obtain the mechanical contraction waveform at least in part via filtering the information indicative of the movement of the implantable lead.

9. The apparatus of claim 8, wherein the processor is configured to determine the amplitude corresponding to a portion of the mechanical contraction waveform using one or more of a central tendency, a peak-to-peak determination, a peak determination, a root-mean-square determination, a statistical ranking, or an absolute value of at least a portion of the mechanical contraction waveform.

10. The apparatus of claim 8, wherein the two loci include a first locus corresponding to a feature at or near an initiation of a cardiac contraction on the mechanical contraction waveform, or a second locus corresponding to a feature at or near a peak of the mechanical contraction waveform.

11. The apparatus of claim 1, further comprising an electrostimulation therapy circuit configured to provide an electrostimulation therapy to the heart;
wherein, in response to information about whether a cardiac mechanical contraction occurred, the processor circuit is configured to automatically adjust one or more of an electrostimulation pulse width, an electrostimulation pulse amplitude, or a timing of delivery of electrostimulation therapy to be provided by the electrostimulation therapy circuit.

12. The apparatus of claim 1, further comprising an implantable lead configured to be located within or near the heart, the implantable lead including an electrode configured to provide one or more of electrostimulation to the heart or to sense cardiac electrical activity.

13. The apparatus of claim 12, further comprising a first lead located within or near a first location of the heart; and
a second lead located within or near a second location of the heart.

14. The apparatus of claim 13, wherein the information indicative of a movement of the implantable lead due at least in part to a motion of the heart comprises a composite mechanical contraction waveform obtained using a first mechanical contraction waveform obtained from the first lead and a second mechanical contraction waveform obtained from the second lead.

15. The apparatus of claim 1, further comprising the conductor, wherein the conductor comprises one or more of a cardiac therapy delivery conductor or a cardiac electrical activity sensing conductor, the conductor configured to be coupled to an implantable electrode included as a portion of the implantable lead.

16. An implantable medical device (IMD) including a non-transitory processor-readable medium comprising instructions that, when executed by the processor, cause the IMD to:
obtain information indicative of movement of a conductor of an implantable lead, using a response of the conductor to an excitation signal applied to excite the conductor of the implantable lead, the response based on the excitation signal and modulated according to a change in an electrical characteristic of the conductor itself, the conductor electrically coupled to a receiver circuit, the receiver circuit included as a portion of the IMD, and the movement due at least in part to a motion of a heart; and
determine one or more of (1) whether a cardiac mechanical contraction occurred during a specified interval included in the obtained information indicative of the movement of the implantable lead, or (2) information about the cardiac mechanical contraction using the obtained information indicative of the movement of the implantable lead.

17. The IMD of claim 16, wherein the non-transitory processor-readable medium comprises instructions that, when executed by the processor, cause the IMD to filter the information indicative of the movement of the implantable lead to obtain a mechanical contraction waveform.

18. The IMD of claim 17, wherein the non-transitory processor-readable medium comprises instructions that, when executed by the processor, cause the IMD to determine information about the mechanical contraction via determining one or more of (1) an interval between two loci included in the mechanical contraction waveform, (2) an amplitude corresponding to a portion of the mechanical contraction waveform, or (3) information indicative of a rate of change of a portion of the mechanical contraction waveform.

19. The IMD of claim 18, wherein the non-transitory processor-readable medium comprises instructions that, when executed by the processor, cause the IMD to determine the amplitude corresponding to a portion of the mechanical contraction waveform using one or more of a central tendency, a peak-to-peak determination, a peak determination, a root-mean-square determination, a statistical ranking, or an absolute value of at least a portion of the mechanical contraction waveform.

20. The IMD of claim 18, wherein the two loci include a first locus corresponding to a feature at or near initiation of a cardiac contraction on the mechanical contraction waveform, or a second locus corresponding to a feature at or near a peak of the mechanical contraction waveform.

21. The IMD of claim 16, wherein the non-transitory processor-readable medium comprises instructions that, when executed by the processor cause the IMD to automatically adjust one or more of an electrostimulation pulse width, an electrostimulation pulse amplitude, or a timing of delivery of electrostimulation therapy to be provided by the electrostimulation therapy circuit, in response to the determination of whether a cardiac mechanical contraction occurred.

22. An apparatus including an implantable medical device, the implantable medical device (IMD) comprising:
means for obtaining information indicative of movement of a conductor of an implantable lead, using a response of the conductor to an excitation signal applied to excite the conductor of the implantable lead, the response based on the excitation signal and modulated according to a change in an electrical characteristic of the conductor itself, the conductor electrically coupled to a receiver circuit, the receiver circuit included as a portion of the IMD, and the movement due at least in part to a motion of a heart; and
means for determining one or more of (1) whether a cardiac mechanical contraction occurred during a specified interval included in the obtained information indicative of the movement of the implantable lead, or (2) information about the cardiac mechanical contraction using the obtained information indicative of the movement of the implantable lead.

23. The apparatus of claim 22, wherein the IMD comprises means for automatically adjusting one or more of an electrostimulation pulse width, an electrostimulation pulse amplitude, or a timing of delivery of electrostimulation therapy to be provided by the electrostimulation therapy circuit, in response to information about whether a cardiac mechanical contraction occurred.

* * * * *